(12) United States Patent
Palli et al.

(10) Patent No.: US 7,935,510 B2
(45) Date of Patent: May 3, 2011

(54) MUTANT RECEPTORS AND THEIR USE IN A NUCLEAR RECEPTOR-BASED INDUCIBLE GENE EXPRESSION SYSTEM

(75) Inventors: Subba Reddy Palli, Lexington, KY (US); Mohan Basavaraju Kumar, Toronto, CA (US)

(73) Assignee: Intrexon Corporation, Blacksburg, VA (US)

( * ) Notice: Subject to any disclaimer, the term of this patent is extended or adjusted under 35 U.S.C. 154(b) by 493 days.

(21) Appl. No.: 11/118,855

(22) Filed: Apr. 29, 2005

(65) Prior Publication Data
US 2005/0266457 A1 Dec. 1, 2005

Related U.S. Application Data

(60) Provisional application No. 60/567,294, filed on Apr. 30, 2004, provisional application No. 60/609,424, filed on Sep. 13, 2004.

(51) Int. Cl.
| | |
|---|---|
| C12N 1/20 | (2006.01) |
| C12N 5/00 | (2006.01) |
| C12N 1/00 | (2006.01) |
| C12N 15/00 | (2006.01) |
| C12P 21/04 | (2006.01) |
| C12P 21/06 | (2006.01) |
| C07H 21/04 | (2006.01) |
| C07H 21/02 | (2006.01) |

(52) U.S. Cl. ............... 435/252.3; 435/325; 435/254.11; 435/320.1; 435/69.7; 435/69.1; 536/23.5; 536/23.1; 536/23.4

(58) Field of Classification Search .................. None
See application file for complete search history.

(56) References Cited

U.S. PATENT DOCUMENTS

| | | |
|---|---|---|
| 4,631,211 A | 12/1986 | Houghten |
| 4,859,609 A | 8/1989 | Dull et al. |
| 4,954,655 A | 9/1990 | Kelly |
| 4,981,784 A | 1/1991 | Evans et al. |
| 4,985,461 A | 1/1991 | Hsu et al. |
| 5,010,175 A | 4/1991 | Rutter et al. |
| 5,071,773 A | 12/1991 | Evans |
| 5,117,057 A | 5/1992 | Hsu et al. |
| 5,171,671 A | 12/1992 | Evans et al. |
| 5,225,443 A | 7/1993 | Murphy et al. |
| 5,283,173 A | 2/1994 | Fields et al. |
| 5,378,726 A | 1/1995 | Yanagi et al. |
| 5,424,333 A | 6/1995 | Wing |
| 5,429,952 A | 7/1995 | Garner et al. |
| 5,459,127 A | 10/1995 | Felgner et al. |
| 5,514,578 A | 5/1996 | Hogness et al. |
| 5,530,028 A | 6/1996 | Lidert et al. |
| 5,599,904 A | 2/1997 | Evans et al. |
| 5,639,616 A | 6/1997 | Liao et al. |
| 5,641,652 A | 6/1997 | Oro et al. |
| 5,668,175 A | 9/1997 | Evans et al. |
| 5,688,691 A | 11/1997 | Oro et al. |
| 5,710,004 A | 1/1998 | Evans et al. |
| 5,723,329 A | 3/1998 | Mangelsdorf et al. |
| 5,880,333 A | 3/1999 | Goff et al. |
| 5,919,667 A | 7/1999 | Gage et al. |
| 5,939,442 A | 8/1999 | Evans et al. |
| 5,989,863 A | 11/1999 | Tang et al. |
| 6,013,836 A | 1/2000 | Hsu et al. |
| 6,025,483 A | 2/2000 | Yanosky |
| 6,096,787 A | 8/2000 | Evans et al. |
| 6,117,639 A | 9/2000 | Germann et al. |
| 6,147,282 A | 11/2000 | Goff et al. |
| 6,245,531 B1 | 6/2001 | Hogness et al. |
| 6,265,173 B1 | 7/2001 | Evans et al. |
| 6,281,330 B1 | 8/2001 | Evans et al. |
| 6,300,488 B1 | 10/2001 | Gage et al. |
| 6,326,166 B1 | 12/2001 | Pomerantz et al. |
| 6,333,318 B1 | 12/2001 | Evans et al. |
| 6,379,945 B1 | 4/2002 | Jepson et al. |
| 6,410,245 B1 | 6/2002 | Northrop et al. |
| 6,458,926 B1 | 10/2002 | Evans et al. |
| 6,504,082 B1 * | 1/2003 | Albertsen et al. ............. 800/278 |
| 6,635,429 B1 | 10/2003 | Leid et al. |
| 6,723,531 B2 | 4/2004 | Evans et al. |
| 6,756,491 B2 | 6/2004 | Evans et al. |
| 6,875,569 B2 | 4/2005 | Gage et al. |
| 6,939,711 B2 | 9/2005 | Goff et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 | 8/2006 | Palli et al. |
| 7,119,077 B1 | 10/2006 | Evans et al. |
| 7,183,061 B2 | 2/2007 | Jepsen et al. |
| 7,456,315 B2 * | 11/2008 | Hormann et al. ............. 564/148 |
| 7,531,326 B2 | 5/2009 | Kapitskaya et al. |
| 7,776,587 B2 | 8/2010 | Palli et al. |
| 7,807,417 B2 | 10/2010 | Palli et al. |

(Continued)

FOREIGN PATENT DOCUMENTS

CN 1313276 9/2001

(Continued)

OTHER PUBLICATIONS

SCORE Report, 20070814-162504us-11-118-855-1.rpr. and .rup.-.*
Wang et al.Nuc. Acids Res. 27: 4609-4618, 1999.*
Kaufman et al Blood 94: 3178-3184, 1999.*

(Continued)

Primary Examiner — Shulamith H Shafer
(74) Attorney, Agent, or Firm — Sterne, Kessler, Goldstein & Fox P.L.L.C.

(57) ABSTRACT

This invention relates to the field of biotechnology or genetic engineering. Specifically, this invention relates to the field of gene expression. More specifically, this invention relates to novel substitution mutant receptors and their use in a nuclear receptor-based inducible gene expression system and methods of modulating the expression of a gene in a host cell for applications such as gene therapy, large scale production of proteins and antibodies, cell-based high throughput screening assays, functional genomics and regulation of traits in transgenic organisms.

32 Claims, No Drawings

U.S. PATENT DOCUMENTS

| | | |
|---|---|---|
| 2002/0110861 A1 | 8/2002 | Dhadialla et al. |
| 2002/0119521 A1 | 8/2002 | Palli et al. |
| 2004/0033600 A1 | 2/2004 | Palli et al. |
| 2004/0096942 A1 | 5/2004 | Kapitskaya et al. |
| 2004/0197861 A1 | 10/2004 | Palli et al. |
| 2004/0235097 A1 | 11/2004 | Zhang et al. |
| 2005/0266457 A1 | 12/2005 | Palli et al. |
| 2006/0100416 A1 | 5/2006 | Palli et al. |
| 2007/0161086 A1 | 7/2007 | Palli et al. |
| 2007/0300313 A1 | 12/2007 | Palli et al. |
| 2008/0064097 A1 | 3/2008 | Palli |
| 2008/0115237 A1 | 5/2008 | Palli et al. |
| 2008/0145935 A1 | 6/2008 | Palli et al. |
| 2008/0176280 A1 | 7/2008 | Kapitskaya et al. |
| 2008/0216184 A1 | 9/2008 | Palli et al. |
| 2008/0235816 A1 | 9/2008 | Dhadialla et al. |
| 2008/0263687 A1 | 10/2008 | Kapitskaya et al. |
| 2008/0301825 A1 | 12/2008 | Palli et al. |

FOREIGN PATENT DOCUMENTS

| | | |
|---|---|---|
| EP | 234994 A1 | 1/1987 |
| EP | 461809 A1 | 6/1991 |
| EP | 798378 B1 | 3/1997 |
| EP | 965644 A2 | 6/1999 |
| EP | 965 644 A2 | 12/1999 |
| EP | 1266015 B1 | 3/2001 |
| WO | WO8912690 A1 | 12/1989 |
| WO | WO9200252 A1 | 1/1992 |
| WO | WO9428028 A1 | 5/1994 |
| WO | WO9518863 A1 | 1/1995 |
| WO | WO9521931 A1 | 1/1995 |
| WO | WO9617823 A1 | 12/1995 |
| WO | WO9625508 A1 | 2/1996 |
| WO | 9637609 A1 | 5/1996 |
| WO | 9627673 A1 | 9/1996 |
| WO | 9735985 A1 | 3/1997 |
| WO | 9738117 A1 | 10/1997 |
| WO | 9833162 A2 | 1/1998 |
| WO | WO 98/35550 A2 | 8/1998 |
| WO | 9902683 A1 | 1/1999 |
| WO | WO9936520 A1 | 1/1999 |
| WO | 99/10510 A2 | 3/1999 |
| WO | 99/10510 A3 | 3/1999 |
| WO | 9951777 A2 | 4/1999 |
| WO | 9951777 A3 | 4/1999 |
| WO | 9927365 A1 | 6/1999 |
| WO | WO 99/26966 A2 | 6/1999 |
| WO | 9936520 A1 | 7/1999 |
| WO | 9958155 A1 | 11/1999 |
| WO | 00/71743 | 11/2000 |
| WO | WO 01/02436 A1 | 1/2001 |
| WO | 0136447 | 3/2001 |
| WO | WO0170816 A2 | 3/2001 |
| WO | 0162780 | 8/2001 |
| WO | WO0266612 A2 | 2/2002 |
| WO | WO0266613 A2 | 2/2002 |
| WO | WO0266614 A2 | 2/2002 |
| WO | WO0266615 A2 | 2/2002 |
| WO | WO0229075 A2 | 4/2002 |
| WO | WO03105849 A1 | 6/2003 |
| WO | 03105849 A1 | 12/2003 |
| WO | WO2004005478 A2 | 1/2004 |
| WO | WO2004072254 A2 | 2/2004 |
| WO | WO2004078924 A2 | 2/2004 |
| WO | WO2005017126 A2 | 2/2005 |
| WO | WO2005108617 A2 | 5/2005 |
| WO | WO2006083253 A1 | 8/2006 |

OTHER PUBLICATIONS

Wigley et al. Reprod Fert Dev 6: 585-588, 1994.*
Campbell et al. Theriology 47(1): 63-72, 1997.*
Phillips, A., J Pharm Pharmacology 53: 1169-1174, 2001.*
Antoniewski C et al., The ecdysone response enhancer of the Fbp1 gene of Drosophila melanogaster is a direct target for the EcR/USP nuclear receptor, Mol Cell Biol, (1994), 14:4465-74.
Ashburner M et al., Temporal control of puffing activity in polytene chromosomes, Cold Spring Harb Symp Quant Biol, (1974), 38:655-62.
Cherbas L et al., Identification of ecdysone response elements by analysis of the Drosophila Eip28/29 gene, Genes Dev, (1991), 5:120-31.
Cho WL et al., Mosquito ecdysteroid receptor: analysis of the cDNA and expression during vitellogenesis, Insect Biochem Mol Biol, (1995), 25:19-27.
Chung AC et al., Cloning of crustacean ecdysteroid receptor and retinoid-X receptor gene homologs and elevation of retinoid-X receptor mRNA by retinoic acid, Mol Cell Endocrinol, (1998), 139:209-27.
D'Avino PP et al., The moulting hormone ecdysone is able to recognize target elements composed of direct repeats, Mol Cell Endocrinol, (1995), 113:1-9.
Dhadialla TS et al., New insecticides with ecdysteroidal and juvenile hormone activity, Annu Rev Entomol, (1998), 43:545-69.
Evans RM, The steroid and thyroid hormone receptor superfamily, Science, (1988), 240:889-95.
Fujiwara H et al., Cloning of an ecdysone receptor homolog from Manduca sexta and the developmental profile of its mRNA in wings, Insect Biochem Mol Biol, (1995), 25:845-56.
Godowski PJ et al., Signal transduction and transcriptional regulation by glucocorticoid receptor-LexA fusion proteins, Science, (1988), 241:812-6.
Guo X et al., Isolation of a functional ecdysteroid receptor homologue from the ixodid tick Amblyomma americanum (L.), Insect Biochem Mol Biol, (1997), 27:945-62.
Hannan GN et al., Cloning and characterization of LcEcR: a functional ecdysone receptor from the sheep blowfly Lucilia cuprina, Insect Biochem Mol Biol, (1997), 27:479-88.
Heberlein U et al., Characterization of Drosophila transcription factors that activate the tandem promoters of the alcohol dehydrogenase gene, Cell, (1985), 41:965-77.
Imhof MO et al., Cloning of a Chironomus tentans cDNA encoding a protein (cEcRH) homologous to the Drosophila melanogaster ecdysteroid receptor (dEcR), Insect Biochem Mol Biol, (1993), 23:115-24.
Kothapalli R et al., Cloning and developmental expression of the ecdysone receptor gene from the spruce dworm, Choristoneura fumiferana, Dev Genet, (1995), 17:319-30.
Licitra EJ et al., A three-hybrid system for detecting small ligand-protein receptor interactions, Proc Natl Acad Sci U S A, (1996), 93:12817-21.
Martinez A et al., Transcriptional activation of the cloned Heliothis virescens (Lepidoptera) ecdysone receptor (HvEcR) by muristeroneA, Insect Biochem Mol Biol, (1999), 29:915-30.
Morrison DA et al., Isolation of transformation-deficient Streptococcus pneumoniae mutants defective in control of competence, using insertion-duplication mutagenesis with the erythromycin resistance determinant of pAM beta 1, J Bacteriol, (1984), 159:870-6.
Mouillet JF et al., Cloning of two putative ecdysteroid receptor isoforms from Tenebrio molitor and their developmental expression in the epidermis during metamorphosis, Eur J Biochem, (1997), 248:856-63.
Neuberger MS et al., Recombinant antibodies possessing novel effector functions, Nature, (1984), 312:604-8.
Riddiford LM et al., Ecdysone receptors and their biological actions, Vitam Horm, (2000), 60:1-73.
Saleh DS et al., Cloning and characterization of an ecdysone receptor cDNA from Locusta migratoria, Mol Cell Endocrinol, (1998), 143:91-9.
Srini C. Perera Mspjkartsdsrp, An analysis of ecdysone receptor domains required for heterodimerization with ultraspiracle, Archives of Insect Biochemistry and Physiology, (1999), 41:61-70.
Suhr ST et al., High level transactivation by a modified Bombyx ecdysone receptor in mammalian cells without exogenous retinoid X receptor, Proc Natl Acad Sci U S A, (1998), 95:7999-8004.
Swevers L et al., The silkmoth homolog of the Drosophila ecdysone receptor (B1 isoform): cloning and analysis of expression during follicular cell differentiation, Insect Biochem Mol Biol, (1995), 25:857-66.

Verras M et al., Cloning and characterization of CcEcR. An ecdysone receptor homolog from the mediterranean fruit fly ceratitis capitata, Eur J Biochem, (1999), 265:798-808.

Wilson JM et al., Hepatocyte-directed gene transfer in vivo leads to transient improvement of hypercholesterolemia in low density lipoprotein receptor-deficient rabbits, J Biol Chem, (1992), 267:963-7.

Yao TP et al., *Drosophila ultraspiracle* modulates ecdysone receptor function via heterodimer formation, Cell, (1992), 71:63-72.

Yao TP et al., Functional ecdysone receptor is the product of EcR and Ultraspiracle genes, Nature, (1993), 366:476-9.

Christopherson KS et al., Ecdysteroid-dependent regulation of genes in mammalian cells by a *Drosophila ecdysone* receptor and chimeric transactivators, Proc Natl Acad Sci U S A, (1992), 89:6314-8.

Kakizawa T et al., Ligand-dependent heterodimerization of thyroid hormone receptor and retinold X receptor, J Biol Chem, (1997), 272:23799-804.

Koelle MR et al., The *Drosophila* EcR gene encodes an ecdysone receptor, a new member of the steroid receptor superfamily, Cell, (1991), 67:59-77.

Leid M et al., Purification, cloning, and RXR identity of the HeLa cell factor with which RAR or TR heterodimerizes to bind target sequences efficiently, Cell, (1992), 68:377-95.

Leonhardt SA et al., Agonist and antagonist induce homodimerization and mixed ligand heterodimerization of human progesterone receptors in vivo by a mammalian two-hybrid assay, Mol Endocrinol, (1998), 12:1914-30.

Metzger D et al., The human oestrogen receptor functions in yeast, Nature, (1988), 334:31-6.

No D et al., Ecdysone-inducible gene expression in mammalian cells and transgenic mice, Proc Natl Acad Sci U S A, (1996), 93:3346-51.

Perera SC et al., Studies on two ecdysone receptor isoforms of the spruce budworm, *Choristoneura fumiferana*, Mol Cell Endocrinol, (1999), 152:73-84.

Office Action mailed Jun. 13, 2005 in U.S. Appl. No. 09/965,703, inventors Palli, et al., filed Sep. 26, 2001.

Office Action mailed Nov. 24, 2004 in U.S. Appl. No. 09/965,703, inventors Palli, et al., filed Sep. 26, 2001.

Office Action mailed May 14, 2004 in U.S. Appl. No. 09/965,703, inventors Palli, et al., filed Sep. 26, 2001.

Office Action mailed Sep. 19, 2007 in U.S. Appl. No. 10/468,193, inventors Palli, et al., filed Dec. 17, 2003.

Office Action mailed Dec. 9, 2008 in U.S. Appl. No. 09/965,697, inventors Dhadialla, et al., filed Sep. 27, 2001.

Office Action mailed May 28, 2008 in U.S. Appl. No. 09/965,697, inventors Dhadialla, et al., filed Sep. 27, 2001.

Office Action mailed Aug. 9, 2007 in U.S. Appl. No. 09/965,697, inventors Dhadialla, et al., filed Sep. 27, 2001.

Office Action mailed Nov. 13, 2006 in U.S. Appl. No. 09/965,697, inventors Dhadialla, et al., filed Sep. 27, 2001.

Office Action mailed Apr. 18, 2006 in U.S. Appl. No. 09/965,697, inventors Dhadialla, et al., filed Sep. 27, 2001.

Office Action mailed Jul. 12, 2005 in U.S. Appl. No. 09/965,697, inventors Dhadialla, et al., filed Sep. 27, 2001.

Office Action delivered electronically Aug. 21, 2008 in U.S. Appl. No. 11/677,968, inventors Palli, et al., filed Feb. 22, 2007.

Office Action mailed Mar. 13, 2008 in U.S. Appl. No. 10/468,199, inventors Kapitskaya, et al., filed Dec. 17, 2003.

Office Action mailed Jun. 11, 2007 in U.S. Appl. No. 10/468,199, inventors Kapitskaya, et al., filed Dec. 17, 2003.

Office Action mailed Oct. 26, 2006 in U.S. Appl. No. 10/468,199, inventors Kapitskaya, et al., filed Dec. 17, 2003.

Office action mailed Aug. 22, 2006 in U.S. Appl. No. 10/239,134, inventors Palli et al., filed Sep. 19,2002.

U.S. Appl. No. 10/468,200, inventors Palli, et al., filed Aug. 15, 2003.

U.S. Appl. No. 10/468,192, inventors Palli, et al., filed Aug. 15, 2003.

Hayward, D.C., et al., "The sequence of *Locust* RXR, homologous to *Drosophila* Ultraspiracle, and its evolutionary implications," *Development Genes and Evolution* 209: 564-571, Springer Berlin/Heidelberg (1999).

Helmreich E.J.M., "The Biochemistry Of Cell Signalling," p. 192, Oxford University Press (2001).

Hofmann, A. et al., "Rapid retroviral delivery of tetracycline-inducible genes in a single autoregulatory cassette," *Proc. Natl. Acad. Sci. USA* 93: 5185-5190, National Academy of Sciences (1996).

Perera, S.C. et al., "An Analysis of Ecdysone Receptor Domains Required for Heterodimerization With Ultraspiracle," *Archives of Insect Biochemistry and Physiology* 41: 61-70, Wiley-Liss, Inc. (1999).

Shimizu, B-i. et al., "Molting hormonal and larvicidal activities of aliphatic acyl analogs of dibenzoylhydrazine insecticides," *Steroids* 62:638-642, Elsevier Science Inc. (1997).

Talbot, W.S., et al., "*Drosophila* Tissues with Different Metamorphic Responses to Ecdysone Express Different Ecdysone Receptor Isoforms," *Cell* 73:1323-1337, Cell Press (1993).

UniProtKB/Swiss-Protein Database, Accession No. P49880, "Ecdysone receptor," 2 pages (1996).

UniProtKB/Swiss-Protein Database, Accession No. P49883, "Ecdysone receptor," 2 pages (1996).

Office Action mailed Feb. 20, 2009 in U.S. Appl. No. 11/677,968, inventors Palli et al., filed Feb. 22, 2007.

Office Action mailed Feb. 25, 2009 in U.S. Appl. No. 11/841,325, inventors Dhadialla et al., filed Aug. 20, 2007.

Office Action mailed Feb. 24, 2009 in U.S. Appl. No. 11/841,495, inventors Palli et al., filed Aug. 20, 2007.

Office Action mailed Apr. 2, 2009 in U.S. Appl. No. 11/841,529, inventors Palli et al., filed Aug. 20, 2007.

Egea P. F; Rochel N; Birck C; Vachette P; Timmins P. A; Moras D.: "Effects of ligand binding on the association properties and conformation in solution of retinoic acid receptors RXR and RAR", Journal of Molecular Biology, London, GB—ISSN 0022-2836, vol. 307, Nr. 2, pp. 557-576, XP004466038, 2001.

Shea C; Hough D; Xiao J; Tzertzinis G; Maina C V.: "An rxr/usp homolog from the parasitic nematode, Dirofilaria immitis", Gene: An International Journal on Genes and Genomes, Elsevier, Amsterdam, NL—ISSN 0378-1119, vol. 324, pp. 171-182, XP004482485, 2004.

Bonneton F; et al.: "Rapid Divergence of the Ecdysone Receptor in Diptera and Lepidoptera Suggests Coevolution Between ECR and USP-RXR", Molecular Biology and Evolution, The University of Chicago Press, US—ISSN 0737-4038, vol. 20, Nr. 4, pp. 541-553, XP008028857, 2003.

Hayward D C; et al.: "The structure of the USP/RXR of Xenos pecki indicates that Strepsiptera are not closely related to Diptera", Development, Genes and Evolution, Berlin, DE—ISSN 0949-944X, vol. 215, Nr. 4, pp. 213-219, XP002403944, 2005.

Moradpour D; Englert C; Blum H E: "Independent Regulation of Two Separate Gene Activities in a Continuous Human Cell Line", Biological Chemistry—ISSN 1431-6730, vol. 8/9, Nr. 379, pp. 1189-1191, XP001070604, 1996.

Martinez A; et al: "Creation of Ecdysone Receptor Chimeras in Plants for Controlled Regulation of Gene Expression", Molecular and General Genetics, Springer Verlag, Berlin, DE—ISSN 0026-8925 vol. 261, Nr. 3, pp. 546-552, XP001069830, 1999.

Holt JR et al, "Functional expression of exogenous proteins in mammalian sensory hair cells infected with adenoviral vectors." J Neurophysiol. 1999, 81:1881-1888.

Glass CK et al. "Nuclear Receptor Coactivators." Curr Opin Cell Biol. 1997, 9:222-232.

Filmus J et al."Synergistic induction of promoters containing metal- and glucocorticoid-responsive elements."Nucleic Acids Res. Jun. 11, 1992; 20(11): 2755-2760.

Fields S et al. "A novel genetic system to detect protein-protein interactions." Nature 1989, 340:245-246.

Doyle DF et al. Engineering orthogonal ligand-receptor pairs from "near drugs." J Am Chem Soc. Nov. 21, 2001;123 (46):11367-71.

Carlson GR et al. "The chemical and biological properties of methoxyfenozide, a new insecticidal ecdysteroid agonist." Pest Manag Sci. Feb. 2001;57(2):115-9.

Cao S et al. "N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis." Canadian Journal of Chemistry, Mar. 2001, 79(3):272-278.

Belshaw PJ et al. "Rational Design of Orthogonal Receptor-Ligand Combinations." Angewandte Chemie. International edition in English (Angew. Chem., Int. ed. Engl.) 1995, vol. 34, No. 19, pp. 2129-2132.

Belshaw PJ et al."Controlling Protein Association and Subcellular Localization with a Synthetic Ligand that Induces Heterodimerization of Proteins." Proc Natl Acad Sci. 1996, 93:4604-7.

Andrianov VG et al. "4-Aminofurazan-3-hydroximic halides." Chemistry of Heterocyclic Compounds 1992, 28 (5):581-585.

Andrianov VG et al. "4-Amino-δ2-1,2,4-oxadiazolines." Chemistry of Heterocyclic Compounds 1991, 22(2):216-218.

International Search Report dated Feb. 22, 2007 listed Evans us5939442 Dhadialla us 20020110861; Hoppe; Perera; Kothapalli.

Hoppe UC et al. "Adenovirus-mediated Inducible Gene Expression in Vivo by Hybrid Ecdysone Receptor." Mol Therapy 2000 1(2):159-164.

Horwitz KB et al. "Nuclear receptor coactivators and corepressors." Mol Endocrinol. Oct. 1996;10(10):1167-77.

Kim JS et al."Design of TATA box-binding protein/zinc finger fusions for targeted regulation of gene expression." Proc Natl Acad Sci U S A. Apr. 15, 1997;94(8):3616-20.

Kirken RA et al. "Two discrete regions of interleukin-2 (IL2) receptor beta independently mediate IL2 activation of a PD98059/rapamycin/wortmannin-insensitive Stat5a/b serine kinase." J Biol Chem. Jun. 13, 1997;272(24):15459-65.

Nakagawa Y et al. "Quantitative structure-activity studies of insect growth regulators: XIX. Effects of substituents on the aromatic moiety of dibenzoylhydrazines on larvicidal activity against the beet armyworm Spodoptera exigua." Pest Manag Sci. Feb. 2002;58(2):131-8.

O'Brien RN et al. "Structural and functional analysis of the human phosphoenolpyruvate carboxykinase gene promoter." Biochim Biophys Acta. Dec. 27, 1995;1264(3):284-8.

Peet DJ et al."Engineering novel specificities for ligand-activated transcription in the nuclear hormone receptor RXR." Chem Biol. Jan. 1998;5(1):13-21.

Pierce AC et al."Computational Binding Studies of Orthogonal Cyclosporin-Cyclophilin Pairs." Angewandte Chemie. International edition in English (Angew. Chem., Int. ed. Engl.) 1997, vol. 36, No. 13-14, pp. 1466-1469.

Spencer DM et al. "Controlling signal transduction with synthetic ligands." Science. Nov. 12, 1993;262(5136):1019-24.

Trisyono A et al. "Effect of Nonsteroidal ecdysone agonists, methoxyfenozide and tebufenozide, on the European Corn Borer (Lepidoptera: Pyralidae)." J Economic Entomology 1997, 90:1486-1492.

Wurm FM et al. "Inducible overproduction of the mouse c-myc protein in mammalian cells." Proc Natl Acad Sci U S A. 1986, 83(15):5414-8.

Wipf P, et al. "Combinatorial synthesis and biological evaluation of library of small-molecule Ser/Thr-protein phosphatase inhibitors." Bioorg Med Chem. 1997, 5(1):165-77.

Wing KD et al. "RH 5849, a Nonsteroidal Ecdysone Agonist: Effects on Larval Lepidoptera." Science. 1988, 241 (4864):470-472.

Zhang X et al."Study on synthesis and bioactivity of new diacylhydrazine IGR JS118." Nongyao 2003, 42:18-20.

Brennan JD. "Preparation and Entrapment of Fluorescently Labeled Proteins for the Development of Reagentless Optical Biosensors." Journal of Fluorescence,Dec. 1999, 9(4): 295-312.

Office Action mailed May 12, 2010 in U.S. Appl. No. 11/841,464, inventors Palli et al., filed Aug. 20, 2007.

Office Action mailed Feb. 18, 2010 in U.S. Appl. No. 10/468,193, inventors Palli et al., filed Dec. 17, 2003.

Notice of Allowance mailed May 24, 2010 in U.S. Appl. No. 11/677,968, inventors Palli et al., filed Feb. 22, 2007.

Office action mailed Mar. 22, 2010 in U.S. Appl. No. 11/841,648, inventors Kapitskaya et al., filed Aug. 24, 2007.

Office action mailed Jun. 29, 2009 in U.S. Appl. No. 11/841,648, inventors Kapitskaya et al., filed Aug. 24, 2007.

Notice of Allowance mailed Mar. 19, 2010 in U.S. Appl. No. 11/841,495, inventors Palli et al., filed on Aug. 20, 2007.

Office Action mailed Apr. 1, 2010 in U.S. Appl. No. 11/841,529, inventors Palli et al., filed Aug. 20, 2007.

Office Action mailed Apr. 20, 2010 in U.S. Appl. No. 11/841,597, inventors Kapitskaya et al., filed Aug. 20, 2007.

Office Action mailed Oct. 21, 2009 in U.S. Appl. No. 11/841,597, inventors Kapitskaya et al., filed Aug. 20, 2007.

Office Action mailed Jun. 23, 2009 in U.S. Appl. No. 09/965,697, inventors Dhadialla, et al., filed on Sep. 27, 2001.

Office Action mailed May 25, 2010 in U.S. Appl. No. 09/965,697, inventors Dhadialla, et al., filed on Sep. 27, 2001.

Office action mailed Feb. 22, 2010 in U.S. Appl. No. 11/837,834, inventors Palli et al., filed Aug. 13, 2007.

Office action mailed May 22, 2009 in U.S. Appl. No. 11/837,834, inventors Palli et al., filed Aug. 13, 2007.

Blumberg, B., et al., "Multiple retinoid-responsive receptors in a single cell: Families of retinoid "X" receptors and retinoic acid receptors in the *Xenopous* egg," *Proc. Natl. Acad. Sci.* USA 89:2321-2325, National Academy of Sciences, United States (1992).

Clayton, G.M., et al., "The structure of the ultraspiracle ligand-binding domain reveals a nuclear receptor locked in an inactive conformation," *Proc. Natl. Acad. Sci.* 98:1549-1554, National Academy of Sciences, United States (2001).

EMBL Nucleotide Sequence Database, Accession No. AJ251542, "Tenebrio molitor mRNA for USP protein," 7 pages (Feb. 15, 2000).

Kumar, M.B., "A single point mutation in ecdysone receptor leads to increased ligand specificity: Implications for gene switch applications," *Proc. Natl. Acad. Sci.* 99: 14710-14715, National Academy of Sciences, United States (2002).

Laudet, V., et al., "A Unified Nomenclature System for the Nuclear Receptor Superfamily," *Cell* 97:161-163, Cell Press, United States (1999).

Mangelsdorf, D.J., et al., "Nuclear receptor that identifies a novel retinoic acid response pathway," *Nature* 345:224-229, Nature Publishing Group, England (1990).

Marklew, S., et al., "Isolation of a novel RXR from Xenopus that most closely resembles mammalian RXR/β and is expressed throughout early development," *Biochim Biophys Acta* 1218:267-272, Elsevier Science B.V., Netherlands (1994).

Palmer, M.J., et al., "Characterization of EcR and RXR Homologous in the Ixodid Tick, *Amblyomma americanum* (L.)," *Am. Zool.* 39:747-757, American Society of Zoologists, United States (1999).

Palli, S.R. et al , "Improved ecdysone receptor-based inducible gene regulation system," *Eur. J. Biochem.* 270: 1308-1315, Wiley Interscience (2003).

Tran, H.T. et al., "Reconstruction of Ligand-Dependent Transactivation of *Choristoneura fumiferana* Ecdysone Receptor in Yeast," *Molecular Endocrinology* 15: 1140-1153, The Endocrine Society (2001).

UniProtKB/Swiss-Protein Database, Accession No. O02035, "Ecdysone receptor," 6 pages (1997).

UniProtKB/Swiss-Protein Database, Accession No. O76246, "Ecdysteroid receptor," 6 pages (1998).

U.S. Appl. No. 11/837,834, inventors Palli et al., filed Aug. 13, 2007.

U.S. Appl. No. 12/707,599, inventors Dhadialla et al., filed Feb. 17, 2010.

Office Action mailed Sep. 28, 2010 in U.S. Appl. No. 11/841,631, inventors Palli et al., filed Aug. 20, 2007.

Office Action mailed Sep. 14, 2010 in U.S. Appl. No. 11/841,644, inventors Palli et al., filed Aug. 20, 2007.

U.S. Appl. No. 12/818,034, filed Jun. 17, 2010, inventors Palli et al.

U.S. Appl. No. 12/859,940, filed Aug. 20, 2010, inventors Palli et al.

* cited by examiner

US 7,935,510 B2

MUTANT RECEPTORS AND THEIR USE IN A NUCLEAR RECEPTOR-BASED INDUCIBLE GENE EXPRESSION SYSTEM

This application claims priority to U.S. provisional application No. 60/567,294 filed Apr. 30, 2004 and U.S. provisional application No. 60/609,424 filed Sep. 13, 2004.

FIELD OF THE INVENTION

This invention relates to the field of biotechnology or genetic engineering. Specifically, this invention relates to the field of gene expression. More specifically, this invention relates to novel nuclear receptors comprising a substitution mutation and their use in a nuclear receptor-based inducible gene expression system and methods of modulating the expression of a gene within a host cell using this inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as ecdysteroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83: 5414-5418; Arnheiter et al., 1990, Cell 62:51-61; Filmus et al., 1992, Nucleic Acids Research 20: 27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium Escherichia coli have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, Science 262: 1019-24; Belshaw et al., 1996 Proc Natl Acad Sci USA 93: 4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998, Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of ecdysteroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

The insect ecdysone receptor (EcR) heterodimerizes with Ultraspiracle (USP), the insect homologue of the mammalian RXR, and binds ecdysteroids and ecdysone receptor response elements and activate transcription of ecdysone responsive genes (Riddiford et al., 2000). The EcR/USP/ligand complexes play important roles during insect development and reproduction. The EcR is a member of the steroid hormone receptor superfamily and has five modular domains, A/B (transactivation), C (DNA binding, heterodimerization)), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of EcR-based gene switch used *Drosophila melanogaster* EcR (DmEcR) and *Mus musculus* RXR (MmRXR) and showed that these receptors in the presence of ecdysteroid, ponasteroneA, transactivate reporter genes in mammalian cell lines and transgenic mice (Christopherson et al., 1992; No et al., 1996). Later, Suhr et al., 1998 showed that non-ecdysteroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO 99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880, 333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-ecdysteroid ligands and at the same is insensitive to the natural ecdysteroids. Thus, improved systems that are simple, compact, and dependent on ligands that are relatively inexpensive, readily available and of low toxicity to the host would prove useful for regulating biological systems.

Previously, Applicants have shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-ecdysteroidal ligands for example, diacylhydrazines, when compared to ecdysteroidal ligands for example, ponasterone A ("PonA") or muristerone A ("MurA"). That is, when compared to ecdysteroids, the non-ecdysteroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

The EcR is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

To develop an improved Group H nuclear receptor-based inducible gene expression system in which ligand binding or ligand specificity is modified, Applicants created substitution mutant EcRs that comprise substituted amino acid residues in the ligand binding domain (LBD). A homology modeling and docking approach was used to predict critical residues that mediate binding of ecdysteroids and non-ecdysteroids to the EcR LBD. These substitution mutant EcRs were evaluated in ligand binding and transactivation assays. As presented herein, Applicants' novel substitution mutant nuclear receptors and their use in a nuclear receptor-based inducible gene expression system provides an improved inducible gene expression system in both prokaryotic and eukaryotic host cells in which ligand sensitivity and magnitude of transactivation may be selected as desired, depending upon the application.

DETAILED DESCRIPTION OF THE INVENTION

Applicants describe herein the construction of Group H nuclear receptors that comprise substitution mutations (referred to herein as "substitution mutants") at amino acid residues that are involved in ligand binding to a Group H nuclear receptor ligand binding domain that affect the ligand sensitivity and magnitude of induction of the Group H nuclear receptor and the demonstration that these substitution mutant nuclear receptors are useful in methods of modulating gene expression.

Specifically, Applicants have developed a novel nuclear receptor-based inducible gene expression system comprising a Group H nuclear receptor ligand binding domain comprising a substitution mutation. Applicants have shown that the effect of such a substitution mutation may increase or reduce ligand binding activity or ligand sensitivity and the ligand may be ecdysteroid or non-ecdysteroid specific. Thus, Applicants' invention provides a Group H nuclear receptor-based inducible gene expression system useful for modulating expression of a gene of interest in a host cell. In a particularly desirable embodiment, Applicants' invention provides an ecdysone receptor-based inducible gene expression system that responds solely to either ecdysteroidal ligands or non-ecdysteroidal ligands. In addition, the present invention also provides an improved non-ecdysteroidal ligand responsive ecdysone receptor-based inducible gene expression system. Thus, Applicants' novel inducible gene expression system and its use in methods of modulating gene expression in a host cell overcome the limitations of currently available inducible expression systems and provide the skilled artisan with an effective means to control gene expression.

The present invention is useful for applications such as gene therapy, large scale production of proteins and antibodies, cell-based high throughput screening assays, orthogonal ligand screening assays, functional genomics, proteomics, metabolomics, and regulation of traits in transgenic organisms, where control of gene expression levels is desirable. An advantage of Applicants' invention is that it provides a means to regulate gene expression and to tailor expression levels to suit the user's requirements.

DEFINITIONS

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA: RNA, DNA: RNA, DNA: DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., 1987, Proc. Natl. Acad. Sci. U.S.A. 84: 7413; Mackey, et al., 1988, Proc. Natl. Acad. Sci. U.S.A 85:8027-8031; and Ulmer et al., 1993, Science 259: 1745-1748). The use of cationic lipids may promote encapsulation of negatively charged nucleic acids, and also promote fusion with negatively charged cell membranes (Felgner and Ringold, 1989, Science 337:387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO 95/21931), peptides derived from DNA binding proteins (e.g., WO 96/25508), or a cationic polymer (e.g., WO 95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (see Cherbas L., et. al., (1991), *Genes Dev.* 5, 120-131); AGGTCAN$_{(n)}$AGGTCA, where N$_{(n)}$ can be one or more spacer nucleotides (see D'Avino P P., et. al., (1995), *Mol. Cell. Endocrinol,* 113, 1-9); and GGGTTGAATGAATTT (see Antoniewski C., et. al., (1994). Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR-based system, which in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (Cs-VMV), chlorophyll a/b binding protein, ribulose 1, 5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

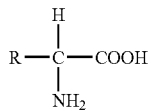

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one (1) wild-type or naturally occurring amino acid with a different amino acid relative to the wild-type or naturally occurring polypeptide. A substitution mutant polypeptide may comprise only one (1) wild-type or naturally occurring amino acid substitution and may be referred to as a "point mutant" or a "single point mutant" polypeptide. Alternatively, a substitution mutant polypeptide may comprise a substitution of two (2) or more wild-type or naturally occurring amino acids with 2 or more amino acids relative to the wild-type or naturally-occurring polypeptide. According to the invention, a Group H nuclear receptor ligand binding domain polypeptide comprising a substitution mutation comprises a substitution of at least one (1) wild-type or naturally occurring amino acid with a different amino acid relative to the wild-type or naturally occurring Group H nuclear receptor ligand binding domain polypeptide.

Wherein the substitution mutant polypeptide comprises a substitution of two (2) or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation). Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide. A mutation or mutant can be any change, including but not limited to substitutions, deletions, insertions, or any combination thereof.

A substitution mutation may be made by any technique for mutagenesis known in the art, including but not limited to, in vitro site-directed mutagenesis (Hutchinson, C., et al., 1978, J. Biol. Chem. 253: 6551; Zoller and Smith, 1984, DNA 3: 479-488; Oliphant et al., 1986, Gene 44: 177; Hutchinson et al., 1986, Proc. Natl. Acad. Sci. U.S.A. 83: 710), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215: 403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters, which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal". The present invention is useful to search for orthogonal ligands and orthogonal receptor-based gene expression systems such as those described in co-pending U.S. application Ser. No. 09/965,697, which is incorporated herein by reference in its entirety.

Gene Expression Modulation System of the Invention

Applicants have identified herein amino acid residues that are involved in ligand binding to a Group H nuclear receptor ligand binding domain that affect the ligand sensitivity and magnitude of induction in an ecdysone receptor-based inducible gene expression system. Applicants describe herein the construction of Group H nuclear receptors that comprise substitution mutations (referred to herein as "substitution mutants") at these critical residues and the demonstration that these substitution mutant nuclear receptors are useful in methods of modulating gene expression. As presented herein, Applicants' novel substitution mutant nuclear receptors and their use in a nuclear receptor-based inducible gene expression system provides an improved inducible gene expression system in both prokaryotic and eukaryotic host cells in which ligand sensitivity and magnitude of transactivation may be selected as desired, depending upon the application.

Thus, the present invention relates to novel substitution mutant Group H nuclear receptor polynucleotides and polypeptides, a nuclear receptor-based inducible gene expression system comprising such mutated Group H nuclear receptor polynucleotides and polypeptides, and methods of modulating the expression of a gene within a host cell using such a nuclear receptor-based inducible gene expression system.

In particular, the present invention relates to a gene expression modulation system comprising at least one gene expression cassette that is capable of being expressed in a host cell comprising a polynucleotide that encodes a polypeptide comprising a Group H nuclear receptor ligand binding domain comprising a substitution mutation. Preferably, the Group H nuclear receptor ligand binding domain comprising a substitution mutation is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. More preferably, the Group H nuclear receptor ligand binding domain comprising a substitution mutation is from an ecdysone receptor.

In a specific embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is a Group H nuclear receptor ligand binding domain comprising a substitution mutation. In a preferred embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

Wherein when only one nuclear receptor ligand binding domain is a Group H ligand binding domain comprising a substitution mutation, the other nuclear receptor ligand binding domain may be from any other nuclear receptor that forms a dimer with the Group H ligand binding domain comprising the substitution mutation. For example, when the Group H nuclear receptor ligand binding domain comprising a substitution mutation is an ecdysone receptor ligand binding domain comprising a substitution mutation, the other nuclear receptor ligand binding domain ("partner") may be from an ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a RXR (see applications PCT/US01/09050, U.S. 60/294,814, and U.S. 60/294,819, incorporated herein by reference in their entirety). The "partner" nuclear receptor ligand binding domain may further comprise a truncation mutation, a deletion mutation, a substitution mutation, or another modification.

Preferably, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

Preferably, the invertebrate RXR ligand binding domain is from a locust *Locusta migratoria* RXR polypeptide ("LmRXR"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

Preferably, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In a preferred embodiment, the chimeric RXR ligand binding domain comprises at least one vertebrate species RXR polypeptide fragment and one invertebrate species RXR polypeptide fragment.

In a more preferred embodiment, the chimeric RXR ligand binding domain comprises at least one vertebrate species RXR polypeptide fragment and one non-Dipteran/non-Lepidopteran invertebrate species RXR homolog polypeptide fragment.

In a specific embodiment, the gene whose expression is to be modulated is a homologous gene with respect to the host cell. In another specific embodiment, the gene whose expression is to be modulated is a heterologous gene with respect to the host cell.

The ligands for use in the present invention as described below, when combined with the ligand binding domain of the nuclear receptor(s), which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical.

In a specific example, binding of the ligand to the ligand binding domain of a Group H nuclear receptor and its nuclear receptor ligand binding domain partner enables expression or suppression of the gene. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988), Nature, 335: 563-564) or LexA protein from Escherichia coli (see Brent and Ptashne (1985), Cell, 43: 729-736), or synthetic response elements specific for targeted interactions with proteins designed, modified, and selected for such specific interactions (see, for example, Kim, et al. (1997), Proc. Natl. Acad. Sci., USA, 94:3 616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The ecdysone receptor is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), orphan receptor 1 (OR-1), steroid hormone nuclear receptor 1 (NER-1), retinoid X receptor interacting protein-15 (RIP-15), liver X receptor β (LXRβ), steroid hormone receptor like protein (RLD-1), liver X receptor (LXR), liver X receptor α (LXRα), farnesoid X receptor (FXR), receptor interacting protein 14 (RIP-14), and farnesol receptor (HRR-1).

Applicants have developed a CfEcR homology model and have used this homology model together with a published Chironomous tetans ecdysone receptor ("CtEcR") homology model (Wurtz et al., 2000) to identify critical residues involved in binding to ecdysteroids and non-ecdysteroids. The synthetic non-ecdysteroids, diacylhydrazines, have been shown to bind lepidopteran EcRs with high affinity and induce precocious incomplete molt in these insects (Wing et al., 1988) and several of these compounds are currently marketed as insecticides. The ligand binding cavity or "pocket" of EcRs has evolved to fit the long backbone structures of ecdysteroids such as 20-hydroxyecdysone (20E). The diacylhydrazines have a compact structure compared to ecdysteroids and occupy only the bottom part of the EcR binding pocket. This leaves a few critical residues at the top part of the binding pocket that make contact with ecdysteroids but not with non-ecdysteroids such as bisacylhydrazines. Applicants describe herein the construction of mutant ecdysone receptors comprising a substitution mutation at these binding pocket residues and have identified several classes of substitution mutant ecdysone receptors with modified ligand binding and transactivation characteristics.

Given the close relatedness of ecdysone receptor to other Group H nuclear receptors, Applicants' identified ecdysone receptor ligand binding domain substitution mutations are also expected to work when introduced into the analogous position of the ligand binding domains of other Group H nuclear receptors to modify their ligand binding or ligand sensitivity. One of skill in the art can identify analogous amino acid positions by sequence and function using routine methods in the art such as sequence analysis, analysis of the binding pocket through homology modeling and binding assays. Applicants' novel substitution mutated Group H nuclear receptor polynucleotides and polypeptides are useful in a nuclear receptor-based inducible gene modulation system for various applications including gene therapy, expression of proteins of interest in host cells, production of transgenic organisms, and cell-based assays.

In particular, Applicants describe herein a novel gene expression modulation system comprising a Group H nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides. Applicants have demonstrated for the first time that a substitution mutated nuclear receptor can be used as a component of a nuclear receptor-based inducible gene expression system to modify ligand binding activity and/or ligand specificity in both prokaryotic and eukaryotic cells. As discussed herein, Applicants' findings are both unexpected and surprising.

An ecdysone receptor-based gene expression modulation system of the present invention may be either heterodimeric or homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366: 476-479; Yao, et al., (1992) Cell 71: 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9: 222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. Applicants have previously shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

Gene Expression Cassettes of the Invention

The novel nuclear receptor-based inducible gene expression system of the invention comprises at least one gene expression cassette that is capable of being expressed in a host cell, wherein the gene expression cassette comprises a polynucleotide that encodes a polypeptide comprising a Group H nuclear receptor ligand binding domain comprising a substitution mutation. Thus, Applicants' invention also provides novel gene expression cassettes for use in the gene expression system of the invention.

In a specific embodiment, the gene expression cassette that is capable of being expressed in a host cell comprises a polynucleotide that encodes a polypeptide selected from the group consisting of a) a polypeptide comprising a transactivation domain, a DNA-binding domain, and a Group H nuclear receptor ligand binding domain comprising a substitution mutation; b) a polypeptide comprising a DNA-binding domain and a Group H nuclear receptor ligand binding domain comprising a substitution mutation; and c) a polypeptide comprising a transactivation domain and a Group H nuclear receptor ligand binding domain comprising a substitution mutation.

In another specific embodiment, the present invention provides a gene expression cassette that is capable of being expressed in a host cell, wherein the gene expression cassette comprises a polynucleotide that encodes a hybrid polypeptide selected from the group consisting of a) a hybrid polypeptide comprising a transactivation domain, a DNA-binding domain, and a Group H nuclear receptor ligand binding domain comprising a substitution mutation; b) a hybrid polypeptide comprising a DNA-binding domain and a Group H nuclear receptor ligand binding domain comprising a substitution mutation; and c) a hybrid polypeptide comprising a transactivation domain and a Group H nuclear receptor ligand binding domain comprising a substitution mutation. A hybrid polypeptide according to the invention comprises at least two polypeptide fragments, wherein each polypeptide fragment is from a different source, i.e., a different polypeptide, a different nuclear receptor, a different species, etc. The hybrid polypeptide according to the invention may comprise at least two polypeptide domains, wherein each polypeptide domain is from a different source.

In a specific embodiment, the Group H nuclear receptor ligand binding domain comprising a substitution mutation is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. In a preferred embodiment, the Group H nuclear receptor ligand binding domain is from an ecdysone receptor.

Thus, the present invention also provides a gene expression cassette comprising a polynucleotide that encodes a polypeptide selected from the group consisting of a) a polypeptide comprising a transactivation domain, a DNA-binding domain, and an ecdysone receptor ligand binding domain comprising a substitution mutation; b) a polypeptide comprising a DNA-binding domain and an ecdysone receptor ligand binding domain comprising a substitution mutation; and c) a polypeptide comprising a transactivation domain and an ecdysone receptor ligand binding domain comprising a substitution mutation. Preferably, the gene expression cassette comprises a polynucleotide that encodes a hybrid polypeptide selected from the group consisting of a) a hybrid polypeptide comprising a transactivation domain, a DNA-binding domain, and an ecdysone receptor ligand binding domain comprising a substitution mutation; b) a hybrid polypeptide comprising a DNA-binding domain and an ecdysone receptor ligand binding domain comprising a substitution mutation; and c) a hybrid polypeptide comprising a transactivation domain and an ecdysone receptor ligand binding domain comprising a substitution mutation; wherein the encoded hybrid polypeptide comprises at least two polypeptide fragments, wherein each polypeptide fragment is from a different source.

The ecdysone receptor (EcR) ligand binding domain (LBD) may be from an invertebrate EcR, preferably selected from the class Arthropod EcR. Preferably the EcR is selected from the group consisting of a Lepidopteran EcR, a Dipteran EcR, an Orthopteran EcR, a Homopteran EcR and a Hemipteran EcR. More preferably, the EcR ligand binding domain for use in the present invention is from a spruce budworm *Choristoneura fumiferana* EcR ("CfEcR"), a beetle *Tenebrio molitor* EcR ("TmEcR"), a *Manduca sexta* EcR ("MsEcR"), a *Heliothies virescens* EcR ("HvEcR"), a midge *Chironomus tentans* EcR ("CtEcR"), a silk moth *Bombyx mori* EcR ("BmEcR"), a squinting bush brown *Bicyclus anynana* EcR ("BanEcR"), a buckeye *Junonia coenia* EcR ("JcEcR"), a fruit fly *Drosophila melanogaster* EcR ("DmEcR"), a mosquito *Aedes aegypti* EcR ("AaEcR"), a blowfly *Lucilia capitata* ("LcEcR"), a blowfly *Lucilia cuprina* EcR ("LucEcR"), a blowfly *Calliphora vicinia* EcR ("CvEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Celuca pugilator* EcR ("CpEcR"), an ixodid tick *Amblyomma americanum* EcR ("AmaEcR"), a whitefly *Bamecia argentifoli* EcR ("BaEcR") or a leafhopper *Nephotetix cincticeps* EcR ("NcEcR"). More preferably, the LBD is from a CfEcR, a DmEcR, or an AmaEcR.

In a specific embodiment, the LBD is from a truncated EcR polypeptide. The EcR polypeptide truncation results in a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. Preferably, the EcR polypeptide truncation results in a deletion of at least a partial polypeptide domain. More preferably, the EcR polypeptide truncation results in a deletion of at least an entire polypeptide domain. In a specific embodiment, the EcR polypeptide truncation results in a deletion of at least an A/B-domain, a C-domain, a D-domain, an F-domain, an A/B/C-domains, an A/B/1/2-C-domains, an A/B/C/D-domains, an A/B/C/D/F-domains, an A/B/F-domains, an A/B/C/F-domains, a partial E domain, or a partial F domain. A combination of several complete and/or partial domain deletions may also be performed.

In a specific embodiment, the Group H nuclear receptor ligand binding domain is encoded by a polynucleotide comprising a codon mutation that results in a substitution of a) amino acid residue 48, 51, 52, 54, 92, 95, 96, 109, 110, 119, 120, 125, 128, 132, 219, 223, 234, or 238 of SEQ ID NO: 1, b) amino acid residues 96 and 119 of SEQ ID NO: 1, c) amino acid residues 110 and 128 of SEQ ID NO: 1, d) amino acid residues 52 and 110 of SEQ ID NO: 1, e) amino acid residues 107, 110, and 127 of SEQ ID NO: 1, or f) amino acid residues 52, 107 and 127 of SEQ ID NO: 1. In another embodiment, the Group H nuclear receptor ligand binding domain is encoded by a polynucleotide comprising codon mutations that results in substitution of amino acid residues 107 and 127 and insertion of amino acid 259 of SEQ ID NO: 1. In a preferred embodiment, the Group H nuclear receptor ligand binding domain is from an ecdysone receptor.

In another specific embodiment, the Group H nuclear receptor ligand binding domain is encoded by a polynucleotide comprising a codon mutation that results in a substitution of a) an asparagine, arginine, tyrosine, tryptophan, leucine or lysine residue at a position equivalent to analogous to amino acid residue 48 of SEQ ID NO: 1, b) a methionine, asparagines or leucine residue at a position equivalent or analogous to amino acid residue 51 of SEQ ID NO: 1, c) a leucine, proline, methionine, arginine, tryptophan, glycine, glutamine or glutamic acid residue at a position equivalent or analogous to amino acid residue 52 of SEQ ID NO: 1, d) a tryptophan or threonine at a position equivalent or analogous to amino acid 54 of SEQ ID NO: 1, e) a leucine or glutamic acid at a position equivalent or analogous to amino acid 92 of SEQ ID NO: 1, f) a histidine, methionine or tryptophan residue at a position equivalent or analogous to amino acid residue 95 of SEQ ID NO: 1, g) a leucine, serine, glutamic acid or tryptophan residue at a position equivalent or analogous to amino acid residue 96 of SEQ ID NO: 1, h) a tryptophan, proline, leucine, methionine or asparagine at a position equivalent or analogous to amino acid 109 of SEQ ID NO: 1, i) a glutamic acid, tryptophan or asparagine residue at a position equivalent or analogous to amino acid residue 110 of SEQ ID NO: 1, j) a phenylalanine at a position equivalent or analogous to amino acid 119 of SEQ ID NO: 1, k) a tryptophan or methionine at a position equivalent or analogous to amino acid 120 of SEQ ID NO: 1, l) a glutamic acid, proline, leucine, cysteine, tryptophan, glycine, isoleucine, asparagine, serine, valine or arginine at a position equivalent or analogous to amino acid residue 125 of SEQ ID NO: 1, m) a phenylalanine at a position equivalent or analogous to amino acid 128 of SEQ ID NO: 1, n) a methionine, asparagine, glutamic acid or valine at a position equivalent or analogous to amino acid 132 of SEQ ID NO: 1, o) an alanine, lysine, tryptophan or tyrosine residue at a position equivalent or analogous to amino acid residue 219 of SEQ ID NO: 1, p) a lysine, arginine or tyrosine residue at a position equivalent or analogous to amino acid residue 223 of SEQ ID NO: 1, q) a methionine, arginine, tryptophan or isoleucine at a position equivalent or analogous to amino acid 234 of SEQ ID NO: 1, r) a proline, glutamic acid, leucine, methionine or tyrosine at a position equivalent or analogous to amino acid 238 of SEQ ID NO: 1, s) a phenylalanine residue at a position equivalent or analogous to amino acid 119 of SEQ ID NO: 1 and a threonine at a position equivalent or analogous to amino acid 96 of SEQ ID NO: 1, t) a proline residue at a position equivalent or analogous to amino acid 110 of SEQ ID NO: 1 and a phenylalanine residue at a position equivalent or analogous to amino acid 128 of SEQ ID NO: 1, u) a valine residue at a position equivalent or analogous to amino acid 52 of SEQ ID NO: 1 and a praline residue at a position equivalent or analogous to amino acid 110 of SEQ ID NO: 1, v) an isoleucine residue at a position equivalent or analogous to amino acid 107 of SEQ ID NO: 1, a glutamic acid residue at a position equivalent or analogous to amino acid 127 of SEQ ID NO: 1 and a proline residue at a position equivalent or analogous to amino acid 110 of SEQ ID NO: 1, or w) an isoleucine at a position equivalent or analogous to amino acid 107 of SEQ ID NO: 1, a glutamic acid at a position equivalent or analogous to amino acid 127 of SEQ ID NO: 1 and a valine at a position equivalent or analogous to amino acid 52 of SEQ ID NO: 1. In another embodiment, the Group H nuclear receptor ligand binding domain is encoded by a polynucleotide comprising codon mutations that results in substitution of an isoleucine residue at a position equivalent or analogous to amino acid 107 of SEQ ID NO: 1, a glutamic acid residue at a position equivalent or analogous to amino acid 127 of SEQ ID NO: 1 and insertion of a glycine residue at a position equivalent or analogous to amino acid 259 of SEQ ID NO: 1. In a preferred embodiment, the Group H nuclear receptor ligand binding domain is from an ecdysone receptor.

In a specific embodiment, the Group H nuclear receptor ligand binding domain comprising a substitution mutation is an ecdysone receptor ligand binding domain comprising a substitution mutation encoded by a polynucleotide comprising a codon mutation that results in a substitution mutation selected from the group consisting of F48Y, F48W, F48L, F48N, F48R, F48K, I51M, I51N, I51L, T52M, T52V, T52L, T52E, T52P, T52R, T52W, T52G, T52Q, M54W, M54T, M92L, M92E, R95H, R95M, R95W, V96L, V96W, V96S, V96E, F109W, F109P, F109L, F109M, F109N, A110E, A110N, A110W, N119F, Y120W, Y120M, M125P, M125R, M125E, M125L, M125C, M125W, M125G, M125I, M125N, M125S, M125V, V128F, L132M, L132N, L132V, L132E, M219K, M219W, M219Y, M219A, L223K, L223R, L223Y, L234M, L234I, L234R, L234W, W238P, W238E, W238Y, W238M, W238L, N119F/V96T, V128F/A110P, T52V/A110P, V107I/Y127E/T52V, and V107I/Y127E/A110P substitution mutation of SEQ ID NO: 1. In another specific embodiment, the Group H nuclear receptor ligand binding domain comprising a substitution mutation is an ecdysone receptor ligand binding domain comprising a substitution mutation encoded by a polynucleotide comprising a codon mutation that results in substitution mutation V107I/Y127E of SEQ ID NO: 1, which further comprises insertion mutation G259 of SEQ ID NO: 1 (V107I/Y127E/G259).

In another specific embodiment, the Group H nuclear receptor ligand binding domain comprising a substitution mutation is an ecdysone receptor ligand binding domain polypeptide comprising a substitution mutation encoded by a polynucleotide that hybridizes to a polynucleotide comprising a codon mutation that results in a substitution mutation selected from the group consisting of F48Y, F48W, F48L, F48N, F48R, F48K, I51M, I51N, I51L, T52M, T52V, T52L, T52E, T52P, T52R, T52W, T52G, T52Q, M54W, M54T, M92L, M92E, R95H, R95M, R95W, V96L, V96W, V96S, V96E, F109W, F109P, F109L, F109M, F109N, A110E, A110N, A110W, N119F, Y120W, Y120M, M125P, M125R, M125E, M125L, M125C, M125W, M125G, M125I, M125N, M125S, M125V, V128F, L132M, L132N, L132V, L132E, M219K, M219W, M219Y, M219A, L223K, L223R, L223Y, L234M, L234I, L234R, L234W, W238P, W238E, W238Y, W238M, W238L, N119F/V96T, V128F/A110P, T52V/A110P, V107I/Y127E/T52V, and V107I/Y127E/A110P of SEQ ID NO: 1 under hybridization conditions comprising a hybridization step in less than 500 mM salt and at least 37 degrees Celsius, and a washing step in 2×SSPE at least 63 degrees Celsius. In a preferred embodiment, the hybridization conditions comprise less than 200 mM salt and at least 37 degrees Celsius for the hybridization step. In another preferred embodiment, the hybridization conditions comprise 2×SSPE and 63 degrees Celsius for both the hybridization and washing steps.

In another specific embodiment, the Group H nuclear receptor ligand binding domain comprises a substitution mutation at a position equivalent or analogous to a) amino acid residue 48, 51, 52, 54, 92, 95, 96, 109, 110, 119, 120, 125, 128, 132, 219, 223, 234, or 238 of SEQ ID NO: 1, b) amino acid residues 96 and 119 of SEQ ID NO: 1, c) amino acid residues 110 and 128 of SEQ ID NO: 1, d) amino acid residues 52 and 110 of SEQ ID NO: 1, e) amino acid residues 107, 110, and 127 of SEQ ID NO: 1, or f) amino acid residues 52, 107 and 127 of SEQ ID NO: 1. In another embodiment, the Group H nuclear receptor ligand binding domain comprises substitution mutations that results in substitution mutation at a position equivalent or analogous to amino acid residues 107 and 127 and insertion of amino acid residue 259 of SEQ ID NO: 1. In a preferred embodiment, the Group H nuclear receptor ligand binding domain is from an ecdysone receptor.

Preferably, the Group H nuclear receptor ligand binding domain comprises a substitution of a) an asparagine, arginine, tyrosine, tryptophan, leucine or lysine residue at a position equivalent to analogous to amino acid residue 48 of SEQ ID NO: 1, b) a methionine, asparagine or leucine residue at a position equivalent or analogous to amino acid residue 51 of SEQ ID NO: 1, c) a leucine, proline, methionine, arginine, tryptophan, glycine, glutamine or glutamic acid residue at a position equivalent or analogous to amino acid residue 52 of SEQ ID NO: 1, d) a tryptophan or threonine residue at a position equivalent or analogous to amino acid 54 of SEQ ID NO: 1, e) a leucine or glutamic acid residue at a position equivalent or analogous to amino acid 92 of SEQ ID NO: 1, f) a histidine, methionine or tryptophan residue at a position equivalent or analogous to amino acid residue 95 of SEQ ID NO: 1, g) a leucine, serine, glutamic acid or tryptophan residue at a position equivalent or analogous to amino acid residue 96 of SEQ ID NO: 1, h) a tryptophan, proline, leucine, methionine or asparagine at a position equivalent or analogous to amino acid 109 of SEQ ID NO: 1, i) a glutamic acid, tryptophan or asparagine residue at a position equivalent or analogous to amino acid residue 110 of SEQ ID NO: 1, j) a phenylalanine residue at a position equivalent or analogous to amino acid 119 of SEQ ID NO: 1, k) a tryptophan or methionine residue at a position equivalent or analogous to amino acid 120 of SEQ ID NO: 1, l) a glutamic acid, proline, leucine, cysteine, tryptophan, glycine, isoleucine, asparagine, serine, valine or arginine residue at a position equivalent or analogous to amino acid 125 of SEQ ID NO: 1, m) a phenylalanine residue at a position equivalent or analogous to amino acid 128 of SEQ ID NO: 1, n) a methionine, asparagine, glutamic acid or valine residue at a position equivalent or analogous to amino acid 132 of SEQ ID NO: 1, o) an alanine, lysine, tryptophan or tyrosine residue at a position equivalent or analogous to amino acid residue 219 of SEQ ID NO: 1, p) a lysine, arginine or tyrosine residue at a position equivalent or analogous to amino acid residue 223 of SEQ ID NO: 1, q) a methionine, arginine, tryptophan or isoleucine residue at a position equivalent or analogous to amino acid 234 of SEQ ID NO: 1, r) a proline, glutamic acid, leucine, methionine or tyrosine residue at a position equivalent or analogous to amino acid 238 of SEQ ID NO: 1, s) a phenylalanine residue at a position equivalent or analogous to amino acid 119 of SEQ ID NO: 1 and a threonine residue at a position equivalent or analogous to amino acid 96 of SEQ ID NO: 1, t) a proline residue at a position equivalent or analogous to amino acid 110 of SEQ ID NO: 1 and a phenylalanine residue at a position equivalent or analogous to amino acid 128 of SEQ ID NO: 1, u) a valine residue at a position equivalent or analogous to amino acid 52 of SEQ ID NO: 1 and a proline residue at a position equivalent or analogous to amino acid 110 of SEQ ID NO: 1, v) an isoleucine residue at a position equivalent or analogous to amino acid 107 of SEQ ID NO: 1, a glutamic acid residue at a position equivalent or analogous to amino acid 127 of SEQ ID NO: 1 and a proline residue at a position equivalent or analogous to amino acid 110 of SEQ ID NO: 1, or w) an isoleucine residue at a position equivalent or analogous to amino acid 107 of SEQ ID NO: 1, a glutamic acid residue at a position equivalent or analogous to amino acid 127 of SEQ ID NO: 1 and a valine residue at a position equivalent or analogous to amino acid 52 of SEQ ID NO: 1. In another embodiment, the Group H nuclear receptor ligand binding domain comprises a substitution of an isoleucine residue at a position equivalent or analogous to amino acid 107 of SEQ ID NO: 1, a glutamic acid residue at a position equivalent or analogous to amino acid 127 of SEQ ID NO: 1 and insertion of a glycine residue at a position equivalent or analogous to amino acid 259 of SEQ ID NO: 1. In a preferred embodiment, the Group H nuclear receptor ligand binding domain is from an ecdysone receptor.

In another specific embodiment, the Group H nuclear receptor ligand binding domain comprising a substitution mutation is an ecdysone receptor ligand binding domain polypeptide comprising a substitution mutation, wherein the substitution mutation is selected from the group consisting of F48Y, F48W, F48L, F48N, F48R, F48K, I51M, I51N, I51L, T52M, T52V, T52L, T52E, T52P, T52R, T52W, T52G, T52Q, M54W, M54T, M92L, M92E, R95H, R95M, R95W, V96L, V96W, V96S, V96E, F109W, F109P, F109L, F109M, F109N, A110E, A110N, A110W, N119F, Y120W, Y120M, M125P, M125R, M125E, M125L, M125C, M125W, M125G, M125I, M125N, M125S, M125V, V128F, L132M, L132N, L132V, L132E, M219E, M219W, M219Y, M219A, L223K, L223R, L223Y, L234M, L234I, L234R, L234W, W238P, W238E, W238Y, W238M, W238L, N119F/V96T, T52V/A110P, V128F/A110P, V107I/Y127E/T52V, and V107I/Y127E/A110P substitution mutation of SEQ ID NO: 1. In another specific embodiment, the Group H nuclear receptor ligand binding domain comprising a substititution mutation is an ecdysone receptor ligand binding domain polypeptide comprising substitution mutation V107I/Y127E of SEQ ID NO: 1, which further comprises insertion mutation G259 of SEQ ID NO: 1 (V107I/Y127E/G259).

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a Group H nuclear receptor member DBD, a steroid/thyroid hormone nuclear receptor superfamily member DBD, or a bacterial LacZ DBD. More preferably, the DBD is an EcR DBD [SEQ ID NO: 4 (polynucleotide) or SEQ ID NO: 5 (polypeptide)], a GAL4 DBD [SEQ ID NO: 6 (polynucleotide) or SEQ ID NO: 7 (polypeptide)], or a LexA DBD [(SEQ ID NO: 8 (polynucleotide) or SEQ ID NO: 9 (polypeptide)].

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), or an analog, combination, or modification thereof. In a specific embodiment, the AD is a synthetic or chimeric AD, or is obtained from an EcR, a glucocorticoid receptor, VP16, GAL4, NF-kB, or B42 acidic activation domain AD. Preferably, the AD is an EcR AD [SEQ ID NO: 10 (polynucleotide) or SEQ ID NO: 11 (polypeptide)], a VP16 AD [SEQ ID NO: 12 (polynucleotide) or SEQ ID NO: 13 (polypeptide)], a B42 AD [SEQ ID NO: 14 (polynucleotide) or SEQ ID NO: 15 (polypeptide)], or a p65 AD [SEQ ID NO: 16 (polynucleotide) or SEQ ID NO: 17 (polypeptide)].

In a specific embodiment, the gene expression cassette encodes a hybrid polypeptide comprising either a) a DNA-binding domain encoded by a polynucleotide comprising a nucleic acid sequence of SEQ ID NO: 4, SEQ ID NO: 6, or SEQ ID NO: 8, or b) a transactivation domain encoded by a polynucleotide comprising a nucleic acid sequence of SEQ ID NO: 10, SEQ ID NO: 12, SEQ ID NO: 14, or SEQ ID NO: 16; and a Group H nuclear receptor ligand binding domain comprising a substitution mutation encoded by a polynucleotide according to the invention. Preferably, the Group H nuclear receptor ligand binding domain comprising a substitution mutation is an ecdysone receptor ligand binding domain comprising a substitution mutation encoded by a polynucleotide according to the invention.

In another specific embodiment, the gene expression cassette encodes a hybrid polypeptide comprising either a) a DNA-binding domain comprising an amino acid sequence of SEQ ID NO: 5, SEQ ID NO: 7, or SEQ ID NO: 9, or b) a transactivation domain comprising an amino acid sequence of SEQ ID NO: 11, EQ ID NO: 13, SEQ ID NO: 15, or SEQ ID NO: 17; and a Group H nuclear receptor ligand binding domain comprising a substitution mutation according to the invention. Preferably, the Group H nuclear receptor ligand binding domain comprising a substitution mutation is an ecdysone receptor ligand binding domain comprising a substitution mutation according to the invention.

The present invention also provides a gene expression cassette comprising: i) a response element comprising a domain recognized by a polypeptide comprising a DNA binding domain; ii) a promoter that is activated by a polypeptide comprising a transactivation domain; and iii) a gene whose expression is to be modulated.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4 RE"), LexA, a Group H nuclear receptor RE, a steroid/thyroid hormone nuclear receptor RE, or a synthetic RE that recognizes a synthetic DNA binding domain. Preferably, the RE is an ecdysone response element (EcRE) comprising a polynucleotide sequence of SEQ ID NO: 18, a GAL4RE comprising a polynucleotide sequence of SEQ ID NO: 19, or a LexA RE (operon, "op") comprising a polynucleotide sequence of SEQ ID NO: 20 ("2XLexAopRE").

A steroid/thyroid hormone nuclear receptor DNA binding domain, activation domain or response element according to the invention may be obtained from a steroid/thyroid hormone nuclear receptor selected from the group consisting of thyroid hormone receptor α (TRα), thyroid receptor 1 (c-erbA-1), thyroid hormone receptor β (TRβ), retinoic acid receptor α (RARα), retinoic acid receptor β (RARβ, HAP), retinoic acid receptor γ (RARγ), retinoic acid recetor gamma-like (RARD), peroxisome proliferator-activated receptor α (PPARα), peroxisome proliferator-activated receptor β (PPARβ), peroxisome proliferator-activated receptor β (PPARβ, NUC-1), peroxisome proliferator-activator related receptor (FFAR), peroxisome proliferator-activated receptor γ (PPARγ), orphan receptor encoded by non-encoding strand of thyroid hormone receptor α (REVERBα), v-erb A related receptor (EAR-1), v-erb related receptor (EAR-1A), γ), orphan receptor encoded by non-encoding strand of thyroid hormone receptor β (REVERBβ), v-erb related receptor (EAR-1β), orphan nuclear recptor BD73 (BD73), rev-erbA-related receptor (RVR), zinc finger protein 126 (HZF2), ecdysone-inducible protein E75 (E75), ecdysone-inducible protein E78 (E78), Drosophila receptor 78 (DR-78), retinoid-related orphan receptor α (RORα), retinoid Z receptor α (RZRα), retinoid related orphan receptor β (RORβ), retinoid Z receptor β (RZRβ), retinoid-related orphan receptor γ (RORγ), retinoid Z receptor γ (RZRγ), retinoid-related orphan receptor (TOR), hormone receptor 3 (HR-3), Drosophila hormone receptor 3 (DHR-3), Manduca hormone receptor (MHR-3), Galleria hormone receptor 3 (GHR-3), C. elegans nuclear receptor 3 (CNR-3), Choristoneura hormone receptor 3 (CHR-3), C. elegans nuclear receptor 14 (CNR-14), ecdysone receptor (ECR), ubiquitous receptor (UR), orphan nuclear receptor (OR-1), NER-1, receptor-interacting protein 15 (RIP-15), liver X receptor β (LXRβ), steroid hormone receptor like protein (RLD-1), liver X receptor (LXR), liver X receptor α (LXRα), farnesoid X receptor (FXR), receptor-interacting protein 14 (RIP-14), HRR-1, vitamin D receptor (VDR), orphan nuclear receptor (ONR-1), pregnane X receptor (PXR), steroid and xenobiotic receptor (SXR), benzoate X receptor (BXR), nuclear receptor (MB-67), constitutive androstane receptor 1 (CAR-1), constitutive androstane receptor α (CARα), constitutive androstane receptor 2 (CAR-2), constitutive androstane receptor β (CARβ), Drosophila hormone receptor 96 (DHR-96), nuclear hormone receptor 1 (NHR-1), hepatocyte nuclear factor 4 (HNF-4), hepatocyte nuclear factor 4G (HNF-4G), hepatocyte nuclear factor 4B (HNF-4B), hepatocyte nuclear factor 4D (HNF-4D, DHNF-4), retinoid X receptor α (RXRα), retinoid X receptor β (RXRβ), H-2 region II binding protein (H-2RIIBP), nuclear receptor co-regulator-1 (RCoR-1), retinoid X receptor γ (RXRγ), Ultraspiracle (USP), 2C1 nuclear receptor, chorion factor 1 (CF-1), testicular receptor 2 (TR-2), testicular receptor 2-11 (TR2-11), testicular receptor 4 (TR4), TAK-1, Drosophila hormone receptor (DHR78), Tailless (TLL), tailless homolog (TLX), XTLL, chicken ovalbumin upstream promoter transcription factor I (COUP-TFI), chicken ovalbumin upstream promoter transcription factor A (COUP-TFA), EAR-3, SVP-44, chicken ovalbumin upstream promoter transcription factor II (COUP-TFII), chicken ovalbumin upstream promoter transcription factor B (COUP-TFB), ARP-1, SVP-40, SVP, chicken ovalbumin upstream promoter transcription factor III (COUP-TFIII), chicken ovalbumin upstream promoter transcription factor G (COUP-TFG), SVP-46, EAR-2, estrogen receptor α (ERα), estrogen receptor β (ERβ), estrogen related receptor 1 (ERR1), estrogen related receptor α (ERRα), estrogen related receptor 2 (ERR2), estrogen related receptor β (ERRβ), glucocorticoid receptor (GR), mineralocorticoid receptor (MR), progesterone receptor (PR), androgen receptor (AR), nerve growth factor induced gene B (NGFI-B), nuclear receptor similar to Nur-77 (TRS), N10, Orphan receptor (NUR-77), Human early response gene (NAK-1), Nurr related factor 1 (NURR-1), a human immediate-early response gene (NOT), regenerating liver nuclear receptor 1 (RNR-1), hematopoietic zinc finger 3 (HZF-3), Nur rekated protein-1 (TINOR), Nuclear orphan receptor 1 (NOR-1), NOR1 related receptor (MI-NOR), Drosophila hormone receptor 38 (DHR-38), C. elegans nuclear receptor 8 (CNR-8), C48D5, steroidogenic factor 1 (SF1), endozepine-like peptide (ELP), fushi tarazu factor 1 (FTZ-F1), adrenal 4 binding protein (AD4BP), liver receptor homolog (LRH-1), Ftz-F1-related orphan receptor A (xFFrA), Ftz-F1-related orphan receptor B (xFFrB), nuclear receptor related to LRH-1 (FFLR), nuclear receptor related to LRH-1 (PHR), fetoprotein transcriptin factor (FTF), germ cell nuclear factor (GCNFM), retinoid receptor-related testis-associated receptor (RTR), knirps (KNI), knirps related (KNRL), Embryonic gonad (EGON), Drosophila gene for ligand dependent nuclear receptor (EAGLE), nuclear receptor similar to trithorax (ODR7), Trithorax, dosage sensitive sex reversal adrenal hypoplasia congenita critical region chromosome X gene (DAX-1), adrenal hypoplasia congenita and hypogonadotropic hypogonadism (AHCH), and short heterodimer partner (SHP).

For purposes of this invention, nuclear receptors and Group H nuclear receptors also include synthetic and chimeric nuclear receptors and Group H nuclear receptors and their homologs.

Genes of interest for use in Applicants' gene expression cassettes may be endogenous genes or heterologous genes. Nucleic acid or amino acid sequence information for a desired gene or protein can be located in one of many public access databases, for example, GENBANK, EMBL, Swiss-Prot, and PIR, or in many biology-related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for use in Applicants' gene expression cassettes include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Polynucleotides of the Invention

The novel nuclear receptor-based inducible gene expression system of the invention comprises at least one gene expression cassette comprising a polynucleotide that encodes a Group H nuclear receptor ligand binding domain comprising a substitution mutation. These gene expression cassettes, the polynucleotides they comprise, and the polypeptides they encode are useful as components of a nuclear receptor-based gene expression system to modulate the expression of a gene within a host cell.

Thus, the present invention provides an isolated polynucleotide that encodes a Group H nuclear receptor ligand binding domain comprising a substitution mutation.

In a specific embodiment, the Group H nuclear receptor ligand binding domain is encoded by a polynucleotide comprising a codon mutation that results in a substitution of an amino acid residue at a position equivalent or analogous to a) amino acid residue 48, 51, 52, 54, 92, 95, 96, 109, 110, 119, 120, 125, 128, 132, 219, 223, 234, or 238 of SEQ ID NO: 1, b) amino acid residues 96 and 119 of SEQ ID NO: 1, c) amino acid residues 110 and 128 of SEQ ID NO: 1, d) amino acid residues 52 and 110 of SEQ ID NO: 1, e) amino acid residues 107, 110, and 127 of SEQ ID NO: 1, or f) amino acid residues 52, 107 and 127 of SEQ ID NO: 1. In another embodiment, the Group H nuclear receptor ligand binding domain is encoded by a polynucleotide comprising codon mutations that results in substitution of amino acid residues at positions equivalent or analogous to amino acid residues 107 and 127, and insertion of amino acid 259 of SEQ ID NO: 1. In a preferred embodiment, the Group H nuclear receptor ligand binding domain is from an ecdysone receptor.

In another specific embodiment, the Group H nuclear receptor ligand binding domain is encoded by a polynucleotide comprising a codon mutation that results in a substitution of a) an asparagine, arginine, tyrosine, tryptophan, leucine or lysine residue at a position equivalent to analogous to amino acid residue 48 of SEQ ID NO: 1, b) a methionine, asparagines or leucine residue at a position equivalent or analogous to amino acid residue 51 of SEQ ID NO: 1, c) a leucine, proline, methionine, arginine, tryptophan, glycine, glutamine or glutamic acid residue at a position equivalent or analogous to amino acid residue 52 of SEQ ID NO: 1, d) a tryptophan or threonine at a position equivalent or analogous to amino acid 54 of SEQ ID NO: 1, e) a leucine or glutamic acid at a position equivalent or analogous to amino acid 92 of SEQ ID NO: 1, f) a histidine, methionine or tryptophan residue at a position equivalent or analogous to amino acid residue 95 of SEQ ID NO: 1, g) a leucine, serine, glutamic acid or tryptophan residue at a position equivalent or analogous to amino acid residue 96 of SEQ ID NO: 1, h) a tryptophan, proline, leucine, methionine or asparagine at a position equivalent or analogous to amino acid 109 of SEQ ID NO: 1, i) a glutamic acid, tryptophan or asparagine residue at a position equivalent or analogous to amino acid residue 110 of SEQ ID NO: 1, j) a phenylalanine at a position equivalent or analogous to amino acid 119 of SEQ ID NO: 1, k) a tryptophan or methionine at a position equivalent or analogous to amino acid 120 of SEQ ID NO: 1, l) a glutamic acid, proline, leucine, cysteine, tryptophan, glycine, isoleucine, asparagine, serine, valine or arginine at a position equivalent or analogous to amino acid 125 of SEQ ID NO: 1, m) a phenylalanine at a position equivalent or analogous to amino acid 128 of SEQ ID NO: 1, n) a methionine, asparagine, glutamic acid or valine at a position equivalent or analogous to amino acid 132 of SEQ ID NO: 1, o) an alanine, lysine, tryptophan or tyrosine residue at a position equivalent or analogous to amino acid residue 219 of SEQ ID NO: 1, p) a lysine, arginine or tyrosine residue at a position equivalent or analogous to amino acid residue 223 of SEQ ID NO: 1, q) a methionine, arginine, tryptophan or isoleucine at a position equivalent or analogous to amino acid 234 of SEQ ID NO: 1, r) a proline, glutamic acid, leucine, methionine or tyrosine at a position equivalent or analogous to amino acid 238 of SEQ ID NO: 1, s) a phenylalanine at a position equivalent or analogous to amino acid 119 of SEQ ID NO: 1 and a threonine at a position equivalent or analogous to amino acid 96 of SEQ ID NO: 1, t) a proline at a position equivalent or analogous to amino acid 110 of SEQ ID NO: 1 and a phenylalanine at a position equivalent or analogous to amino acid 128 of SEQ ID NO: 1, u) a valine residue at a position equivalent or analogous to amino acid 52 of SEQ ID NO: 1 and a proline residue residue at a position equivalent or analogous to amino acid 110 of SEQ ID NO: 1, v) an isoleucine at a position equivalent or analogous to amino acid 107 of SEQ ID NO: 1, a glutamic acid at a position equivalent or analogous to amino acid 127 of SEQ ID NO: 1 and a proline at a position equivalent or analogous to amino acid 110 of SEQ ID NO: 1, or w) an isoleucine at a position equivalent or analogous to amino acid 107 of SEQ ID NO: 1, a glutamic acid at a position equivalent or analogous to amino acid 127 of SEQ ID NO: 1 and a valine at a position equivalent or analogous to amino acid 52 of SEQ ID NO: 1. In another embodiment, the Group H nuclear receptor ligand binding domain is encoded by a polynucleotide comprising codon mutations that results in substitution of an isoleucine residue at a position equivalent or analogous to amino acid 107 of SEQ ID NO: 1, a glutamic acid residue at a position equivalent or analogous to amino acid 127 of SEQ ID NO: 1 and insertion of a glycine residue at a position equivalent or analogous to amino acid 259 of SEQ ID NO: 1. In a preferred embodiment, the Group H nuclear receptor ligand binding domain is from an ecdysone receptor.

In another specific embodiment, the Group H nuclear receptor ligand binding domain comprising a substitution mutation is an ecdysone receptor ligand binding domain comprising a substitution mutation encoded by a polynucleotide comprising a codon mutation that results in a substitution mutation selected from the group consisting of F48Y, F48W, F48L, F48N, F48R, F48K, I51M, I51N, I51L, T52M, T52V, T52L, T52E, T52P, T52R, T52W, T52G, T52Q, M54W, M54T, M92L, M92E, R95H, R95M, R95W, V96L, V96W, V96S, V96E, F109W, F109P, F109L, F109M, F109N, A110E, A110N, A110W, N119F, Y120W, Y120M, M125P, M125R, M125E, M125L, M125C, M125W, M125G, M125I, M125N, M125S, M125V, V128F, L132M, L132N, L132V, L132E, M219K, M219W, M219Y, M219A, L223K, L223R, L223Y, L234M, L234I, L234R, L234W, W238P, W238E, W238Y, W238M, W238L, N119F/V96T, V128F/A110P, T52V/A110P, V107I/Y127E/T52V, and V107I/Y127E/A110P substitution mutation of SEQ ID NO: 1. In another embodiment, the Group H nuclear receptor ligand binding domain comprising a substititution mutation is an ecdysone receptor ligand binding domain comprising a substitution mutation encoded by a polynucleotide comprising a codon mutation that results in substitution mutation V107I/Y127E of SEQ ID NO: 1, which further comprises insertion mutation G259 of SEQ ID NO: 1 (V107I/Y127E/G259).

In another specific embodiment, the Group H nuclear receptor ligand binding domain comprising a substitution mutation is an ecdysone receptor ligand binding domain comprising a substitution mutation encoded by a polynucleotide that hybridizes to a polynucleotide comprising a codon mutation that results in a substitution mutation selected from the group consisting of F48Y, F48W, F48L, F48N, F48R, F48K, I51M, I51N, I51L, T52M, T52V, T52L, T52E, T52P, T52R, T52W, T52G, T52Q, M54W, M54T, M92L, M92E, R95H, R95M, R95W, V96L, V96W, V96S, V96E, F109W, F109P, F109L, F109M, F109N, A110E, A110N, A110W, N119F, Y120W, Y120M, M125P, M125R, M125E, M125L, M125C, M125W, M125G, M125I, M125N, M125S, M125V, V128F, L132M, L132N, L132V, L132E, M219K, M219W, M219Y, M219A, L223K, L223R, L223Y, L234M, L234I, L234R, L234W, W238P, W238E, W238Y, W238M, W238L, N119F/V96T, V128F/A110P, T52V/A110P, V107I/Y127E/T52V, and V107I/Y127E/A110P of SEQ ID NO: 1 under hybridization conditions comprising a hybridization step in less than 500 mM salt and at least 37 degrees Celsius, and a washing step in 2×SSPE at least 63 degrees Celsius. In a preferred embodiment, the hybridization conditions comprise less than 200 mM salt and at least 37 degrees Celsius for the hybridization step. In another preferred embodiment, the hybridization conditions comprise 2×SSPE and 63 degrees Celsius for both the hybridization and washing steps.

The present invention also provides an isolated polynucleotide that encodes a polypeptide selected from the group consisting of a) a polypeptide comprising a transactivation domain, a DNA-binding domain, and a Group H nuclear receptor ligand binding domain comprising a substitution mutation according to the invention; b) a polypeptide comprising a DNA-binding domain and a Group H nuclear receptor ligand binding domain comprising a substitution mutation according to the invention; and c) a polypeptide comprising a transactivation domain and a Group H nuclear receptor ligand binding domain comprising a substitution mutation according to the invention.

In a specific embodiment, the isolated polynucleotide encodes a hybrid polypeptide selected from the group consisting of a) a hybrid polypeptide comprising a transactivation domain, a DNA-binding domain, and a Group H nuclear receptor ligand binding domain comprising a substitution mutation according to the invention; b) a hybrid polypeptide comprising a DNA-binding domain and a Group H nuclear receptor ligand binding domain comprising a substitution mutation according to the invention; and c) a hybrid polypeptide comprising a transactivation domain and a Group H nuclear receptor ligand binding domain comprising a substitution mutation according to the invention.

The present invention also relates to an isolated polynucleotide encoding a Group H nuclear receptor ligand binding domain comprising a substitution mutation, wherein the substitution mutation affects ligand binding activity or ligand sensitivity of the Group H nuclear receptor ligand binding domain.

In another specific embodiment, the present invention relates to an isolated polynucleotide encoding a Group H nuclear receptor ligand binding domain comprising a substitution mutation, wherein the substitution mutation reduces non-ecdysteroid diacylhydrazine binding activity or non-ecdysteroid diacylhydrazine sensitivity of the Group H nuclear receptor ligand binding domain. Preferably, the isolated polynucleotide comprises a codon mutation that results in a substitution of an amino acid residue at a position equivalent or analogous to amino acid residue 48, 51, 52, 54, 92, 95, 96, 109, 120, 125, 219, 223, 234 or 238 of SEQ ID NO: 1. More preferably, the isolated polynucleotide comprises a codon mutation that results in a substitution of a) an asparagine residue at a position equivalent or analogous to amino acid residue 48 or 109 of SEQ ID NO: 1, b) a leucine residue at a position equivalent or analogous to amino acid residue 51, 92, 96 or 238 of SEQ ID NO: 1, c) a glutamic acid residue at a position equivalent or analogous to amino acid residue 52, 92, 96, 125 or 238 of SEQ ID NO: 1, d) a tryptophan residue at a position equivalent or analogous to amino acid residue 54, 95, 96, 120, 219 or 234 of SEQ ID NO: 1, e) a methionine residue at a position equivalent or analogous to amino acid residue 51, 52, 120, 234 or 238 of SEQ ID NO: 1, f) an alanine residue at a position equivalent or analogous to amino acid residue 219 of SEQ ID NO: 1, g) a lysine residue at a position equivalent or analogous to amino acid residue 48, 219 or 223 of SEQ ID NO: 1, h) an isoleucine, arginine or tryptophan residue at a position equivalent or analogous to amino acid residue 234 of SEQ ID NO: 1, i) a tyrosine residue at a position equivalent or analogous to amino acid residue 219 or 238 of SEQ ID NO: 1, j) a valine residue at a position equivalent or analogous to amino acid residue 125 of SEQ ID NO: 1, k) a glycine or glutamine residue at a position equivalent or analogous to amino acid residue 52 of SEQ ID NO: 1 or l) an arginine residue at a position equivalent or analogous to amino acid residue 52 or 223 of SEQ ID NO: 1. Even more preferably, the isolated polynucleotide comprises a codon mutation that results in a substitution mutation of F48N, F48K, I51L, I51M, T52E, T52M, T52R, T52G, T52Q, M54W, M92L, M92E, R95W, V96W, V96E, V96L, F109N, Y120M, Y120W, M125E, M125V, M219A, M219K, M219W, M219Y, L223K, L223R, L234M, L234I, L234R, L234W, W238E, W238Y, W238L or W238M of SEQ ID NO: 1.

In addition, the present invention also relates to an isolated polynucleotide encoding a Group H nuclear receptor ligand binding domain comprising a substitution mutation, wherein the substitution mutation enhances ligand binding activity or ligand sensitivity of the Group H nuclear receptor ligand binding domain.

In a specific embodiment, the present invention relates to an isolated polynucleotide encoding a Group H nuclear receptor ligand binding domain comprising a substitution mutation, wherein the substitution mutation generally enhances ecdysteroid binding activity or ecdysteroid sensitivity of the Group H nuclear receptor ligand binding domain. Preferably, the isolated polynucleotide comprises a codon mutation that results in a substitution of an amino acid residue at a position equivalent or analogous to a) amino acid residue 96 of SEQ ID NO: 1 or b) amino acid residues 96 and 119 of SEQ ID NO: 1. More preferably, the isolated polynucleotide comprises a codon mutation that results in a substitution of a) a serine residue at a position equivalent or analogous to amino acid residue 96 of SEQ ID NO: 1 or b) a threonine residue at a position equivalent or analogous to amino acid residue 96 of SEQ ID NO: 1 and a phenylalanine residue at a position equivalent or analogous to amino acid residue 119 of SEQ ID NO: 1. Even more preferably, the isolated polynucleotide comprises a codon mutation that results in a substitution mutation of V96T or N119F/V96T of SEQ ID NO: 1.

In another specific embodiment, the present invention relates to an isolated polynucleotide encoding a Group H nuclear receptor ligand binding domain comprising a substitution mutation, wherein the substitution mutation generally enhances non-ecdysteroid diacylhydrazine binding activity or non-ecdysteroid diacylhydrazine sensitivity of the Group H nuclear receptor ligand binding domain. Preferably, the isolated polynucleotide comprises a codon mutation that results in a substitution of an amino acid residue at a position equivalent or analogous to a) amino acid residue 48, 52, 54, 109, 110, 125, 132 or 223 of SEQ ID NO: 1 or b) amino acid residues 52 and 110 of SEQ ID NO: 1. More preferably, the isolated polynucleotide comprises a codon mutation that results in a substitution of a) a tyrosine, tryptophan, arginine or leucine residue at a position equivalent or analogous to amino acid residue 48 of SEQ ID NO: 1, b) a leucine residue at a position equivalent or analogous to amino acid residue 52 of SEQ ID NO: 1, c) a threonine residue at a position equivalent or analogous to amino acid residue 54 of SEQ ID NO: 1, d) methionine residue at a position equivalent or analogous to amino acid residue 109 of SEQ ID NO: 1, e) a proline, glutamic acid or asparagine residue at a position equivalent or analogous to amino acid residue 110 of SEQ ID NO: 1, f) an isoleucine, asparagine or glycine residue at a position equivalent or analogous to amino acid residue 125 of SEQ ID NO: 1, g) a glutamic acid residue at a position equivalent or analogous to amino acid residue 132 of SEQ ID NO: 1, h) a tyrosine residue at a position equivalent or analogous to amino acid residue 223 of SEQ ID NO: 1 or i) a valine residue at a position equivalent or analogous to amino acid 52 of SEQ ID NO: 1 and a proline residue at a position equivalent or analogous to amino acid 110 of SEQ ID NO: 1. Even more preferably, the isolated polynucleotide comprises a codon mutation that results in a substitution mutation of F48Y, F48W, F48L, F48R, T52L, M54T, F109M, A110P, A110E, A110N, M125I, M125G, M125N, L132E, L223Y or T52V/A110P of SEQ ID NO: 1.

In another specific embodiment, the present invention relates to an isolated polynucleotide encoding a Group H nuclear receptor ligand binding domain comprising a substitution mutation, wherein the substitution mutation generally enhances non-ecdysteroid diacylhydrazine and non-ecdysteroid tetrahydroquinoline binding activity or non-ecdysteroid diacylhydrazine and non-ecdysteroid tetrahydroquinoline sensitivity of the Group H nuclear receptor ligand binding domain. Preferably, the isolated polynucleotide comprises a codon mutation that results in a substitution of a) amino acid residues at a position equivalent or analogous to amino acid residues 107 and 127 of SEQ ID NO: 1 or b) amino acid residues 107, 110 and 127 of SEQ ID NO: 1. More preferably, the isolated polynucleotide comprises a codon mutation that results in a substitution of a) an isoleucine residue at a position equivalent or analogous to amino acid residue 107 of SEQ ID NO: 1 and a glutamic acid residue at a position equivalent or analogous to amino acid residue 127 of SEQ ID NO: 1 or b) an isoleucine residue at a position equivalent or analogous to amino acid residue 107 of SEQ ID NO: 1, a proline residue at a position equivalent or analogous to amino acid residue 110 of SEQ ID NO: 1 and a glutamic acid residue at a position equivalent or analogous to amino acid residue 127 of SEQ ID NO: 1. Even more preferably, the isolated polynucleotide comprises a codon mutation that results in a substitution mutation of V107I/Y127E or V107I/Y127E/A110P of SEQ ID NO: 1.

In another specific embodiment, the present invention relates to an isolated polynucleotide encoding a Group H nuclear receptor ligand binding domain comprising a substitution mutation, wherein the substitution mutation generally enhances both ecdysteroid binding activity or ecdysteroid sensitivity and non-ecdysteroid diacylhydrazine binding activity or non-ecdysteroid diacylhydrazine sensitivity of the Group H ligand binding domain. Preferably, the isolated polynucleotide comprises a codon mutation that results in a substitution of an amino acid residue at a position equivalent or analogous to a) amino acid residue 109, 132 or W238P of SEQ ID NO: 1, b) amino acid residues 52, 107 and 127 of SEQ ID NO: 1 or c) amino acid residues 107 and 127 of SEQ ID NO: 1, and insertion of amino acid 259 of SEQ ID NO: 1. More preferably, the isolated polynucleotide comprises a codon mutation that results in a substitution of a) tryptophan residue at a position equivalent or analogous to amino acid residue 109 of SEQ ID NO: 1, b) a valine or methionine residue at a position equivalent or analogous to amino acid residue 132 of SEQ ID NO: 1, c) a proline residue at a position equivalent or analogous to amino acid residue 238 of SEQ ID NO: 1 d) an isoleucine residue at a position equivalent or analogous to amino acid residue 107 of SEQ ID NO: 1, a glutamic acid residue at a position equivalent or analogous to amino acid residue 127 of SEQ ID NO: 1 and a valine residue at a position equivalent or analogous to amino acid residue 132 of SEQ ID NO: 1 or e) an isoleucine residue at a position equivalent or analogous to amino acid 107 of SEQ ID NO: 1, a glutamic acid residue at a position equivalent or analogous to amino acid 127 of SEQ ID NO: 1 and insertion of a glycine residue at a position equivalent or analogous to amino acid 259 of SEQ ID NO: 1. Even more preferably, the isolated polynucleotide comprises a codon mutation that results in a substitution mutation of F109W, L132M, L132V, W238P, V107I/Y127E/T52V or V107I/Y127E/259G of SEQ ID NO: 1. In another embodiment, the isolated polynucleotide comprises a codon mutation that results in substitution mutation V107I/Y127E of SEQ ID NO: 1 further comprising insertion mutation G259 of SEQ ID NO: 1 (V107I/Y127E/G259).

In another specific embodiment, the present invention relates to an isolated polynucleotide encoding a Group H nuclear receptor ligand binding domain comprising a substitution mutation, wherein the substitution mutation generally enhances non-ecdysteroid tetrahydroquinoline binding activity or non-ecdysteroid tetrahydroquinoline sensitivity of the Group H nuclear receptor ligand binding domain. Preferably, the isolated polynucleotide comprises a codon mutation that results in a substitution of a) amino acid residue at a position equivalent or analogous to amino acid residues 110 or 128 of SEQ ID NO: 1 or b) amino acid residues at a position equivalent or analogous to amino acid residues 110 and 128 of SEQ ID NO: 1. More preferably, the isolated polynucleotide comprises a codon mutation that results in a substitution of a) a tryptophan residue at a position equivalent or analogous to amino acid residue 110 of SEQ ID NO: 1, b) a phenylalanine residue at a position equivalent or analogous to amino acid residue 128 of SEQ ID NO: 1 or c) a proline residue at a position equivalent or analogous to amino acid residue 110 of SEQ ID NO: 1 and a phenylalanine residue at a position equivalent or analogous to amino acid residue 128 of SEQ ID NO: 1. Even more preferably, the isolated polynucleotide comprises a codon mutation that results in a substitution mutation A110W, V128F or V128F/A110P of SEQ ID NO: 1.

In another specific embodiment, the present invention relates to an isolated polynucleotide encoding a Group H nuclear receptor ligand binding domain comprising a substitution mutation, wherein the substitution mutation differentially responds to non-ecdysteroid diacylhydrazine ligands. Preferably, the isolated polynucleotide comprises a codon mutation that results in a substitution of an amino acid residue at a position equivalent or analogous to amino acid residues 52, 95, 109, 125 or 132 of SEQ ID NO: 1. More preferably, the isolated polynucleotide comprises a codon mutation that results in a substitution of a) a proline residue at a position equivalent or analogous to amino acid residue 52 of SEQ ID NO: 1, b) a histidine or methionine residue residue at a position equivalent or analogous to amino acid residue 95 of SEQ ID NO: 1, c) a leucine residue at a position equivalent or analogous to amino acid residue 109 of SEQ ID NO: 1, d) a leucine, tryptophan, arginine, cysteine or proline residue at a position equivalent or analogous to amino acid residue 125 of SEQ ID NO: 1 or e) a methionine residue at a position equivalent or analogous to amino acid residue 132 of SEQ ID NO: 1. Even more preferably, the isolated polynucleotide comprises a codon mutation that results in a substitution mutation T52P, T52W, R95H, R95M, F109L, M125L, M125W, M125R, M125C, M125P or L132M of SEQ ID NO: 1.

In another specific embodiment, the present invention relates to an isolated polynucleotide encoding a Group H nuclear receptor ligand binding domain comprising a substitution mutation, wherein the substitution mutation differentially responds to non-ecdysteroid diacylhydrazine ligands. More preferably the isolated polynucleotide comprises a codon mutation that results in a substitution of a) a lysine or arginine residue at a position equivalent or analogous to amino acid residue 48 of SEQ ID NO: 1, b) a glycine, glutamine, methionine, arginine or tryptophan residue at a position equivalent or analogous to amino acid residue 52 of SEQ ID NO: 1, c) an isoleucine, glycine, asparagine, serine or valine residue at a position equivalent or analogous to amino acid residue 125 of SEQ ID NO: 1, d) a glutamic acid residue at a position equivalent or analogous to amino acid residue 132 of SEQ ID NO: 1, e) a lysine, tryptophan or tyrosine residue at a position equivalent or analogous to amino acid residue 219 of SEQ ID NO: 1, f) an arginine or tyrosine residue at a position equivalent or analogous to amino acid residue 223 of SEQ ID NO: 1 or g) leucine or methionine residue at a position equivalent or analogous to amino acid residue 238 of SEQ ID NO: 1. Even more preferably the isolated polynucleotide comprises a codon mutation that results in a substitution mutation F48K, F48R, T52G, T52Q, T52M, T52R, T52W, M125I, M125G, M125N, M125S, M125V, L132E, M219K, M219W, M219Y, L223R, L223Y, W238L or W238M of SEQ ID NO: 1.

In addition, the present invention relates to an expression vector comprising a polynucleotide according the invention, operatively linked to a transcription regulatory element. Preferably, the polynucleotide encoding a nuclear receptor ligand binding domain comprising a substitution mutation is operatively linked with an expression control sequence permitting expression of the nuclear receptor ligand binding domain in an expression competent host cell. The expression control sequence may comprise a promoter that is functional in the host cell in which expression is desired. The vector may be a plasmid DNA molecule or a viral vector. Preferred viral vectors include retrovirus, adenovirus, adeno-associated virus, herpes virus, and vaccinia virus. The invention further relates to a replication defective recombinant virus comprising in its genome, the polynucleotide encoding a nuclear receptor ligand binding domain comprising a substitution mutation as described above. Thus, the present invention also relates to an isolated host cell comprising such an expression vector, wherein the transcription regulatory element is operative in the host cell.

The present invention also relates to an isolated polypeptide encoded by a polynucleotide according to the invention.

Polypeptides of the Invention

The novel nuclear receptor-based inducible gene expression system of the invention comprises at least one gene expression cassette comprising a polynucleotide that encodes a polypeptide comprising a Group H nuclear receptor ligand binding domain comprising a substitution mutation. Thus, the present invention also provides an isolated polypeptide comprising a Group H nuclear receptor ligand binding domain comprising a substitution mutation according to the invention.

In another specific embodiment, the Group H nuclear receptor ligand binding domain comprises a substitution mutation at a position equivalent or analogous to a) amino acid residue 48, 51, 52, 54, 92, 95, 96, 109, 110, 119, 120, 125, 128, 132, 219, 223, 234, or 238 of SEQ ID NO: 1, b) amino acid residues 96 and 119 of SEQ ID NO: 1, c) amino acid residues 110 and 128 of SEQ ID NO: 1, d) amino acid residues 52 and 110 of SEQ ID NO: 1, e) amino acid residues 107, 110, and 127 of SEQ ID NO: 1, or f) amino acid residues 52, 107 and 127 of SEQ ID NO: 1. In another embodiment, the Group H nuclear receptor ligand binding domain comprises substitution mutation at positions equivalent or analogous to amino acid residues 107 and 127, and insertion of amino acid 259 of SEQ ID NO: 1. In a preferred embodiment, the Group H nuclear receptor ligand binding domain is from an ecdysone receptor.

Preferably, the Group H nuclear receptor ligand binding domain comprises a substitution of a) an asparagine, arginine, tyrosine, tryptophan, leucine or lysine residue at a position equivalent to analogous to amino acid residue 48 of SEQ ID NO: 1, b) a methionine, asparagines or leucine residue at a position equivalent or analogous to amino acid residue 51 of SEQ ID NO: 1, c) a leucine, proline, methionine, arginine, tryptophan, glycine, glutamine or glutamic acid residue at a position equivalent or analogous to amino acid residue 52 of SEQ ID NO: 1, d) a tryptophan or threonine at a position equivalent or analogous to amino acid 54 of SEQ ID NO: 1, e) a leucine or glutamic acid at a position equivalent or analogous to amino acid 92 of SEQ ID NO: 1, f) a histidine, methionine or tryptophan residue at a position equivalent or analogous to amino acid residue 95 of SEQ ID NO: 1, g) a leucine, serine, glutamic acid or tryptophan residue at a position equivalent or analogous to amino acid residue 96 of SEQ ID NO: 1, h) a tryptophan, proline, leucine, methionine or asparagine at a position equivalent or analogous to amino acid 109 of SEQ ID NO: 1, i) a glutamic acid, tryptophan or asparagine residue at a position equivalent or analogous to amino acid residue 110 of SEQ ID NO: 1, j) a phenylalanine at a position equivalent or analogous to amino acid 119 of SEQ ID NO: 1, k) a tryptophan or methionine at a position equivalent or analogous to amino acid 120 of SEQ ID NO: 1, l) a glutamic acid, proline, leucine, cysteine, tryptophan, glycine, isoleucine, asparagine, serine, valine or arginine at a position equivalent or analogous to amino acid 125 of SEQ ID NO: 1, m) a phenylalanine at a position equivalent or analogous to amino acid 128 of SEQ ID NO: 1, n) a methionine, asparagine, glutamic acid or valine at a position equivalent or analogous to amino acid 132 of SEQ ID NO: 1, o) an alanine, lysine, tryptophan or tyrosine residue at a position equivalent or analogous to amino acid residue 219 of SEQ ID NO: 1, p) a lysine, arginine or tyrosine residue at a position equivalent or analogous to amino acid residue 223 of SEQ ID NO: 1, q) a methionine, arginine, tryptophan or isoleucine at a position equivalent or analogous to amino acid 234 of SEQ ID NO: 1, r) a proline, glutamic acid, leucine, methionine or tyrosine at a position equivalent or analogous to amino acid 238 of SEQ ID NO: 1, s) a phenylalanine at a position equivalent or analogous to amino acid 119 of SEQ ID NO: 1 and a threonine at a position equivalent or analogous to amino acid 96 of SEQ ID NO: 1, t) a proline at a position equivalent or analogous to amino acid 110 of SEQ ID NO: 1 and a phenylalanine at a position equivalent or analogous to amino acid 128 of SEQ ID NO: 1, u) a valine residue at a position equivalent or analogous to amino acid 52 of SEQ ID NO: 1 and a proline residue residue at a position equivalent or analogous to amino acid 110 of SEQ ID NO: 1, v) an isoleucine at a position equivalent or analogous to amino acid 107 of SEQ ID NO: 1, a glutamic acid at a position equivalent or analogous to amino acid 127 of SEQ ID NO: 1 and a proline at a position equivalent or analogous to amino acid 110 of SEQ ID NO: 1, or w) an isoleucine at a position equivalent or analogous to amino acid 107 of SEQ ID NO: 1, a glutamic acid at a position equivalent or analogous to amino acid 127 of SEQ ID NO: 1 and a valine at a position equivalent or analogous to amino acid 52 of SEQ ID NO: 1. In another embodiment, Group H nuclear receptor ligand binding domain comprises a substitution of an isoleucine residue at a position equivalent or analogous to amino acid 107 of SEQ ID NO: 1, a glutamic acid residue at a position equivalent or analogous to amino acid 127 of SEQ ID NO: 1 and insertion of a glycine residue at a position equivalent or analogous to amino acid 259 of SEQ ID NO: 1. In a preferred embodiment, the Group H nuclear receptor ligand binding domain is from an ecdysone receptor.

In another specific embodiment, the Group H nuclear receptor ligand binding domain comprising a substitution mutation is an ecdysone receptor ligand binding domain polypeptide comprising a substitution mutation, wherein the substitution mutation is selected from the group consisting of F48Y, F48W, F48L, F48N, F48R, F48K, I51M, I51N, I51L, T52M, T52V, T52L, T52E, T52P, T52R, T52W, T52G, T52Q, M54W, M54T, M92L, M92E, R95H, R95M, R95W, V96L, V96W, V96S, V96E, F109W, F109P, F109L, F109M, F109N, A110E, A110N, A110W, N119F, Y120W, Y120M, M125P, M125R, M125E, M125L, M125C, M125W, M125G, M125I, M125N, M125S, M125V, V128F, L132M, L132N, L132V, L132E, M219E, M219W, M219Y, M219A, L223K, L223R, L223Y, L234M, L234I, L234R, L234W, W238P, W238E, W238Y, W238M, W238L, N119F/V96T, V128F/A110P, T52V/A110P, V107I/Y127E/T52V, and V107I/Y127E/A110P substitution mutation of SEQ ID NO: 1. In another embodiment, the Group H nuclear receptor ligand binding domain comprising a substititution mutation is an ecdysone receptor ligand binding domain polypeptide comprising a substitution mutation of V107I/Y127E of SEQ ID NO: 1, which further comprises insertion mutation G259 of SEQ ID NO: 1 (V107I/Y127E/G259).

The present invention also provides an isolated polypeptide selected from the group consisting of a) an isolated polypeptide comprising a transactivation domain, a DNA-binding domain, and a Group H nuclear receptor ligand binding domain comprising a substitution mutation according to the invention; b) an isolated polypeptide comprising a DNA-binding domain and a Group H nuclear receptor ligand binding domain comprising a substitution mutation according to the invention; and c) an isolated polypeptide comprising a transactivation domain and a Group H nuclear receptor ligand binding domain comprising a substitution mutation according to the invention. In a preferred embodiment, the Group H nuclear receptor ligand binding domain is from an ecdysone receptor.

The present invention also provides an isolated hybrid polypeptide selected from the group consisting of a) an isolated hybrid polypeptide comprising a transactivation domain, a DNA-binding domain, and a Group H nuclear receptor ligand binding domain comprising a substitution mutation according to the invention; b) an isolated hybrid polypeptide comprising a DNA-binding domain and a Group H nuclear receptor ligand binding domain comprising a substitution mutation according to the invention; and c) an isolated hybrid polypeptide comprising a transactivation domain and a Group H nuclear receptor ligand binding domain comprising a substitution mutation according to the invention. In a preferred embodiment, the Group H nuclear receptor ligand binding domain is from an ecdysone receptor.

The present invention also provides an isolated polypeptide comprising a Group H nuclear receptor ligand binding domain comprising a substitution mutation that affects ligand binding activity or ligand sensitivity of the Group H nuclear receptor ligand binding domain.

In particular, the present invention relates to an isolated Group H nuclear receptor polypeptide comprising a ligand binding domain comprising a substitution mutation that reduces ligand binding activity or ligand sensitivity of the Group H nuclear receptor ligand binding domain.

In another specific embodiment, the present invention relates to an isolated polypeptide comprising a Group H nuclear receptor ligand binding domain comprising a substitution mutation that reduces non-ecdysteroid diacylhydrazine binding activity or non-ecdysteroid diacylhydrazine sensitivity of the Group H nuclear receptor ligand binding domain. Preferably, the isolated polypeptide comprises a substitution of an amino acid residue at a position equivalent or analogous to amino acid residue 48, 51, 52, 54, 92, 95, 96, 109, 120, 125, 219, 223, 234 or 238 of SEQ ID NO: 1. More preferably, the isolated polypeptide comprises a codon mutation that results in a substitution of a) an asparagine residue at a position equivalent or analogous to amino acid residue 48 or 109 of SEQ ID NO: 1, b) a leucine residue at a position equivalent or analogous to amino acid residue 51, 92, 96 or 238 of SEQ ID NO: 1, c) a glutamic acid residue at a position equivalent or analogous to amino acid residue 52, 92, 96, 125 or 238 of SEQ ID NO: 1, d) a tryptophan residue at a position equivalent or analogous to amino acid residue 54, 95, 96, 120 or 219 of SEQ ID NO: 1, e) a methionine residue at a position equivalent or analogous to amino acid residue 51, 52, 120, 234 or 238 of SEQ ID NO: 1, f) an alanine residue at a position equivalent or analogous to amino acid residue 219 of SEQ ID NO: 1, g) a lysine residue at a position equivalent or analogous to amino acid residue 48, 219 or 223 of SEQ ID NO: 1, h) an isoleucine, arginine or tryptophan residue at a position equivalent or analogous to amino acid residue 234 of SEQ ID NO: 1, i) a tyrosine residue at a position equivalent or analogous to amino acid residue 219 or 238 of SEQ ID NO: 1, j) an arginine residue at a position equivalent or analogous to amino acid residue 52 or 223 of SEQ ID NO: 1, k) a valine residue at a position equivalent or analogous to amino acid residue 125 of SEQ ID NO: 1 or l) a glycine or glutamine residue at a position equivalent or analogous to amino acid residue 52 of SEQ ID NO: 1. Even more preferably, the isolated polypeptide comprises a codon mutation that results in a substitution mutation of F48N, I51L, I51M, T52E, T52M, T52R, T52G, T52Q, M54W, M92L, M92E, R95W, V96W, V96E, V96L, F109N, Y120M, Y120W, M125E, M125V, M219A, M219K, M219W, M219Y, L223K, L223R, L234M, L234I, L234W, L234R, W238E, W238L, W238M or W238Y of SEQ ID NO: 1.

In addition, the present invention also relates to an isolated polypeptide comprising a Group H nuclear receptor ligand binding domain comprising a substitution mutation that enhances ligand binding activity or ligand sensitivity of the Group H nuclear receptor ligand binding domain.

In a specific embodiment, the present invention relates to an isolated polypeptide comprising a Group H nuclear receptor ligand binding domain comprising a substitution mutation that generally enhances ecdysteroid binding activity or ecdysteroid sensitivity of the Group H nuclear receptor ligand binding domain. Preferably, the isolated polypeptide comprises a substitution of an amino acid residue at a position equivalent or analogous to a) amino acid residue 96 of SEQ ID NO: 1 or b) amino acid residues 96 and 119 of SEQ ID NO: 1. More preferably, the isolated polypeptide comprises a codon mutation that results in a substitution of a) a serine residue at a position equivalent or analogous to amino acid residue 96 of SEQ ID NO: 1 or b) a threonine residue at a position equivalent or analogous to amino acid residue 96 of SEQ ID NO: 1 and a phenylalanine residue at a position equivalent or analogous to amino acid residue 119 of SEQ ID NO: 1. Even more preferably, the isolated polypeptide comprises a codon mutation that results in a substitution mutation of V96T or N119F/V96T of SEQ ID NO: 1.

In another specific embodiment, the present invention relates to an isolated polypeptide comprising a Group H nuclear receptor ligand binding domain comprising a substitution mutation that generally enhances diacylhydrazine binding activity or diacylhydrazine sensitivity of the Group H nuclear receptor ligand binding domain. Preferably, the isolated polypeptide comprises a substitution of an amino acid residue at a position equivalent or analogous to a) amino acid residue 48, 52, 54, 109, 110, 125, 132 or 223 of SEQ ID NO: 1 or b) amino acid residues 52 and 110 of SEQ ID NO: 1. More preferably, the isolated polypeptide comprises a codon mutation that results in a substitution of a) a tyrosine, tryptophan, arginine or leucine residue at a position equivalent or analogous to amino acid residue 48 of SEQ ID NO: 1, b) a leucine residue at a position equivalent or analogous to amino acid residue 52 of SEQ ID NO: 1, d) a threonine residue at a position equivalent or analogous to amino acid residue 54 of SEQ ID NO: 1, e) methionine residue at a position equivalent or analogous to amino acid residue 109 of SEQ ID NO: 1, f) a proline, glutamic acid or asparagine residue at a position equivalent or analogous to amino acid residue 110 of SEQ ID NO: 1, g) an isoleucine, glycine or asparagine residue at a position equivalent or analogous to amino acid residue 125 of SEQ ID NO: 1, h) a valine residue at a position equivalent or analogous to amino acid 52 of SEQ ID NO: 1 and a proline residue residue at a position equivalent or analogous to amino acid 110 of SEQ ID NO: 1, i) a glutamic acid residue at a position equivalent or analogous to amino acid residue 132 of SEQ ID NO: 1 or j) a tyrosine residue at a position equivalent or analogous to amino acid residue 223 of SEQ ID NO: 1. Even more preferably, the isolated polypeptide comprises a codon mutation that results in a substitution mutation of F48Y, F48W, F48L, F48R, T52L, M54T, F109M, A110P, A110E, A110N, M125I, M125G, M125N, L132E, L223Y or T52V/A110P of SEQ ID NO: 1.

In another specific embodiment, the present invention relates to an isolated polypeptide comprising a Group H nuclear receptor ligand binding domain comprising a substitution mutation that generally enhances both ecdysteroid binding activity or ecdysteroid sensitivity and non-ecdysteroid diacylhydrazine binding activity or non-ecdysteroid diacylhydrazine sensitivity of the Group H ligand binding domain. Preferably, the isolated polypeptide comprises a substitution of an amino acid residue at a position equivalent or analogous to a) amino acid residue 109, 132 or W238P of SEQ ID NO: 1, b) amino acid residues 52, 107 and 127 of SEQ ID NO: 1 or c) amino acid residues 107 and 127 of SEQ ID NO: 1, and insertion of amino acid 259 of SEQ ID NO: 1. More preferably, the isolated polypeptide comprises a codon mutation that results in a substitution of a) tryptophan residue at a position equivalent or analogous to amino acid residue 109 of SEQ ID NO: 1, b) a valine or methionine residue at a position equivalent or analogous to amino acid residue 132 of SEQ ID NO: 1, c) a proline residue at a position equivalent or analogous to amino acid residue 238 of SEQ ID NO: 1, d) an isoleucine residue at a position equivalent or analogous to amino acid residue 107 of SEQ ID NO: 1, a glutamic acid residue at a position equivalent or analogous to amino acid residue 127 of SEQ ID NO: 1 and a valine residue at a position equivalent or analogous to amino acid residue 132 of SEQ ID NO: 1 or e) an isoleucine residue at a position equivalent or analogous to amino acid 107 of SEQ ID NO: 1, a glutamic acid residue at a position equivalent or analogous to amino acid 127 of SEQ ID NO: 1 and insertion of a glycine residue at a position equivalent or analogous to amino acid 259 of SEQ ID NO: 1. Even more preferably, the isolated polypeptide comprises a codon mutation that results in a substitution mutation of F109W, L132M, L132V, W238P or V107I/Y127E/T52V of SEQ ID NO: 1. In another embodiment, the isolated polypeptide comprises a codon mutation that results in substitution mutation V107I/Y127E of SEQ ID NO: 1, which further comprises insertion mutation G259 of SEQ ID NO: 1 (V107I/Y127E/G259).

In another specific embodiment, the present invention relates to an isolated polypeptide comprising a Group H nuclear receptor ligand binding domain comprising a substitution mutation, wherein the substitution mutation generally enhances diacylhydrazine and tetrahydroquinoline binding activity or diacylhydrazine and tetrahydroquinoline sensitivity of the Group H nuclear receptor ligand binding domain. Preferably, the isolated polypeptide comprises a substitution mutation that results in a substitution of a) amino acid residues at a position equivalent or analogous to amino acid residues 107 and 127 of SEQ ID NO: 1 or b) amino acid residues 107, 110 and 127 of SEQ ID NO: 1. More preferably, the isolated polypeptide comprises a codon mutation that results in a substitution of a) an isoleucine residue at a position equivalent or analogous to amino acid residue 107 of SEQ ID NO: 1 and a glutamic acid residue at a position equivalent or analogous to amino acid residue 127 of SEQ ID NO: 1 or b) an isoleucine residue at a position equivalent or analogous to amino acid residue 107 of SEQ ID NO: 1, a proline residue at a position equivalent or analogous to amino acid residue 110 of SEQ ID NO: 1 and a glutamic acid residue at a position equivalent or analogous to amino acid residue 127 of SEQ ID NO: 1. Even more preferably, the isolated polypeptide comprises a codon mutation that results in a substitution mutation of V107I/Y127E or V107I/Y127E/A110P of SEQ ID NO: 1.

In another specific embodiment, the present invention relates to an isolated polypeptide comprising a Group H nuclear receptor ligand binding domain comprising a substitution mutation, wherein the substitution mutation generally enhances non-ecdysteroid tetrahydroquinoline binding activity or non-ecdysteroid tetrahydroquinoline sensitivity of the Group H nuclear receptor ligand binding domain. Preferably, the isolated polypeptide comprises a codon mutation that results in a substitution of a) amino acid residue at a position equivalent or analogous to amino acid residues 110 or 128 of SEQ ID NO: 1 or b) amino acid residues at a position equivalent or analogous to amino acid residues 110 and 128 of SEQ ID NO: 1. More preferably, the isolated polypeptide comprises a codon mutation that results in a substitution of a) a tryptophan residue at a position equivalent or analogous to amino acid residue 110 of SEQ ID NO: 1, b) a phenylalanine residue at a position equivalent or analogous to amino acid residue 128 of SEQ ID NO: 1 or c) a proline residue at a position equivalent or analogous to amino acid residue 110 of SEQ ID NO: 1 and a phenylalanine residue at a position equivalent or analogous to amino acid residue 128 of SEQ ID NO: 1. Even more preferably, the isolated polypeptide comprises a codon mutation that results in a substitution mutation A110W, V128F or V128F/A110P of SEQ ID NO: 1.

In another specific embodiment, the present invention relates to an isolated polypeptide comprising a Group H nuclear receptor ligand binding domain comprising a substitution mutation, wherein the substitution mutation differentially responds to non-ecdysteroid diacylhydrazine ligands. Preferably, the isolated polypeptide comprises a codon mutation that results in a substitution of an amino acid residue at a position equivalent or analogous to amino acid residues 52, 95, 109, 125 or 132 of SEQ ID NO: 1. More preferably, the isolated polypeptide comprises a codon mutation that results in a substitution of a) a proline residue at a position equivalent or analogous to amino acid residue 52 of SEQ ID NO: 1, b) a histidine or methionine residue residue at a position equivalent or analogous to amino acid residue 95 of SEQ ID NO: 1, c) a leucine residue at a position equivalent or analogous to amino acid residue 109 of SEQ ID NO: 1, d) a leucine, tryptophan, arginine, cysteine or proline residue at a position equivalent or analogous to amino acid residue 125 of SEQ ID NO: 1 or e) a methionine residue at a position equivalent or analogous to amino acid residue 132 of SEQ ID NO: 1. Even more preferably, the isolated polypeptide comprises a codon mutation that results in a substitution mutation T52P, R95H, R95M, F109L, M125L, M125W, M125R, M125C, M125P or L132M of SEQ ID NO: 1.

In another specific embodiment, the present invention relates to an isolated polypeptide comprising a Group H nuclear receptor ligand binding domain comprising a substitution mutation, wherein the substitution mutation differentially responds to non-ecdysteroid diacylhydrazine ligands. More preferably the isolated polypeptide comprises a codon mutation that results in a substitution of a) a lysine or arginine residue at a position equivalent or analogous to amino acid residue 48 of SEQ ID NO: 1, b) a glycine, glutamine, methionine, arginine or tryptophan residue at a position equivalent or analogous to amino acid residue 52 of SEQ ID NO: 1, c) an isoleucine, glycine, asparagines, serine or valine residue at a position equivalent or analogous to amino acid residue 125 of SEQ ID NO: 1, d) a glutamic acid residue at a position equivalent or analogous to amino acid residue 132 of SEQ ID NO: 1, e) a lysine, tryptophan or tyrosine residue at a position equivalent or analogous to amino acid residue 219 of SEQ ID NO: 1, f) an arginine or tyrosine residue at a position equivalent or analogous to amino acid residue 223 of SEQ ID NO: 1 or g) leucine or methionine residue at a position equivalent or analogous to amino acid residue 238 of SEQ ID NO: 1. Even more preferably the isolated polypeptide comprises a codon mutation that results in a substitution mutation F48K, F48R, T52G, T52Q, T52M, T52R, T52W, M125I, M125G, M125N, M125S, M125V, L132E, M219K, M219W, M219Y, L223R, L223Y, W238L or W238M of SEQ ID NO: 1.

The present invention also relates to compositions comprising an isolated polypeptide according to the invention.

Method of Modulating Gene Expression of the Invention

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

Applicants' invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Genes of interest for expression in a host cell using Applicants' methods may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for expression in a host cell using Applicants' methods include, but are not limited to: antigens produced in plants as vaccines, enzymes like alpha-amylase, phytase, glucanes, xylase and xylanase, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Acceptable ligands are any that modulate expression of the gene when binding of the DNA binding domain of the gene expression system according to the invention to the response element in the presence of the ligand results in activation or suppression of expression of the genes. Preferred ligands include an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U. S. Pat. Nos. 6,013,836; 5,117,057; 5,530,028; 5,378,726; and U.S. patent application Ser. Nos. 10/775,883 and 10/787,906; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U. S. Pat. No. 4,985,461; tetrahydroquinolines such as those disclosed in International Application No. PCT/US03/00915; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, Juvenile hormone III, and the like.

In a preferred embodiment, the ligand for use in Applicants' method of modulating expression of gene is a compound of the formula:

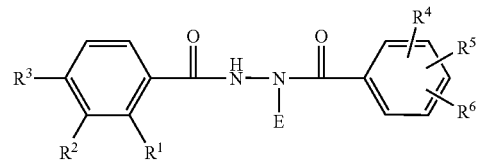

wherein:
E is a branched ($C_4$-$C_{12}$)alkyl or branched ($C_4$-$C_{12}$)alkenyl containing a tertiary carbon or a cyano($C_3$-$C_{12}$)alkyl containing a tertiary carbon;
$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, OH, OMe, OEt, cyclopropyl, $CF_2CF_3$, CH=CHCN, allyl, azido, SCN, or $SCHF_2$;
$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C°CH, 1-propynyl, 2-propynyl, vinyl, OMe, OEt, SMe, or Set.

In another preferred embodiment, the ligand for use in Applicants' method of modulating expression of gene is a compound of the formula:

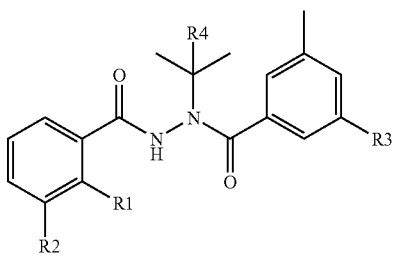

wherein:

| | R1 | R2 | R3 | R4 |
|---|---|---|---|---|
| 1 | —$CH_2CH_3$ | —$OCH_3$ | —$CH_3$ | —$CH_3$ |
| 2 | —$CH_3$ | —$CH_2CH_3$ | —CH3 | —$CH_3$ |
| 3 | —$CH_3$ | -i-Pr | —CH3 | —$CH_3$ |

In another preferred embodiment, the ligand for use in Applicants' method of modulating expression of gene is a compound of the formula:

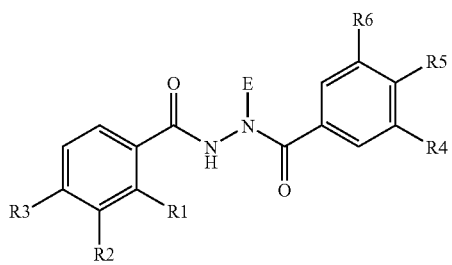

wherein:

| R1 | R2 | R3 | R4 | R5 | R6 | E |
|---|---|---|---|---|---|---|
| 1 —$CH_2CH_3$ | —$OCH_2CH_2O$— | —$OCH_3$ | —$CH_3$ | —$OCH_3$ | —$CH(CH_2CH_3)tBu$ |
| 2 H | H | —$CH_2CH_3$ | —$CH_3$ | H | —$CH_3$ | —$CH(nBu)tBu$ |
| 3 —$CH_2CH_3$ | —$OCH_2CH_2O$— | —$OCH_3$ | —$CH_3$ | —$OCH_3$ | —$CH(tBu)CH=C(CH_3)tBu$ |

In a further preferred embodiment, the ligand for use in Applicants' method of modulating expression of gene is a compound of the formula:

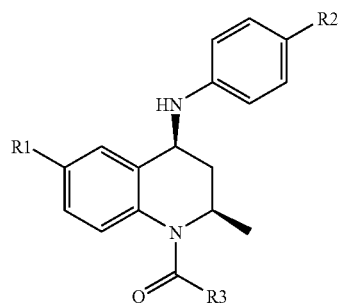

wherein:

| | R1 | R2 | R3 |
|---|---|---|---|
| 1 | F | F | 3-F-4-$CH_3$—Ph— |
| 2 | F | F | 3-$CH_3$-4-F—Ph— |

In another preferred embodiment, the ligand for use in Applicants' method of modulating expression of gene is an ecdysone, 20-hydroxyecdysone, ponasterone A, muristerone A, an oxysterol, a 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, or Juvenile hormone III.

In another preferred embodiment, a second ligand may be used in addition to the first ligand discussed above in Applicants' method of modulating expression of a gene. Preferably, this second ligand is 9-cis-retinoic acid or a synthetic analog of retinoic acid.

Host Cells and Non-Human Organisms of the Invention

As described above, the gene expression modulation system of the present invention may be used to modulate gene expression in a host cell. Expression in transgenic host cells may be useful for the expression of various genes of interest. Applicants' invention provides for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanes, xylase and xylanase, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Thus, Applicants' invention provides an isolated host cell comprising a gene expression system according to the invention. The present invention also provides an isolated host cell comprising a gene expression cassette according to the invention. Applicants' invention also provides an isolated host cell comprising a polynucleotide or a polypeptide according to the invention. The present invention also relates to a host cell transfected with an expression vector according to the invention. The host cell may be a bacterial cell, a fungal cell, a nematode cell, an insect cell, a fish cell, a plant cell, an avian cell, an animal cell, or a mammalian cell. In still another embodiment, the invention relates to a method for producing a nuclear receptor ligand binding domain comprising a substitution mutation, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated host cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the host cell is a yeast cell selected from the group consisting of a *Saccharomyces*, a *Pichia*, and a *Candida* host cell.

In another specific embodiment, the host cell is a *Caenorhabdus elegans* nematode cell.

In another specific embodiment, the host cell is an insect cell.

In another specific embodiment, the host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another specific embodiment, the host cell is a zebrafish cell.

In another specific embodiment, the host cell is a chicken cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces, Pichia*, and *Candida*.

In another specific embodiment, the non-human organism is a *Caenorhabdus elegans* nematode.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Measuring Gene Expression/Transcription

One useful measurement of Applicants' methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybidizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

Ligand Screening Assays

The present invention also relates to methods of screening for a compound that induces or represses transactivation of a nuclear receptor ligand binding domain comprising a substitution mutation in a cell by contacting a nuclear receptor ligand binding domain with a candidate molecule and detecting reporter gene activity in the presence of the ligand. Candidate compounds may be either agonists or antagonists of the nuclear receptor ligand binding domain. In a preferred embodiment, the nuclear receptor ligand binding domain is expressed from a polynucleotide in the cell and the transactivation activity (i.e., expression or repression of a reporter gene) or compound binding activity is measured.

Accordingly, in addition to rational design of agonists and antagonists based on the structure of a nuclear receptor ligand binding domain, the present invention contemplates an alternative method for identifying specific ligands of a nuclear receptor ligand binding domain using various screening assays known in the art.

Any screening technique known in the art can be used to screen for Group H nuclear receptor ligand binding domain agonists or antagonists. For example, a suitable cell line comprising a nuclear receptor-based gene expression system according to the invention can be transfected with a gene expression cassette encoding a marker gene operatively linked to an inducible or repressible promoter. The transfected cells are then exposed to a test solution comprising a candidate agonist or antagonist compound, and then assayed for marker gene expression or repression. The presence of more marker gene expression relative to control cells not exposed to the test solution is an indication of the presence of an agonist compound in the test solution. Conversely, the presence of less marker gene expression relative to control cells not exposed to the test solution is an indication of the presence of an antagonist compound in the test solution.

The present invention contemplates screens for small molecule ligands or ligand analogs and mimics, as well as screens for natural ligands that bind to and agonize or antagonize a Group H nuclear receptor ligand binding domain according to the invention in vivo. For example, natural products libraries can be screened using assays of the invention for molecules that agonize or antagonize nuclear receptor-based gene expression system activity.

Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249: 386-390 (1990); Cwirla, et al., *Proc. Natl. Acad. Sci.*, 87: 6378-6382 (1990); Devlin et al., *Science*, 249: 404-406 (1990)], very large libraries can be constructed (10⁶-10⁸ chemical entities). A second approach uses primarily chemical methods, of which the Geysen method [Geysen et al., *Molecular Immunology* 23: 709-715 (1986); Geysen et al. *J. Immunologic Method* 102: 259-274 (1987)] and the method of Fodor et al. [*Science* 251: 767-773 (1991)] are examples. Furka et al. [14*th International Congress of Biochemistry, Volume* 5, Abstract FR:013 (1988); Furka, *Int. J. Peptide Protein Res.* 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90: 10700-4 (1993); Ohlmeyer et al., *Proc. Natl. Acad. Sci. USA* 90: 10922-10926 (1993); Lam et al., International Patent Publication No. WO 92/00252; Kocis et al., International Patent Publication No. WO 9428028, each of which is incorporated herein by reference in its entirety], and the like can be used to screen for candidate ligands according to the present invention.

The screening can be performed with recombinant cells that express a nuclear receptor ligand binding domain according to the invention, or alternatively, using purified protein, e.g., produced recombinantly, as described above. For example, labeled, soluble nuclear receptor ligand binding domains can be used to screen libraries, as described in the foregoing references.

In one embodiment, a Group H nuclear receptor ligand binding domain according to the invention may be directly labeled. In another embodiment, a labeled secondary reagent may be used to detect binding of a nuclear receptor ligand binding domain of the invention to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two-color assay, using two chromogenic substrates with two enzyme labels on different acceptor molecules of interest, may be used. Cross-reactive and singly reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radioisotopes, or magnetic resonance imaging labels. Two-color assays may be performed with two or more colored latex beads, or fluorophores that emit at different wavelengths. Labeled molecules or cells may be detected visually or by mechanical/optical means. Mechanical/optical means include fluorescence activated sorting, i.e., analogous to FACS, and micromanipulator removal means.

The present invention may be better understood by reference to the following non-limiting Examples, which are provided as exemplary of the invention.

EXAMPLES

Applicants have developed a CfEcR homology model and have used this homology model together with a published *Chironomous tetans* ecdysone receptor ("CtEcR") homology model (Wurtz et al., 2000) to identify critical residues involved in binding to ecdysteroids and non-ecdysteroids. The synthetic non-steroid, diacylhydrazines, have been shown to bind lepidopteran EcRs with high affinity and induce precocious incomplete molt in these insects (Wing et al., 1988) and several of these compounds are currently marketed as insecticides. The ligand binding cavity of EcRs has evolved to fit the long backbone structures of ecdysteroids such as 20E. The diacylhydrazines have a compact structure compared to ecdysteroids and occupy only the bottom part of the EcR binding pocket. This leaves a few critical residues at the top part of the binding pocket that make contact with ecdysteroids but not with non-ecdysteroids such as diacylhydrazines. Applicants made substitution mutations of the residues that make contact with ecdysteroids and/or non-ecdysteroids and determined the mutational effect on ligand binding. Applicants describe herein substitution mutations at several of these residues and have identified several classes of substitution mutant receptors based upon their binding and transactivation characteristics. Applicants' novel substitution mutated nuclear receptor polynucleotides and polypeptides are useful in a nuclear receptor-based inducible gene modulation system for various applications including gene therapy, expression of proteins of interest in host cells, production of transgenic organisms, and cell-based assays.

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "µL" means microliter(s), "mL" means milliliter(s), "L" means liter(s), "µM" means micromolar, "mM" means millimolar, "µg" means microgram(s), "mg" means milligram(s), "A" means adenine or adenosine, "T" means thymine or thymidine, "G" means guanine or guanosine, "C" means cytidine or cytosine, "x g" means times gravity, "nt" means nucleotide(s), "aa" means amino acid(s), "bp" means

Example 1

This Example describes the construction of several gene expression cassettes comprising novel substitution mutant Group H nuclear receptor polynucleotides and polypeptides of the invention for use in a nuclear receptor-based inducible gene expression system. Applicants constructed gene expression cassettes based on the spruce budworm *Choristoneura fumiferana* EcR ("CfEcR"). The prepared receptor constructs comprise a ligand binding domain of either an EcR or a chimera of *Homo sapiens* RXRβ-LmRXR; and a GAL4 DNA binding domain (DBD) or a VP16 transactivation domain (AD). The reporter constructs include the reporter gene luciferase operably linked to a synthetic promoter construct that comprises a GAL4 response element to which the Gal4 DBD binds. Various combinations of these receptor and reporter constructs were cotransfected into mammalian cells as described in Examples 2-5 infra.

Gene Expression Cassettes: Ecdysone receptor-based gene expression cassettes (switches) were constructed as followed, using standard cloning methods available in the art. The following is a brief description of preparation and composition of each switch used in the Examples described herein.

1.1—GAL4CfEcR-DEF/VP16-βRXREF-LmRXREF:
The wild-type D, E, and F domains from spruce budworm *Choristoneura fumiferana* EcR ("CfEcR-DEF"; SEQ ID NO: 21) were fused to a GAL4 DNA binding domain ("Gal4DNABD" or "Gal4DBD"; SEQ ID NO: 6) and placed under the control of a CMV promoter (SEQ ID NO: 2). Helices 1 through 8 of the EF domains from *Homo sapiens* RXRβ ("HsRXRβ-EF"; nucleotides 1-465 of SEQ ID NO: 3) and helices 9 through 12 of the EF domains of *Locusta migratoria* Ultraspiracle Protein ("LmRXR-EF"; nucleotides 403-630 of SEQ ID NO: 23) were fused to the transactivation domain from VP16 ("VP16AD"; SEQ ID NO: 12) and placed under the control of an SV40e promoter (SEQ ID NO: 22). Five consensus GAL4 response element binding sites ("5× GAL4RE"; comprising 5 copies of a GAL4RE comprising SEQ ID NO: 19) were fused to a synthetic TATA minimal promoter (SEQ ID NO: 24) and placed upstream of the luciferase reporter gene (SEQ ID NO: 25).

1.2—GAL4/mutantCfEcR-DEF/VP16-βRXREF-LmRXREF: This construct was prepared in the same way as in switch 1.1 above except wild-type CfEcR-DEF was replaced with mutant CfEcR-DEF comprising a ligand binding domain comprising a substitution mutation selected from Table 1 below.

TABLE 1

Substitution Mutants of *Choristoneura fumiferana* Ecdysone Receptor ("CfEcR") Ligand Binding Domain (LBD).

| CfEcR LBD Mutation | Resulting "WT to Mutant" Amino Acid Substitution | Corresponding amino acid in full length CfEcR (SEQ ID NO: 26) |
|---|---|---|
| F48Y | Phenylalanine (F) to Tyrosine (Y) | 331 |
| F48W | Phenylalanine (F) to Tryptophan (W) | 331 |
| F48L | Phenylalanine (F) to Leucine (L) | 331 |
| F48N | Phenylalanine (F) to Asparagine (N) | 331 |
| F48R | Phenylalanine (F) to Arginine (R) | 331 |
| F48K | Phenylalanine (F) to Lysine (K) | 331 |
| I51N | Isoleucine (I) to Asparagine (N) | 334 |
| I51L | Isoleucine (I) to Leucine (L) | 334 |
| I51M | Isoleucine (I) to Methionine (M) | 334 |
| T52M | Threonine (T) to Methionine (M) | 335 |
| T52R | Threonine (T) to Arginine (R) | 335 |
| T52W | Threonine (T) to Tryptophan (W) | 335 |
| T52G | Threonine (T) to Glycine (G) | 335 |
| T52Q | Threonine (T) to Glutamine (Q) | 335 |
| T52E | Threonine (T) to Glutamic Acid (E) | 335 |
| T52P | Threonine (T) to Proline (P) | 335 |
| M54W | Methionine (M) to Tryptophan (W) | 337 |
| M54T | Methionine (M) to Threonine (T) | 337 |
| M92L | Methionine (M) to Leucine (L) | 375 |
| M92E | Methionine (M) to Glutamic Acid (E) | 375 |
| R95H | Arginine (R) to Histidine (H) | 378 |
| R95M | Arginine (R) to Methionine (M) | 378 |
| R95W | Arginine (R) to Tryptophan (W) | 378 |
| V96L | Valine (V) to Leucine (L) | 379 |
| V96W | Valine (V) to Tryptophan (W) | 379 |
| V96S | Valine (V) to Serine (S) | 379 |
| V96E | Valine (V) to Glutamic Acid (E) | 379 |
| V107I | Valine (V) to Isoleucine (I) | 390 |
| F109L | Phenlyalanine (F) to Leucine (L) | 392 |
| F109P | Phenylalanine (F) to Proline (P) | 392 |
| F109W | Phenylalanine (F) to Tryptophan (W) | 392 |
| F109M | Phenylalanine (F) to Methionine (M) | 392 |
| F109N | Phenylalanine (F) to Asparagine (N) | 392 |
| A110E | Alanine (A) to Glutamatic Acid (E) | 393 |
| A110N | Alanine (A) to Asparagine (N) | 393 |
| A110W | Alanine (A) to Tryptophan (W) | 393 |
| N119F | Asparagine (N) to Phenylalanine (F) | 402 |
| Y120W | Tyrosine (Y) to Tryptophan (W) | 403 |
| Y120M | Tyrosine (Y) to Methionine (M) | 403 |
| M125E | Methionine (M) to Glutamic Acid (E) | 408 |
| M125P | Methionine (M) to Proline (P) | 408 |

TABLE 1-continued

Substitution Mutants of *Choristoneura fumiferana* Ecdysone Receptor ("CfEcR") Ligand Binding Domain (LBD).

| CfEcR LBD Mutation | Resulting "WT to Mutant" Amino Acid Substitution | Corresponding amino acid in full length CfEcR (SEQ ID NO: 26) |
|---|---|---|
| M125R | Methionine (M) to Arginine (R) | 408 |
| M125L | Methionine (M) to Leucine (L) | 408 |
| M125C | Methionine (M) to Cysteine (C) | 408 |
| M125W | Methionine (M) to Tryptophan (W) | 408 |
| M125G | Methionine (M) to Glycine (G) | 408 |
| M125I | Methionine (M) to Isoleucine (I) | 408 |
| M125N | Methionine (M) to Asparagine (N) | 408 |
| M125S | Methionine (M) to Serine (S) | 408 |
| M125V | Methionine (M) to Valine (V) | 408 |
| V128F | Valine (V) to Phenylalanine (F) | 411 |
| L132M | Leucine (L) to Methionine (M) | 415 |
| L132N | Leucine (L) to Asparagine (N) | 415 |
| L132V | Leucine (L) to Valine (V) | 415 |
| L132E | Leucine (L) to Glutamic Acid (E) | 415 |
| R175E | Arginine (R) to Glutamic Acid (E) | 458 |
| M219K | Methionine (M) to Lysine (K) | 502 |
| M219W | Methionine (M) to Tryptophan (W) | 502 |
| M219Y | Methionine (M) to Tyrosine (Y) | 502 |
| M219A | Methionine (M) to Alanine (A) | 502 |
| L223K | Leucine (L) to Lysine (K) | 506 |
| L223R | Leucine (L) to Arginine (R) | 506 |
| L223Y | Leucine (L) to Tyrosine (Y) | 506 |
| L234M | Leucine (L) to Methionine (M) | 517 |
| L234I | Leucine (L) to Isoleucine (I) | 517 |
| L234R | Leucine (L) to Arginine (R) | 517 |
| L234W | Leucine (L) to Tryptophan (W) | 517 |
| W238P | Tryptophan (W) to Proline (P) | 521 |
| W238E | Tryptophan (W) to Glutamic Acid (E) | 521 |
| W238Y | Tryptophan (W) to Tyrosine (Y) | 521 |
| W238L | Tryptophan (W) to Leucine (L) | 521 |
| W238M | Tryptophan (W) to Methionine (M) | 521 |
| T52V and A110P double mutant | Threonine (T) to Valine (V) and Alanine (A) to Proline (P), respectively | 335 and 393, respectively |
| N119F and V96T double mutant | Asparagine (N) to Phenylalanine (F) and Valine (V) to Threonine (T), respectively | 402 and 379, respectively |
| V128F and A110P double mutant | Valine (V) to Phenylalanine (F) and Alanine (A) to Proline (P), respectively | 411 and 393, respectively |
| T52V, V107I and R175E triple mutant | Threonine (T) to Valine (V), Valine (V) to Isoleucine (I) and Arginine (R) to Glutamic Acid (E), respectively | 335, 390 and 458, respectively |
| T52A, V107I and R175E triple mutant | Threonine (T) to Alanine (A), Valine (V) to Isoleucine (I) and Arginine (R) to Glutamic Acid (E), respectively | 335, 390 and 458, respectively |
| V96A, V107I and R175E triple mutant | Valine (V) to Alanine (A), Valine (V) to Isoleucine (I) and Arginine (R) to Glutamic Acid (E), respectively | 379, 390 and 458, respectively |
| V96T, V107I and R175E triple mutant | Valine (V) to Threonine (T), Valine (V) to Isoleucine (I) and Arginine (R) to Glutamic Acid (E), respectively | 379, 390 and 458, respectively |
| V107I, Y127E and A110P triple mutant | Valine (V) to Isoleucine (I), Tyrosine (Y) to Glutamic Acid (E) and Alanine (A) to Proline (P), respectively | 390, 410 and 393, respectively |
| V107I, Y127E and R175E triple mutant | Valine (V) to Isoleucine (I), Tyrosine (Y) to Glutamic Acid (E) and Arginine (R) to Glutamic Acid (E), respectively | 390, 410 and 458, respectively |
| V107I, A110P and R175E triple mutant | Valine (V) to Isoleucine (I), Alanine (A) to Proline (P) and Arginine (R) to Glutamic Acid (E), respectively | 390, 393, and 458, respectively |
| V107I, Y127E, T52V triple mutant | Valine (V) to Isoleucine (I), Tyrosine (Y) to Glutamic Acid (E), and Threonine (T) to Valine (V) | 390, 410 and 335, respectively |
| V107I/Y127E/G | Valine (V) to Isoleucine (I), Tyrosine (Y) to Glutamic Acid (E), and Glycine, respectively | 390, 410, and 542, respectively |

Construction of Ecdysone Receptor Ligand Binding Domains Comprising a Substitution Mutation:

In an effort to modify EcR ligand binding, residues within the EcR ligand binding domains that were predicted to be important for ligand binding based upon a molecular modeling analysis were mutated in EcRs from three different classes of organisms. Table 1 indicates the amino acid residues within the ligand binding domain of CfEcR (Lepidopteran EcR) (SEQ ID NO: 1) that were mutated and examined for modification of ecdysteroid and non-ecdysteroid binding.

Each one of the amino acid substitution mutations listed in Table 1 was constructed in an EcR cDNA by PCR mediated site-directed mutagenesis. In addition to the many single mutation point mutations made, two different double point mutant CfEcRs were also made: one comprising both the V128F and A110P substitutions (V128F/A110P), and a second comprising both the N119F and V96T substitutions (N119F/V96T). Three different triple point mutant CfEcRs were also made: one comprising the V107I, Y127E and A110P substitutions (V107I/Y127E/A110P), the second comprising the V107I, Y127E and T52V substitutions (V107I/Y127E/T52V), and the third comprising the V107I and Y127E substitutions and a glycine (G) insertion (V107I/Y127E/259G) (SEQ ID NO: 1).

PCR site-directed mutagenesis was performed using the Quikchange site-directed mutagenesis kit (Stratagene, La Jolla, Calif.) using the reaction conditions and cycling parameters as follows. PCR site-directed mutagenesis was performed using 1× reaction buffer (supplied by manufacturer), 50 ng of dsDNA template, 125 ng of forward primer (FP), 125 ng of reverse complementary primer (RCP), and 1 μL of dNTP mix (supplied by manufacturer) in a final reaction volume of 50 μL. The forward primer and reverse complementary primer used to produce each EcR mutant are presented in Table 2. The cycling parameters used consisted of one cycle of denaturing at 95° C. for 30 seconds, followed by 16 cycles of denaturating at 95° C. for 30 seconds, annealing at 55° C. for 1 minute, and extending at 68° C. for 22 minutes.

TABLE 2

PCR Primers for Substitution Mutant CfEcR Ligand Binding Domain Construction

| MUTANT | PRIMER (SEQ ID NO:) | PRIMER NUCLEOTIDE SEQUENCE (5' TO 3') |
|---|---|---|
| F48Y | FP (SEQ ID NO: 27) | gtcggacactccctaccgccagatcacag |
| F48Y | RCP (SEQ ID NO: 28) | ctgtgatctggcggtagggagtgtccgac |
| F48W | FP (SEQ ID NO: 29) | gtcggacactccctggcgccagatcacagag |
| F48W | RCP (SEQ ID NO: 30) | ctctgtgatctggcgccagggagtgtccgac |
| F48L | FP (SEQ ID NO: 31) | gtcggacactcccttgcgccagatcacag |
| F48L | RCP (SEQ ID NO: 32) | ctgtgatctggcgcaagggagtgtccgac |
| F48N | FP (SEQ ID NO: 33) | gaggctgacactcccaaccgccagatcacagag |
| F48N | RCP (SEQ ID NO: 34) | ctctgtgatctggcggttgggagtgtcagcctc |
| F48R | FP (SEQ ID NO: 35) | gtcggacactccccgccgccagatcacag |
| F48R | RCP (SEQ ID NO: 36) | ctgtgatctggcggcggggagtgtccgac |
| F48K | FP (SEQ ID NO: 37) | gtcggacactcccaagcgccagatcacag |
| F48K | RCP (SEQ ID NO: 38) | ctgtgatctggcgcttgggagtgtccgac |
| I51N | FP (SEQ ID NO: 39) | ctcccttccgccagaacacagagatgactatc |
| I51N | RCP (SEQ ID NO: 40) | gatagtcatctctgtgttctggcggaagggag |
| I51L | FP (SEQ ID NO: 41) | ctcccttccgccagctcacagagatgac |
| I51L | RCP (SEQ ID NO: 42) | gtcatctctgtgagctggcggaagggag |

TABLE 2-continued PCR Primers for Substitution Mutant CfEcR Ligand Binding Domain Construction

| MUTANT | PRIMER (SEQ ID NO:) | PRIMER NUCLEOTIDE SEQUENCE (5' TO 3') |
|---|---|---|
| I51M | FP (SEQ ID NO: 43) | cactcccttccgccagatgacagagatgac |
| I51M | RCP (SEQ ID NO: 44) | gtcatctctgtcatctggcggaagggagtg |
| T52M | FP (SEQ ID NO: 45) | cccttccgccagatcatggagatgactatcctcac |
| T52M | RCP (SEQ ID NO: 46) | gtgaggatagtcatctccatgatctggcggaaggg |
| T52R | FP (SEQ ID NO: 47) | cttccgccagatcagagagatgactatcctcac |
| T52R | RCP (SEQ ID NO: 48) | gtgaggatagtcatctctctgatctggcggaag |
| T52W | FP (SEQ ID NO: 49) | ctcccttccgccagatctgggagatgactatcctcac |
| T52W | RCP (SEQ ID NO: 50) | gtgaggatagtcatctcccagatctggcggaagggag |
| T52L | FP (SEQ ID NO: 51) | cccttccgccagatcctagagatgactatcctcac |
| T52L | RCP (SEQ ID NO: 52) | gtgaggatagtcatctctaggatctggcggaaggg |
| T52E | FP (SEQ ID NO: 53) | ctcccttccgccagatcgaggagatgactatcctcac |
| T52E | RCP (SEQ ID NO: 54) | gtgaggatagtcatctcctcgatctggcggaagggag |
| T52P | FP (SEQ ID NO: 55) | cttccgccagatcccagagatgactatcctc |
| T52P | RCP (SEQ ID NO: 56) | gaggatagtcatctctgggatctggcggaag |
| T52G | FP (SEQ ID NO: 57) | cttccgccagatcggagagatgactatcctcac |
| T52G | RCP (SEQ ID NO: 58) | gtgaggatagtcatctctccgatctggcggaag |
| T52Q | FP (SEQ ID NO: 59) | cttccgccagatccaagagatgactatcctcac |
| T52Q | RCP (SEQ ID NO: 60) | gtgaggatagtcatctcttggatctggcggaag |
| T52V | FP (SEQ ID NO: 61) | cccttccgccagatcgtagagatgactatcctcac |
| T52V | RCP (SEQ ID NO: 62) | gtgaggatagtcatctctacgatctggcggaaggg |
| M54W | FP (SEQ ID NO: 63) | cgccagatcacagagtggactatcctcacggtc |
| M54W | RCP (SEQ ID NO: 64) | gaccgtgaggatagtccactctgtgatctggcg |
| M54T | FP (SEQ ID NO: 65) | ccagatcacagagacgactatcctcacggtc |
| M54T | RCP (SEQ ID NO: 66) | gaccgtgaggatagtcgtctctgtgatctgg |
| M92L | FP (SEQ ID NO: 67) | gctcaagtgaggtactgatgctccgagtcg |

TABLE 2-continued

PCR Primers for Substitution Mutant CfEcR Ligand Binding Domain Construction

| MUTANT | PRIMER (SEQ ID NO:) | PRIMER NUCLEOTIDE SEQUENCE (5' TO 3') |
|---|---|---|
| M92L | RCP (SEQ ID NO: 68) | cgactcggagcatcagtacctcacttgagc |
| M92E | FP (SEQ ID NO: 69) | gctcaagtgaggtagagatgctccgagtcgcg |
| M92E | RCP (SEQ ID NO: 70) | cgcgactcggagcatctctacctcacttgagc |
| R95H | FP (SEQ ID NO: 71) | gaggtaatgatgctccacgtcgcgcgacgatac |
| R95H | RCP (SEQ ID NO: 72) | gtatcgtcgcgcgacgtggagcatcattacctc |
| R95M | FP (SEQ ID NO: 73) | gtgaggtaatgatgctcatggtcgcgcgacgatacgatg |
| R95M | RCP (SEQ ID NO: 74) | catcgtatcgtcgcgcgaccatgagcatcattacctcac |
| R95W | FP (SEQ ID NO: 75) | gtgaggtaatgatgctctgggtcgcgcgacgatacg |
| R95W | RCP (SEQ ID NO: 76) | cgtatcgtcgcgcgacccagagcatcattacctcac |
| V96L | FP (SEQ ID NO: 77) | gtaatgatgctccgactcgcgcgacgatac |
| V96L | RCP (SEQ ID NO: 78) | gtatcgtcgcgcgagtcggagcatcattac |
| V96W | FP (SEQ ID NO: 79) | gaggtaatgatgctccgatgggcgcgacgatacgatg |
| V96W | RCP (SEQ ID NO: 80) | catcgtatcgtcgcgcccatcggagcatcattacctc |
| V96S | FP (SEQ ID NO: 81) | ggtaatgatgctccgatccgcgcgacgatacg |
| V96S | RCP (SEQ ID NO: 82) | cgtatcgtcgcgcggatcggagcatcattacc |
| V96E | FP (SEQ ID NO: 83) | ggtaatgatgctccgagaggcgcgacgatacg |
| V96E | RCP (SEQ ID NO: 84) | cgtatcgtcgcgcctctcggagcatcattacc |
| V96T | FP (SEQ ID NO: 85) | ggtaatgatgctccgaaccgcgcgacgatacg |
| V96T | RCP (SEQ ID NO: 86) | cgtatcgtcgcgcggttcggagcatcattacc |
| V107I | FP (SEQ ID NO: 87) | gcggcctcagacagtattctgttcgcgaac |
| V107I | RCP (SEQ ID NO: 88) | gttcgcgaacagaatactgtctgaggccgc |
| F109W | FP (SEQ ID NO: 89) | ctcagacagtgttctgtgggcgaacaaccaagcg |
| F109W | RCP (SEQ ID NO: 90) | cgcttggttgttcgcccacagaacactgtctgag |
| F109P | FP (SEQ ID NO: 91) | ctcagacagtgttctgcccgcgaacaaccaagc |

TABLE 2-continued

PCR Primers for Substitution Mutant CfEcR Ligand Binding Domain Construction

| MUTANT | PRIMER (SEQ ID NO:) | PRIMER NUCLEOTIDE SEQUENCE (5' TO 3') |
|---|---|---|
| F109P | RGP (SEQ ID NO: 92) | gcttggttgttcgcgggcagaacactgtctgag |
| F109L | FP (SEQ ID NO: 93) | cagacagtgttctgttggcgaacaaccaagcg |
| F109L | RCP (SEQ ID NO: 94) | cgcttggttgttcgccaacagaacactgtctg |
| F109M | FP (SEQ ID NO: 95) | cctcagacagtgttctgatggcgaacaaccaagcg |
| F109M | RCP (SEQ ID NO: 96) | cgcttggttgttcgccatcagaacactgtctgagg |
| F109N | FP (SEQ ID NO: 97) | cctcagacagtgttctgaacgcgaacaaccaagcg |
| F109N | RCP (SEQ ID NO: 98) | cgcttggttgttcgcgttcagaacactgtctgagg |
| A110P | FP (SEQ ID NO: 99) | cagacagtgttctgttcccgaacaaccaagcg |
| A110P | RCP (SEQ ID NO: 100) | cgcttggttgttcgggaacagaacactgtctg |
| A110E | FP (SEQ ID NO: 101) | gacagtgttctgttcgagaacaaccaagcgtacac |
| A110E | RCP (SEQ ID NO: 102) | gtgtacgcttggttgttctcgaacagaacactgtc |
| A110N | FP (SEQ ID NO: 103) | cagacatctgttcaacaacaaccaagcgtacactcgcg |
| A110N | RCP (SEQ ID NO: 104) | cgcgagtgtacgcttggttgttgttgaacagaacactgtctg |
| A110W | FP (SEQ ID NO: 105) | cagacatgttctgttctggaacaaccaagcgtacactc |
| A110W | RCP (SEQ ID NO: 106) | gagtgtacgcttggttgttccagaacagaacactgtctg |
| N119n | RANDOM FP (SEQ ID NO: 107) | gcgtacactcgcgacnnntaccgcaaggctggcatgg |
| N119n | RANDOM RCP (SEQ ID NO: 108) | ccatgccagccttgcggtannngtcgcgagtgtacgc |
| Y120W | FP (SEQ ID NO: 109) | cactcgcgacaactggcgcaaggctggcatg |
| Y120W | RCP (SEQ ID NO: 110) | catgccagccttgcgccagttgtcgcgagtg |
| Y120M | FP (SEQ ID NO: 111) | cactcgcgacaacatgcgcaaggctggcatggcc |
| Y120M | RCP (SEQ ID NO: 112) | ggccatgccagccttgcgcatgttgtcgcgagtg |
| M125P | FP (SEQ ID NO: 113) | caaggctggcccggcctacgtcatcgag |
| M125P | RCP (SEQ ID NO: 114) | ctcgatgacgtaggccgggccagccttg |
| M125R | FP (SEQ ID NO: 115) | caaggctggcagggcctacgtcatcg |

TABLE 2-continued

PCR Primers for Substitution Mutant CfEcR Ligand Binding Domain Construction

| MUTANT | PRIMER (SEQ ID NO:) | PRIMER NUCLEOTIDE SEQUENCE (5' TO 3') |
|---|---|---|
| M125R | RCP (SEQ ID NO: 116) | cgatgacgtaggccctgccagccttg |
| M125E | FP (SEQ ID NO: 117) | gcaaggctggcgaggcctacgtcatcgag |
| M125E | RCP (SEQ ID NO: 118) | ctcgatgacgtaggcctcgccagccttgc |
| M125L | FP (SEQ ID NO: 119) | caaggctggcctggcctacgtcatcg |
| M125L | RCP (SEQ ID NO: 120) | cgatgacgtaggccaggccagccttg |
| M125C | FP (SEQ ID NO: 121) | ccgcaaggctggctgcgcctacgtcatcgagg |
| M125C | RCP (SEQ ID NO: 122) | cctcgatgacgtaggcgcagccagccttgcgg |
| M125G | FP (SEQ ID NO: 123) | ccgcaaggctggcggggcctacgtcatcg |
| M125G | RCP (SEQ ID NO: 124) | cgatgacgtaggccccgccagccttgcgg |
| M125I | FP (SEQ ID NO: 125) | ccgcaaggctggcatagcctacgtcatcg |
| M125I | RCP (SEQ ID NO: 126) | cgatgacgtaggctatgccagccttgcgg |
| M125V | FP (SEQ ID NO: 127) | gcaaggctggcgtggcctacgtcatcg |
| M125V | RCP (SEQ ID NO: 128) | cgatgacgtaggccacgccagccttgc |
| M125W | FP (SEQ ID NO: 129) | gcaaggctggctgggcctacgtcatcgag |
| M125W | RCP (SEQ ID NO: 130) | ctcgatgacgtaggcccagccagccttgc |
| Y127E | FP (SEQ ID NO: 131) | caaggctggcatggccgaggtcatcgagg |
| Y127E | RCP (SEQ ID NO: 132) | cctcgatgacctcggccatgccagccttg |
| V128F | FP (SEQ ID NO: 133) | ggctggcatggcctacnnnatcgaggatctactgcacttc |
| V128F | RCP (SEQ ID NO: 134) | gaagtgcagtagatcctcgatnnngtaggccatgccagcc |
| L132M | FP (SEQ ID NO: 135) | gcctacgtcatcgaggatatgctgcacttctgccgg |
| L132M | RCP (SEQ ID NO: 136) | ccggcagaagtgcagcatatcctcgatgacgtaggc |
| L132N | FP (SEQ ID NO: 137) | gcctacgtcatcgaggataacctgcacttctgccgg |
| L132N | RCP (SEQ ID NO: 138) | ccggcagaagtgcaggttatcctcgatgacgtaggc |
| L132V | FP (SEQ ID NO: 139) | cgtcatcgaggatgtactgcacttctgccg |

TABLE 2-continued

PCR Primers for Substitution Mutant CfEcR Ligand Binding Domain Construction

| MUTANT | PRIMER (SEQ ID NO:) | PRIMER NUCLEOTIDE SEQUENCE (5' TO 3') |
|---|---|---|
| L132V | RCP (SEQ ID NO: 140) | cggcagaagtgcagtacatcctcgatgacg |
| L132E | FP (SEQ ID NO: 141) | gcctacgtcatcgaggatgaactgcacttctgcc |
| L132E | RCP (SEQ ID NO: 142) | ggcagaagtgcagttcatcctcgatgacgtaggc |
| M219K | FP (SEQ ID NO: 143) | gcatgcaaaactccaacaagtgcatctccctcaag |
| M219K | RCP (SEQ ID NO: 144) | cttgagggagatgcacttgttggagttttgcatgc |
| M219W | FP (SEQ ID NO: 145) | gcatgcaaaactccaactggtgcatctccctcaagct |
| M219W | RCP (SEQ ID NO: 146) | agcttgagggagatgcaccagttggagttttgcatgc |
| M219Y | FP (SEQ ID NO: 147) | ctcggcatgcaaaactccaactattgcatctccctcaagctcaag |
| M219Y | RCP (SEQ ID NO: 148) | cttgagcttgagggagatgcaatagttggagttttgcatgccgag |
| M219A | FP (SEQ ID NO: 149) | catgcaaaactccaacgcgtgcatctccctcaag |
| M219A | RCP (SEQ ID NO: 150) | cttgagggagatgcacgcgttggagttttgcatg |
| L223K | FP (SEQ ID NO: 151) | ctccaacatgtgcatctccaagaagctcaagaacag |
| L223K | RCP (SEQ ID NO: 152) | ctgttcttgagcttcttggagatgcacatgttggag |
| L223R | FP (SEQ ID NO: 153) | ctccaacatgtgcatctcccgcaagctcaagaacag |
| L223R | RCP (SEQ ID NO: 154) | ctgttcttgagcttgcgggagatgcacatgttggag |
| L223Y | FP (SEQ ID NO: 155) | ctccaacatgtgcatctcctacaagctcaagaacag |
| L223Y | RCP (SEQ ID NO: 156) | ctgttcttgagcttgtaggagatgcacatgttggag |
| L234M | FP (SEQ ID NO: 157) | gctgccgcctttcatggaggagatctgggatg |
| L234M | RCP (SEQ ID NO: 158) | catcccagatctcctccatgaaaggcggcagc |
| L234I | FP (SEQ ID NO: 159) | gctgccgcctttcattgaggagatctgggatgtg |
| L234I | RCP (SEQ ID NO: 160) | cacatcccagatctcctcaatgaaaggcggcagc |
| L234R | FP (SEQ ID NO: 161) | ctgccgcctttccgagaggagatctgggatg |
| L234R | RCP (SEQ ID NO: 162) | catcccagatctcctctcggaaaggcggcag |
| L234W | FP (SEQ ID NO: 163) | gctgccgcctttctgggaggagatctgggatgtg |

TABLE 2-continued

PCR Primers for Substitution Mutant CfEcR Ligand Binding Domain Construction

| MUTANT | PRIMER (SEQ ID NO:) | PRIMER NUCLEOTIDE SEQUENCE (5' TO 3') |
|---|---|---|
| L234W | RCP (SEQ ID NO: 164) | cacatcccagatctcctcccagaaaggcggcagc |
| W238P | FP (SEQ ID NO: 165) | ctcgaggagatcccggatgtggcaggacatg |
| W238P | RCP (SEQ ID NO: 166) | catgtcctgccacatccgggatctcctcgag |
| W238E | FP (SEQ ID NO: 167) | cctcgaggagatcgaggatgtggcaggacatg |
| W238E | RCP (SEQ ID NO: 168) | catgtcctgccacatcctcgatctcctcgagg |
| W238L | FP (SEQ ID NO: 169) | ctcgaggagatcttggatgtggcaggacatg |
| W238L | RCP (SEQ ID NO: 170) | catgtcctgccacatccaagatctcctcgag |
| W238M | FP (SEQ ID NO: 171) | cctcgaggagatcatggatgtggcaggacatgtc |
| W238M | RCP (SEQ ID NO: 172) | gacatgtcctgccacatccatgatctcctcgagg |
| W238Y | FP (SEQ ID NO: 173) | cctcgaggagatctacgatgtggcaggacatgtc |
| W238Y | RCP (SEQ ID NO: 174) | gacatgtcctgccacatcgtagatctcctcgagg |

The resulting PCR nucleic acid products encoding the mutant EcR ligand binding domains were then each fused to a GAL4 DNA binding domain as described in Example 1.2 above. The GAL4/mutant EcR receptor constructs were tested for activity by transfecting them into NIH3T3 cells along with VP16/βRXREF-LmRXREF and pFRLuc in the presence of various ligands.

The Gal4-CfEcR-DEF(VYG) mutant was created by inserting an extra glycine at the C-terminal end of EcR substitution mutant V107I/Y127E [CfECR(VY)] by PCR. Essentially, this was done in two steps: PCR-amplification of CfEcR-DEF(VYG) and substitution of the CfEcR(VY) in the vector GAL4-CfEcR DEF(VY) pBIND 1-9 with the PCR-amplified CfEcR-DEF(VYG). The CfEcR-DEF region (with the extra glycine) was amplified by using the vector GAL4-CfEcR DEF(VY) pBIND 1-9 as template and the following PCR primers:

```
                                         (SEQ ID NO: 175)
5EcR-wt
GGAATTCCCGGGGATCCGGCCTGAGTGCGTAGTACCC (SEQ ID NO: 176)
3EcR-gly
CTCTCTGCGGCCGCCTATCCGAGATTCGTGGGGACTCGAGGATAG
```

The PCR product was isolated and digested with Not I (cuts at the 3' end; included in the 3' PCR primer) and Xma I (cuts at the 5' end; present in the 5'PCR primer). This product was ligated to the vector prepared in the following way: GAL4-CfEcR DEF(VY) pBIND 1-9 was digested with Xma I and Not I (the digestion removes the CfEcR-DEF (VY) from the vector). The fragments were separated on 1% agarose gel and the slower migrating vector DNA was purified. After ligation between the vector and the CfEcR-DEF(VYG) fragment described above, the ligation reaction was tranformed into bacteria. The positive colonies were selected by colony PCR using the primers mentioned above. The VYG mutations in the selected clone were confirmed by sequencing.

Example 2

This Example describes the identification of ecdysteroid responsive CfEcR ligand binding domain substitution mutants that exhibit increased activity in response to ecdysteroidal ligand. In an effort to identify substitution mutations in the CfEcR that increase ecdysteroidal ligand activity, Applicants mutated amino acid residues predicted to be critical for ecdysteroid binding and created GAL4/mutantCfEcR-DEF cDNA gene expression cassettes as described in Example 1 above using PCR-mediated site-directed mutagenesis kit. The mutated and the WT cDNAs corresponding to the various switch constructs outlined above in Example were made and tested in GAL4-driven luciferase reporter assays as described below.

Transfections: DNAs were transfected into mouse NIH3T3 cells (ATCC) as follows. Standard methods for culture and maintenance of the cells were followed. Cells were harvested and plated 96-well plates at 2,500 cells per well, in 50 µL of growth medium containing 10% fetal bovine serum (FBS). Twenty-four hours later, the cells were treated with 35 μL of serum-free growth medium containing either dimethylsulfoxide (DMSO; control) or a DMSO solution of ligand. The cells were then transfected using Superfect™ (Qiagen Inc.) transfection reagent. For each well, 0.625 μL of Superfect™ was mixed with 14.2 μL of serum-free growth medium. 0.16 μg of reporter construct and 0.04 μg of each receptor construct were added to the transfection reagent mix. The contents of the transfection mix were mixed in a vortex mixer and let stand at room temperature for 30 minutes. At the end of incubation, 15 μL of transfection mix was added to the cells. The cells were maintained at 37° C. and 5% $CO_2$ for 48 hours in 5% FBS.

Ligands: The ecdysteroidal ligands ponasterone A and 20-hydroxyecdysone were purchased from Sigma Chemical Company and Invitrogen. The non-ecdysteroidal diacylhydrazine ligand N-(2-ethyl-3-methoxybenzoyl)-N'-(3,5-dimethylbenzoyl)-N'-tert-butylhydrazine (RG-102240, GS®-E ligand) is a synthetic stable ecdyecdysteroid ligand that was synthesized at Rohm and Haas Company. The non-ecdysteroidal, diacylhydrazine ligands RG-101691, RG-102362, RG-115840, RG-115853, RG-115855, RG-115859 and RG-115898 were synthesized by RheoGene Inc. The synthesis of RG-101691, RG-102362, RG-115840, RG-115859 and RG-115898 is described below. The synthesis of RG-115853 and RG-115855 is described in co-pending U.S. patent application Ser. No. 10/775,883. The non-ecdysteroidal tetrahydroquinoline ligands RG-120499 and RG-120500 were synthesized by RheoGene, Inc. and were described in co-pending U.S. patent application Ser. No. 10/460,820. All ligands were dissolved in DMSO.

Ligand Synthesis

Preparation of 3,5-Dimethyl-benzoic Acid N-tert-butyl-N'-(3-ethyl-2-methyl-benzoyl)-hydrazide (RG-101691)

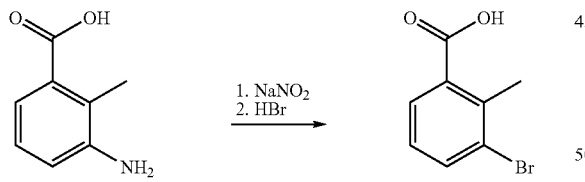

3-Amino-2-methylbenzoic acid (6.16 g) was heated at reflux for 30 minutes in concentrated HBr. The mixture was cooled to 0° C. and treated with a solution of $NaNO_2$ at 0° C. (2.8 g in 5.6 mL $H_2O$). The resultant diazonium salt solution was slowly added to a preheated (60-70° C.) solution of CuBr (3.8 g) in 3.2 mL concentrated HBr. After the addition, the mixture was stirred overnight at room temperature and filtered. The recovered filter cake was washed first with water and then with 10% HCl, and dried in air to yield 6.93 g of 3-bromo-2-methylbenzoic acid as a light purple powdery solid. This material was dissolved in ethyl acetate, washed twice with 5% HCl dried over $Na_2SO_4$, and recrystallized from 4:1 hexanes:ethyl acetate first at room temperature and then under refrigeration. $^1$H NMR (DMSO, 200 MHz), δ (ppm): 7.72 (dd, 2H), 7.2 (t, 1H), 2.5 (s, 3H).

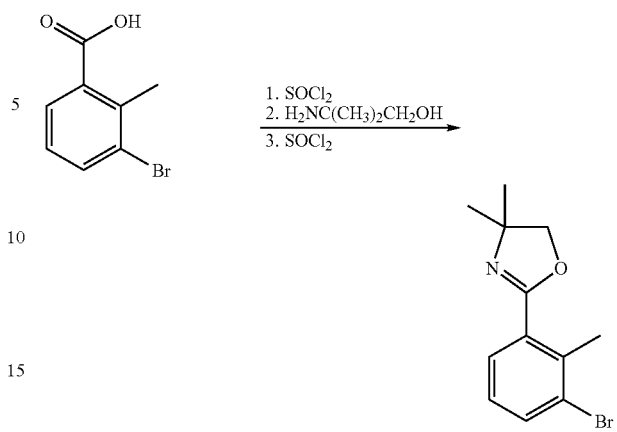

3-Bromo-2-methylbenzoic acid (7.03 g, 32.7 mmol) was refluxed in 10 mL of $SOCl_2$ (98 mmol) and a drop of DMF for 3 hours. Excess $SOCl_2$ was removed in vacuo. The residue was dissolved in 20 mL of $CH_2Cl_2$ and added to an ice-chilled solution of 2-amino-2-methyl-propan-1-ol (8.74 g, 9.36 mL) in 20 mL of $CH_2Cl_2$. The mixture was stirred at room temperature for 18 hours and the solvent was removed in vacuo to leave an oily residue. $SOCl_2$ (7.4 mL, 100 mL, 3 eq.) was added to this residue over a period of one hour, the mixture was stirred an additional 30 min, and then poured into 150 mL of ether. An oily immiscible phase formed and the ether was discarded. The oil was mixed with 100 mL of 20% NaOH, and extracted with 3×150 mL portions of ether. The ether extracts were combined, dried over $MgSO_4$, and the solvent was removed in vacuo to yield a yellow oil. Chromatography on silica gel using 4:1 hexane: ether as eluant yielded 4.87 g of 2-(3-bromo-2-methyl-phenyl)-4,4-dimethyl-4,5-dihydro-oxazole as a colorless oil. (Rf=0.25 (4:1 hexane: ether). $^1$H NMR ($CDCl_3$, 200 MHz), δ (ppm): 7.62 (m, 2H), 7.1 (t, 1H), 4.1 (s, 2H), 2.6 (s, 3H), 1.4 (s, 6H).

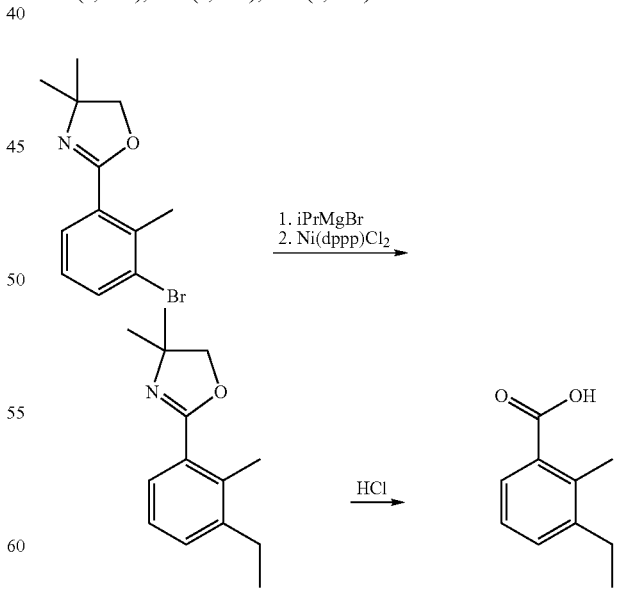

2-(3-bromo-2-methyl-phenyl)-4,4-dimethyl-4,5-dihydro-oxazole (3.4 g, 12.7 mmol) was dissolved in 30 mL of ethyl ether under nitrogen atmosphere in a 100 mL round bottom flask equipped with magnetic stirring, thermometer, and reflux condenser. Ni(dppp)Cl$_2$ (100 mg) was added and the mixture was cooled to 0° C. in an ice bath. Ethyl magnesium bromide (5.5 mL, 3M in ether) was added, the reaction mixture was stirred at 0° C. for 30 minutes, at room temperature for 2½ hours, and finally at reflux for 2 hours. The mixture was then cooled to 0° C., quenched with saturated aqueous NH$_4$Cl. The organic layer was removed and the aqueous layer was extracted with ether. The organic phases were combined and dried over MgSO$_4$. The solvent was removed in vacuo to give 2.84 g 2-(3-ethyl-2-methyl-phenyl)-4,4-dimethyl-4,5-dihydro-oxazole, $^1$H NMR (CDCl$_3$, 200 MHz), δ (ppm): 7.5 (d, 2H), 7.2 (m, 2H), 4.1 (s, 2H), 2.7 (m, 2H), 2.45 (s, 3H), 1.4 (s, 6H), 1.2 (t, 3H), Rf=0.25 (4:1 hexane:ether), containing ca. 5% original aryl bromide. The oxazoline was suspended in 100 mL of 6N HCl and refluxed for 5 hours with vigorous stirring. The mixture was allowed to cool to room temperature, whereupon 3-ethyl-2-methyl-benzoic acid crystallized: 1.74 g, m.p. 96-98° C., $^1$H NMR (CDCl$_3$, 200 MHz), δ (ppm): 7.85 (d, 1H), 7.4 (d, 1H), 7.22 (t, 1H), 2.7 (q, 2H), 2.6 (s, 3H), 1.21 (t, 3H). An additional 110 mg was recovered by ether extraction of the aqueous phase.

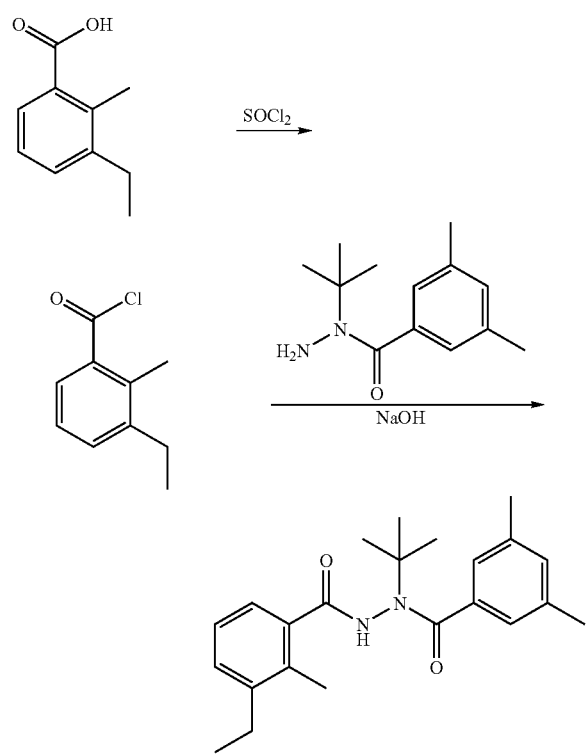

3-Ethyl-2-methyl-benzoic acid (0.517 g) was refluxed in 3 mL of thionyl chloride with a drop of DMF for several hours. Thionyl chloride was removed in vacuo to yield 0.89 g (4.48 mmol) of 3-ethyl-2-methyl-benzoyl chloride. The acid chloride was dissolved in 5 mL of CH$_2$Cl$_2$ and added slowly and simultaneously but separately with 5 mL of aqueous NaOH (0.30 g, 7.5 mmol) to a solution of 3,5-dimethyl-benzoic acid N-tert-butyl-hydrazide (0.96 g, 4.36 mmol) dissolved in 10 mL of CH$_2$Cl$_2$ prechilled to −5° C. During the addition, the temperature was kept below 5° C. The mixture was allowed to warm slowly to room temperature and was stirred overnight. The organic layer was removed and the aqueous layer was extracted with CH$_2$Cl$_2$. The organic extracts were combined, dried, and solvent was removed in vacuo to give 1.5 g crude product. This residue was extracted with 100 mL of hexanes under reflux, and the hot extract was decanted from an oily residue and allowed to cool to room temperature, whereupon 3,5-dimethyl-benzoic acid N-tert-butyl-N'-(3-ethyl-2-methyl-benzoyl)-hydrazide crystallized (0.56 g, m.p. 167-169° C., $^1$H NMR (CDCl$_3$, 200 MHz), δ (ppm): 7.43 (s, 1H), 7.18 (m, 1H), 7.1 (s, 2H), 7.03 (s, 1H), 7.0 (m, 1H), 6.35 (d, 1H), 2.58 (q, 2H), 2.3 (s, 6H), 1.95 (s, 3H), 1.6 (s, 9H), 1.15 (t, 3H). Dissolution of the oily residue and crystallization yielded a second crop of less pure material, 0.21 g.

Preparation of 3,5-Dimethyl-benzoic Acid N-tert-butyl-N'-(3-isopropyl-2-methyl-benzoyl)-hydrazide (RG-102362)

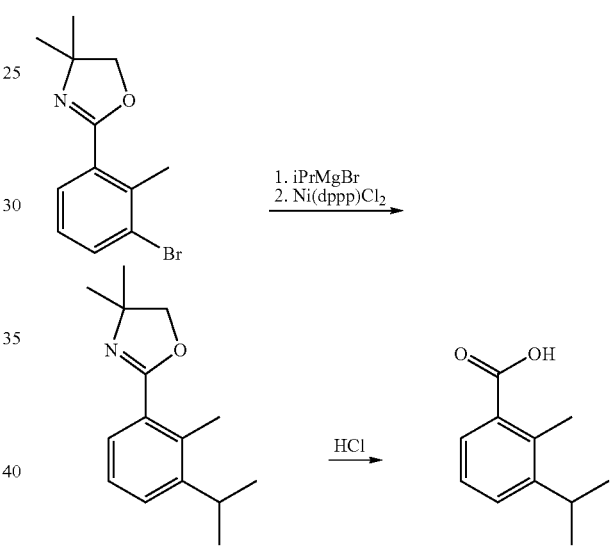

A dry 3-neck 250 mL round bottom flask equipped with magnetic stirring and held under a nitrogen atmosphere was charged with 5.0 g 2-(3-bromo-2-methyl-phenyl)-4,4-dimethyl-4,5-dihydro-oxazole, 60 mL anhydrous THF, and 100 mg Ni(dppp)Cl$_2$. The mixture was cooled to 15° C., and isopropyl magnesium chloride (11 mL, 2M in ethyl ether) was added. A mild exotherm took place, and the mixture darkened slightly. The reaction was stirred overnight at room temperature, at which point $^1$H NMR indicated 50% completion. Addition of ca 75 mg Ni(dppp)Cl$_2$ and reflux for 3 hours resulted in no further progression of the reaction. The mixture was cooled to 15° C., and an additional 13 mL of isopropyl magnesium chloride (2M in ethyl ether) and 100 mg of nickel catalyst were added and the mixture was stirred overnight at room temperature. The reaction was quenched with saturated aqueous NH$_4$Cl, the organic layer was removed, the aqueous layer was extracted, and the organic phases were combined and dried. The solvent was removed in vacuo to yield 3.84 g crude product as a yellow oil. Column chromatography on silica gel using 4:1 hexanes: ether as eluant yielded 0.79 g of 2-(3-isopropyl-2-methyl-phenyl)-4,4-dimethyl-4,5-dihydrooxazole as a colorless oil. $^1$H NMR (CDCl$_3$, 200 MHz), δ (ppm): 7.5 (d, 1H), 7.37 (d, 1H), 7.22 (t, 1H), 4.13 (s, 2H), 3.23 (m, 1H), 2.5 (s, 3H), 1.45 (s, 6H), 1.22 (d, 6H). The oxazoline was suspended in 34 mL of 6N HCl and refluxed in an oil bath for 6 hours. The mixture was cooled and extracted with CH$_2$Cl$_2$. The extract was dried over Na$_2$SO$_4$ and evaporated to yield 0.76 g of 3-isopropyl-2-methyl-benzoic acid, suitably pure for the next step. $^1$H NMR (CDCl$_3$, 300 MHz), δ (ppm): 7.8 (d, 1H), 7.48 (d, 1H), 7.3 (t, 1H), 3.3 (m, 1H), 2.55 (s, 3H), 1.2 (d, 6H).

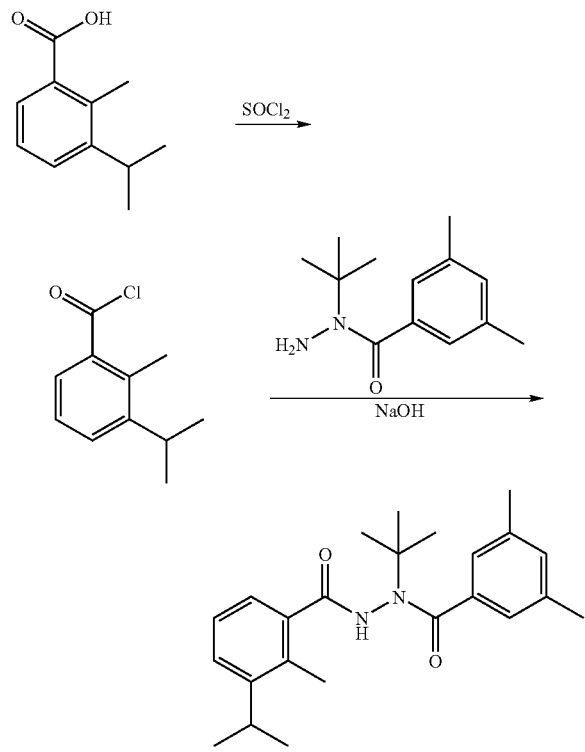

3-Isopropyl-2-methyl-benzoic acid (0.75 g) was refluxed in ca. 3 mL of thionyl chloride with a drop of DMF fro several hours and thionyl chloride was removed in vacuo to yield 3-isoproyl-2-methyl-benzoyl chloride. The acid chloride was dissolved in 5 ML of CH$_2$Cl$_2$ and added slowly and simultaneously but separately with 5 mL of aqueous NaOH (0.265 g, 6.6 mmol) to a solution of 3,5-dimethyl-benzoic acid N-tert-butyl-hydrazide (0.973 g, 4.4 mmol) dissolved in 10 mL of CH$_2$Cl$_2$ prechilled to −5° C. During the addition, the temperature was kept below 5° C. The mixture was allowed to warm slowly to room temperature and was stirred overnight. The organic layer was removed and the aqueous layer was extracted with CH$_2$Cl$_2$. The organic extracts were combined, dried, and solvent was removed in vacuo to give 1.61 g of crude product as a yellow oil. This material was chromatographed on silica gel using 4:1 hexanes: ethyl acetate as eluant, and subsequently triturated from 1:1 hexane: ether, yielding 3,5-dimethyl-benzoic acid N-tert-butyl-N'-(3-isoproyl-2-methyl-benzoyl)-hydrazide, after arduous removal of ether in a vacuum oven at 60° C. (0.35 g, m.p. 182.5° C. $^1$H NMR (CDCl$_3$, 200 MHz), δ (ppm): 7.6 (s, 1H), 7.25 (d, 1H), 7.1 (s, 2H), 7.05 (s, 1H), 7.0 (m, 1H), 6.3 (d, 1H), 3.1 (m, 1H), 2.3 (s, 6H), 1.95 (s, 3H), 1.6 (s, 9H), 1.18 (m, 6H).

Preparation of 3,5-dimethyl-benzoic Acid N'-(5-ethyl-2,3-dihydro-benzo[1,4]dioxine-6-carbonyl)-N-(1-ethyl-2,2-dimethyl-propyl)-hydrazide (RG-115858)

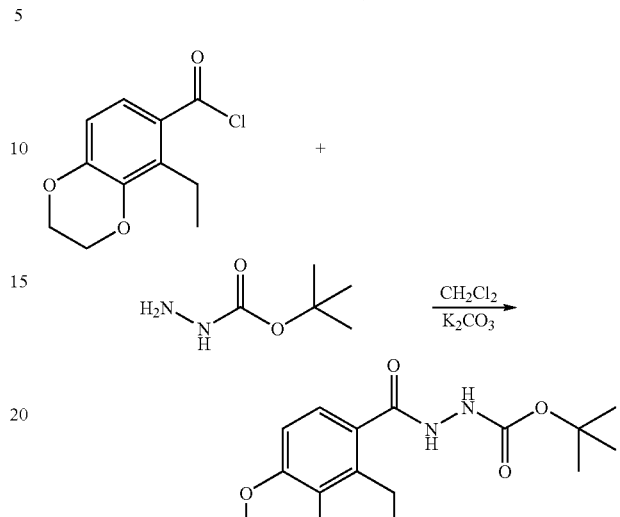

2.38 g (18 mmol) of t-butyl carbazate were dissolved in 50 mL of CH$_2$Cl$_2$ in a 250 mL round bottom flask and cooled to 0° C. An aqueous K$_2$CO$_3$ solution was prepared (4.15 g K$_2$CO$_3$/35 mL H$_2$O) and added to the reaction mixture which was again cooled to 0° C. 3.63 g (16 mmol) of 5-ethyl-2,3-dihydro-benzo[1,4]dioxine-6-carbonyl chloride were dissolved in 40 mL of CH$_2$Cl$_2$ and added from a separatory funnel, drop-wise over 15 min. The reaction mixture was stirred at room temperature for 3 days. The reaction mixture was transferred to a separatory funnel with CH$_2$Cl$_2$ and H$_2$O. The water phase was thoroughly extracted with CH$_2$Cl$_2$. The CH$_2$Cl$_2$ extract was then extracted with 0.5N HCl, dried, and evaporated. The residue was further dried in a vacuum oven to yield 5.15 g of a tan solid of N'-(5-ethyl-2,3-dihydro-benzo[1,4]dioxine-6-carbonyl)-hydrazinecarboxylic acid tert-butyl ester. TLC (1:1 ethyl acetate: hexane) gave a single spot at Rf=0.43 and NMR indicated a very pure product: $^1$H NMR (CDCl$_3$, 500 MHz) δ (ppm): 7.5 (br, 1H), 7.0 (br, 1H), 6.75 (d, 2H), 4.28 (br, 4H), 2.76 (m, 2H), 1.5 (s, 9H), 1.18 (t, 3H).

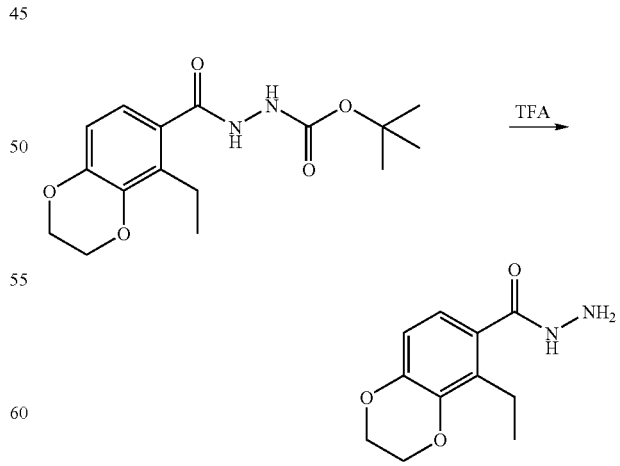

5.15 g (16 mmol) of N'-(5-ethyl-2,3-dihydro-benzo[1,4]dioxine-6-carbonyl)-hydrazinecarboxylic acid tert-butyl ester were added to a 200 mL round bottom flask. About 20 mL of trifluoroacetic acid were added and the reaction mixture was stirred at room temperature for 24 hours. Then about 40 mL of water were added, followed by the slow addition of cold 10% NaOH/H₂O, with stirring, until the acid was neutralized (pH~14). The reaction mixture was transferred to a separatory funnel and extracted with ethyl acetate by shaking gently (caution: gas evolution). The ethyl acetate extract was dried and evaporated to yield 5.51 g of a pale, viscous yellow semi-solid. The material was then placed in a 50° C. vacuum oven for about 1 hour to yield 4.62 g of 5-ethyl-2,3-dihydro-benzo[1,4]dioxine-6-carboxylic acid hydrazide. The t-Boc cleavage is best accomplished with neat trifluoroacetic acid; use of adjunctive solvents always resulted in much lower yields. $^1$H NMR (CDCl$_3$, 500 MHz) δ (ppm): 7.0 (br, 1H), 6.83 (m, 1H), 6.71 (m, 1H), 4.28 (br s, 4H), 2.76 (m, 2H), 1.6 (br, 2H), 1.17 (t, 3H).

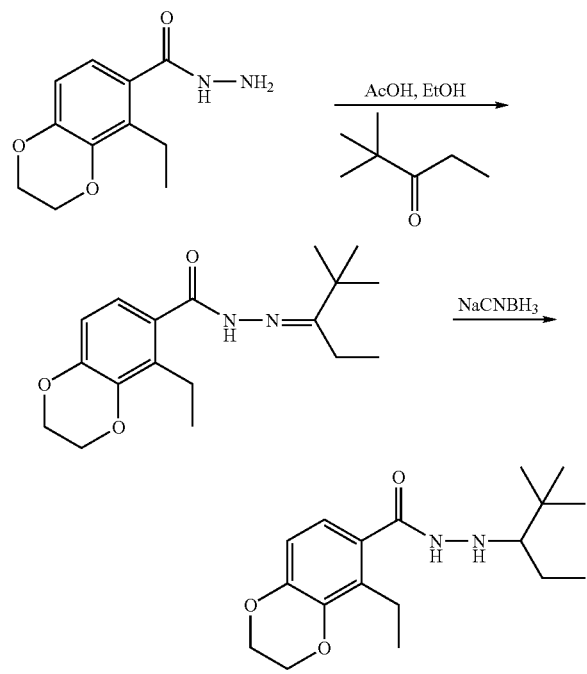

1.12 g (5.1 mmol) of 5-ethyl-2,3-dihydro-benzo[1,4]dioxine-6-carboxylic acid hydrazide, 1.37 g (12 mmol) of 2,2 dimethyl pentanone-3, 30 mL of ethanol, and 20 drops of glacial acetic acid were refluxed for 6 hours to generate 5-ethyl-2,3-dihydro-benzo[1,4]dioxine-6-carboxylic acid (1-ethyl-2,2-dimethyl-propylidene)-hydrazide, which was used in situ. To the cooled reaction mixture, was added 3 mL of glacial acetic acid and 0.63 g (10 mmol) of NaCNBH₃. The reaction was stirred at room temperature for 24 hours. 25 mL of water were added and most of the alcohol was removed on a rotary evaporator. Then 10% NaOH/H₂O was added until the reaction mixture was basic. The product was extracted with ethyl acetate, which was then dried and evaporated to give 1.61 g of residue. Pure 5-ethyl-2,3-dihydro-benzo[1,4]dioxine-6-carboxylic acid N'-(1-ethyl-2,2-dimethyl-propyl)-hydrazide was obtained (ca. 0.77 g) by column chromatography on silica gel, eluting with 25% ethyl acetate/hexane. TLC: Rf=0.53, 1:1 ethyl acetate: hexane). $^1$H NMR (CDCl$_3$, 500 MHz) δ (ppm): 7.1 (br s, 1H), 6.8 (d, 1H), 6.7 (d, 1H), 4.27 (m, 4H), 2.8 (m, 2H), 2.4 (m, 1H), 1.7 (m, 1H), 1.3 (m, 1H), 1.2 (t, 3H), 1.15 (t, 3H), 0.97 (s, 9H).

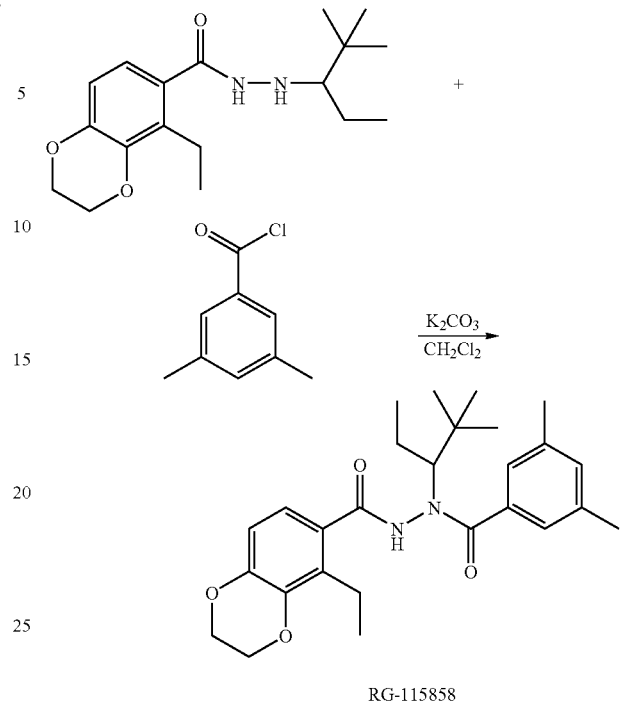

RG-115858

0.214 g (0.70 mmol) of 5-ethyl-2,3-dihydro-benzo[1,4] dioxine-6-carboxylic acid N'-(1-ethyl-2,2-dimethyl-propyl)-hydrazide, 151 mg (0.9 mmol) of 3,5 dimethylbenzoyl chloride, 7 mL of 25% K₂CO₃/H₂O and 7 mL of CH₂Cl₂ were added to a 20 mL vial and stirred at room temperature for 24 hours. The reaction mixture was transferred to a separatory funnel, and dilute NaHCO₃ and CH₂Cl₂ were added. The CH₂Cl₂ layer was separated and the water layer extracted twice with CH₂Cl₂. The CH₂Cl₂ extracts were dried over MgSO₄ and evaporated to yield 0.59 g of a white residue. Purification by column chromatography and elution with 15 mL of 20% ethyl acetate/hexane yielded about 350 mg of 3,5-dimethyl-benzoic acid N'-(5-ethyl-2,3-dihydro-benzo[1,4]dioxine-6-carbonyl)-N-(1-ethyl-2,2-dimethyl-propyl)-hydrazide (95% pure by TLC: Rf=0.56, 1:1 ethyl acetate:hexane). $^1$H NMR (CDCl$_3$, 500 MHz) δ (ppm): 7.05 (s, 1H), 7.0 (s, 2H), 6.6 (d, 1H), 6.27 (d, 1H), 4.65 (d, 1H), 4.25 (s, 4H), 2.9 (m, 1H), 2.3 (s, 6H), 2.0 (m, 1H), 1.55-1.7 (m, 2H), 1.25 (m, 3H), 0.9-1.2 (3s, 9H), 0.9 (t, 3H).

Preparation of 3,5-dimethoxy-4-methyl-benzoic acid N-(1-tert-butyl-3,4,4-trimethyl-pent-2-enyl)-N'-(5-ethyl-2,3-dihydro-benzo[1,4]dioxine-6-carbonyl)-hydrazide (RG115898)

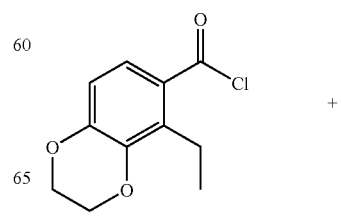

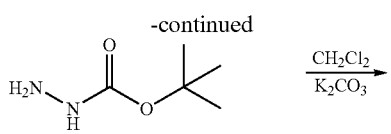

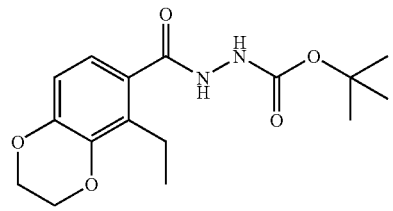

yields. $^1$H NMR (CDCl$_3$, 500 MHz) δ (ppm): 7.0 (br, 1H), 6.83 (m, 1H), 6.71 (m, 1H), 4.28 (br s, 4H), 2.76 (m, 2H), 1.6 (br, 2H), 1.17 (t, 3H).

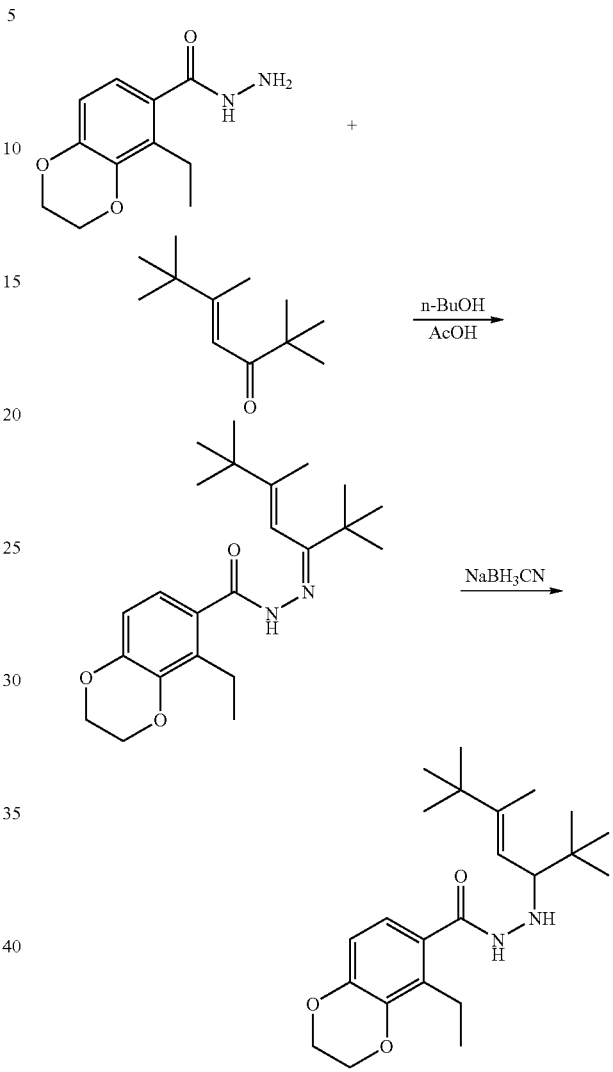

2.38 g (18 mmol) of t-butyl carbazate were dissolved in 50 mL of CH$_2$Cl$_2$ in a 250 mL round bottom flask and cooled to 0° C. An aqueous K$_2$CO$_3$ solution was prepared (4.15 g K$_2$CO$_3$/35 mL H$_2$O) and added to the reaction mixture which was again cooled to 0° C. 3.63 g (16 mmol) of 5-ethyl-2,3-dihydro-benzo[1,4]dioxine-6-carbonyl chloride were dissolved in 40 mL of CH$_2$Cl$_2$ and added from a separatory funnel, drop-wise over 15 min. The reaction mixture was stirred at room temperature for 3 days. The reaction mixture was transferred to a separatory funnel with CH$_2$Cl$_2$ and H$_2$O. The water phase was thoroughly extracted with CH$_2$Cl$_2$. The CH$_2$Cl$_2$ extract was then extracted with 0.5N HCl, dried, and evaporated. The residue was further dried in a vacuum oven to yield 5.15 g of a tan solid of N'-(5-ethyl-2,3-dihydro-benzo[1,4]dioxine-6-carbonyl)-hydrazinecarboxylic acid tert-butyl ester. TLC (1:1 ethyl acetate: hexane) gave a single spot at Rf=0.43 and NMR indicated a very pure product: $^1$H NMR (CDCl$_3$, 500 MHz) δ (ppm): 7.5 (br, 1H), 7.0 (br, 1H), 6.75 (d, 2H), 4.28 (br, 4H), 2.76 (m, 2H), 1.5 (s, 9H), 1.18 (t, 3H).

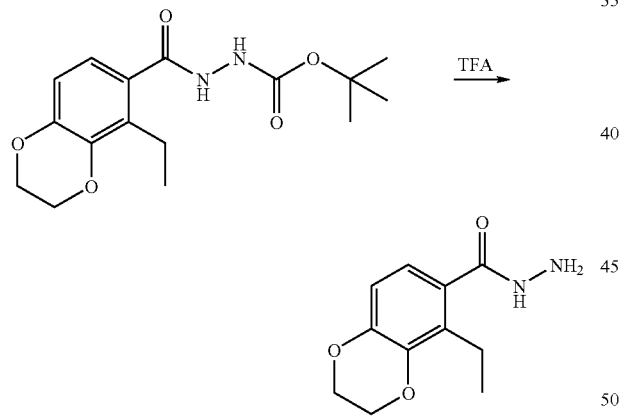

5.15 g (16 mmol) of N'-(5-ethyl-2,3-dihydro-benzo[1,4]dioxine-6-carbonyl)-hydrazinecarboxylic acid tert-butyl ester were added to a 200 mL round bottom flask. About 20 mL of trifluoroacetic acid were added and the reaction mixture was stirred at room temperature for 24 hours. Then about 40 mL of water were added, followed by the slow addition of cold 10% NaOH/H$_2$O, with stirring, until the acid was neutralized (pH~14). The reaction mixture was transferred to a separatory funnel and extracted with ethyl acetate by shaking gently (caution: gas evolution). The ethyl acetate extract was dried and evaporated to yield 5.51 g of a pale, viscous yellow semi-solid. The material was then placed in a 50° C. vacuum oven for about 1 hour to yield 4.62 g of 5-ethyl-2,3-dihydro-benzo[1,4]dioxine-6-carboxylic acid hydrazide. The t-Boc cleavage is best accomplished with neat trifluoroacetic acid; use of adjunctive solvents always resulted in much lower 2,2,5,6,6-Pentamethyl-hept-4-en-3-one (1.48 g, 8.1 mmol) was dissolved in n-butyl alcohol (20 mL). Then 5-ethyl-2,3-dihydro-benzo[1,4]dioxine-6-carboxylic acid hydrazide (1.80 g, 8.1 mmol) and 10 drops of glacial acetic acid were added. The reaction mixture was refluxed for 20 hours (required for complete reaction) and monitored by TLC. To a solution of the intermediate 5-ethyl-2,3-dihydro-benzo[1,4]dioxine-6-carboxylic acid (1-tert-butyl-3,4,4-trimethyl-pent-2-enylidene)-hydrazide were added 1.8 mL glacial acetic acid and 1.02 g (16.2 mmol) of sodium cyanoborohydride. The reaction was refluxed for three hours. The reaction was cooled and 50 mL of water and 10% aqueous NaOH were added until the reaction was basic (pH=ca. 14). Most of the alcohol was removed on a rotary evaporator and the residue was extracted with EtOAc. The aqueous extract was dried and concentrated to constant weight, yielding 4 g of a viscous material. 2.3 g pure 5-ethyl-2,3-dihydro-benzo[1,4]dioxine-6-carboxylic acid N'-(1-tert-butyl-3,4,4-trimethyl-pent-2-enyl)-hydrazide was obtained (yellow oil, R$_f$=0.30 in 25% EtOAc in n-Hexane, yield 73%) by column chromatography on silica gel. $^1$H NMR (400 MHz, CDCl$_3$) δ (ppm): 7.42 (br, 1H), 6.80 (d, J=8.4 Hz, 1H), 6.71 (d, J=8.4 Hz, 1H), 6.17 (br, 1H), 5.30 (dd, J=0.8, 10 Hz, 1H), 4.33-4.29 (m, 4H), 3.68 (d, J=10 Hz, 1H), 2.80 (m, 2H), 1.72 (s, 3H), 1.21 (s, 3H), 1.12 (s, 9H), 1.05 (s, 9H).

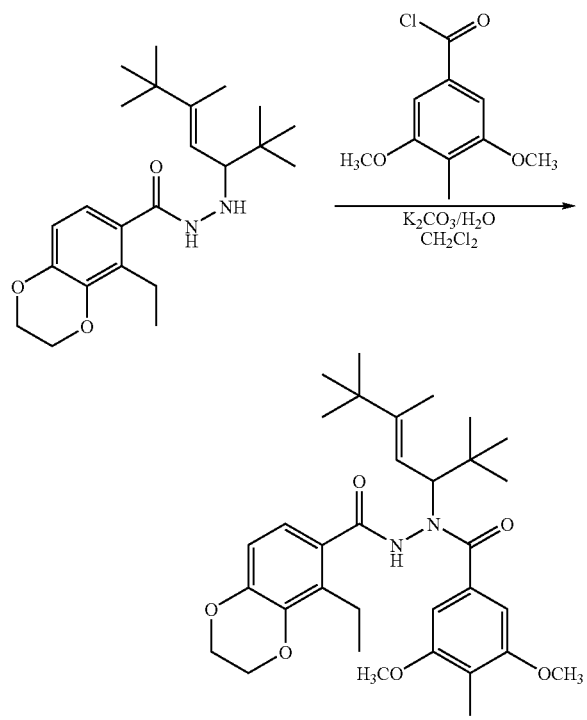

5-Ethyl-2,3-dihydro-benzo[1,4]dioxine-6-carboxylic acid N'-(1-tert-butyl-3,4,4-trimethyl-pent-2-enyl)-hydrazide (150 mg, 0.39 mmol) and 3,5-dimethoxy-4-methylbenzoyl chloride (83 mg, 0.39 mmol) were dissolved in 5 mL CH$_2$Cl$_2$. 5 mL of 25% K$_2$CO$_3$ were added, and the reaction mixture was stirred at room temperature overnight. The reaction was monitored by TLC. The phases were separated, adding additional CH$_2$Cl$_2$ and/or water as needed to aid manipulation. The CH$_2$Cl$_2$ layer was dried and solvent was removed in vacuo to provide 210 mg of crude product. This material was purified by silica gel column chromatography, eluting with a step gradient of 10-25% ethyl acetate in hexane to yield 3,5-dimethoxy-4-methyl-benzoic acid N-(1-tert-butyl-3,4,4-trimethyl-pent-2-enyl)-N'-(5-ethyl-2,3-dihydro-benzo[1,4]dioxine-6-carbonyl)-hydrazide RG115898 (83 mg, R$_f$=0.19 in 25% ethyl acetate in n-hexane, yield 38%). $^1$H NMR (400 MHz, DMSO-d6) δ (ppm): 10.19 (s, 1H), 6.75 (d, J=8.0 Hz, 1), 6.69 (s, 2H), 6.61 (d, J=8.0 Hz, 1H), 5.43 (d, J=10.0 Hz, 1H), 5.41 (d, 14.4 Hz, 1H), 4.30-4.20 (m, 4H), 3.80 (s, 6H), 2.21-2.15 (m, 1H), 2.01 (s, 3H), 1.81 (m, 1H), 1.76-1.64 (m, 1H), 1.06 (s, 9H), 1.00 (s, 9H), 0.70 (t, J=7.6 Hz, 3H).

Preparation of 3,5-dimethyl-benzoic acid N-(1-tert-butyl-pentyl)-N'-(4-ethyl-benzoyl)-hydrazide (RG-115840)

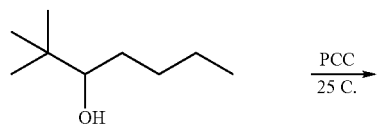

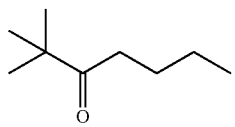

2,2-Dimethyl-heptan-3-ol (0.23 mol) was dissolved in 350 mL of CH$_2$Cl$_2$ in a 500 mL round bottom flask with a magnetic stirbar. The flask was partially cooled with ice. 76.6 g (0.355 mol) of pyridinium chlorochromate was added, while vigorously stirring. The reaction turned black and warmed up slightly. The reaction mixture was stirred at room temperature for 24 hours. The solution was decanted away from the black sludge, which was rinsed with hexane. The organic extracts were combined and chromatographed directly on silica gel. (Note: only silica has been found to trap and remove the reduced non-reacted chromium compounds). The product, 2,2-dimethyl-heptan-3-one, eluted with CH$_2$Cl$_2$/hexane and in a subsequent 10% ethyl acetate/hexane fraction to yield 29.19 g of product at 88% yield. $^1$H NMR (CDCl$_3$, 500 MHz) δ (ppm): 2.48 (t, 2H), 1.54 (m, 2H), 1.28 (m, 2H), 1.13 (s, 9H), 0.90 (m, 3H).

Preparation of 4-ethyl-benzoic Acid N'-(1-tert-butyl-pentyl)-hydrazide

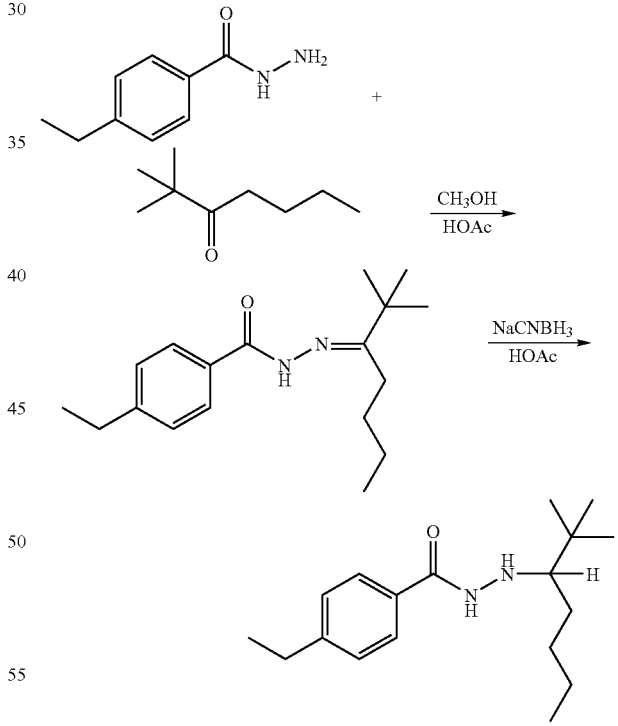

4-Ethyl-benzoic acid hydrazide (1.64 g, 10 mmol) were dissolved in 12.5 mL methanol. One drop of acetic acid was then added, followed by 1.55 g 2,2-dimethyl-heptan-3-one. The mixture was stirred at room temperature for several days, at which time 2.1 mL acetic acid and 667 mg NaBH$_3$CN were added. After stirring for ca. 7 hours, the methanol was removed in vacuo. The residual product was diluted with ca. 20 mL of water and extracted with methylene chloride. The extracts were dried over MgSO$_4$, filtered from solids, and solvent was removed in vacuo to provide 1.8 g crude product. This material was purified by column chromatography on silica gel, eluting with a 100% hexanes-100% ethyl ether gradient. 4-Ethyl-benzoic acid N'-(1-tert-butyl-pentyl)-hydrazide was recovered in 45% yield (1.32 g).

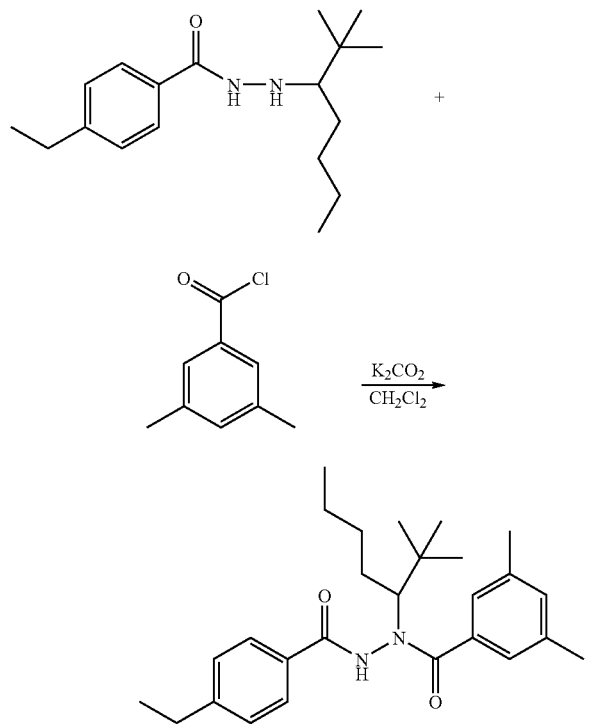

4-Ethyl-benzoic acid N'-(1-tert-butyl-pentyl)-hydrazide (145.2 mg, 0.5 mmol) was dissolved in 5 mL methylene chloride and 1.5 mmol PS-NMM (804 mg, a —SO2NH $(CH_2)_3$-morpholine functionalized polystyrene resin available from Argonaut Technologies, San Carlos, Calif.) was added. The mixture was diluted with 3 ml methylene chloride to generate a stirrable suspension. 3,5-dimethylbenzoyl chloride (0.5 mmol, 74 mL) was added and the mixture was stirred overnight. The following day, 1 mmol (775 mg) of AP-NCO resin (isocyanate-functionalized resin available from Argonaut Technologies, San Carlos, Calif.) and 1 mmol (401.6 mg) of AP-trisamine (polystyrene-$CH_2NHCH_2CH_2NH$ $(CH_2CH_2NH_2)_2$ resin available from Argonaut Technologies, San Carlos, Calif.) were added with 3 mL methylene chloride to scavenge remaining starting material. The mixture was stirred for 4 hours, the resins were filtered away, and the filtrate was dried to provide 191 mg crude product which indicated one spot by TLC analysis. This material was purified by flash chromatography on silica gel using a gradient of 100% hexane-100% ethyl ether. Yield: 50 mg (ca. 23%) 3,5-dimethyl-benzoic acid N-(1-tert-butyl-pentyl)-N'-(4-ethyl-benzoyl)-hydrazide. $^1$H NMR (CDCl$_3$, 400 MHz) δ (ppm): 7.8+7.5 (br/br, 1H), 7.4-6.9 (m, 7H), 4.7+3.6 (m/m, 1H), 2.65 (m, 2H), 2.38+2.28 (s/s, 6H), 1.9+1.75 (br, 2H), 1.4-1.2 (br, m, 7H), 1.1 (br s, 9H), 0.95 (br s, 3H).

Reporter Assays: Cells were harvested 40 hours after adding ligands. 125 μL of passive lysis buffer (part of Dual-luciferase™ reporter assay system from Promega Corporation) were added to each well of the 24-well plate. The plates were placed on a rotary shaker for 15 minutes. Twenty μL of lysate were assayed. Luciferase activity was measured using Dual-luciferase™ reporter assay system from Promega Corporation following the manufacturer's instructions. Fold induction (FI) activities were calculated by dividing relative light units ("RLU") in ligand treated cells with RLU in DMSO treated cells (untreated control).

Example 3

This Example describes the identification of CfEcR ligand binding domain substitution mutants that are generally ecdysteroid responsive that exhibit increased activity in response to ecdysteroids. In an effort to identify substitution mutations in the CfEcR that increase ecdysteroid activity, Applicants mutated amino acid residues and created GAL4/mutantCfEcR-DEF cDNA gene expression cassettes as described in Example 1 above using PCR-mediated site-directed mutagenesis kit. The mutated and the WT cDNAs corresponding to the various switch constructs outlined above in Example 1.1 and 1.2 were made and tested in a GAL4-driven luciferase reporter assay as described in Example 2.

Specific amino acid residues were identified that, when substituted, yield a mutant ecdysone receptor that exhibits increased activity in response to an ecdysteroid ligand. The effect of an amino acid substitution at amino acid residue 119 of SEQ ID NO: 1 on the activity of the mutated CfEcR-DEF receptor is presented in Table 3a as a fold increase over Gal4/wild-type CfEcR-DEF (WT) switch activity. The effect of an amino acid substitution at amino acid residue 96 of SEQ ID NO: 1 and double amino acid substitution at amino residues 96 and 119 on the activity of the mutated CfEcR-DEF receptor is presented in Table 3b as $EC_{50}$ and relative maximum fold induction. $EC_{50}$s were calculated from dose response data using a three-parameter logistic model. Relative Max FI was determined as the maximum fold induction of the tested ligand (an embodiment of the invention) observed at any concentration relative to the maximum fold induction of GS®-E ligand (RG-102240; 3,5-dimethyl-benzoic acid N-tert-butyl-N'-(2-ethyl-3-methoxy-benzoyl)-hydrazide) observed at any concentration.

TABLE 3a

| CfEcR-DEF mutant that shows increased ecdysteroid activity Fold increase over WT | |
|---|---|
| | N119F |
| 1.6 nM GS ®-E ligand (RG-102240) | 1.22 |
| 8 nM GS ®-E ligand (RG-102240) | 0.73 |
| 40 nM GS ®-E ligand (RG-102240) | 0.06 |
| 200 nM GS ®-E ligand (RG-102240) | 0.01 |
| 1 μM GS ®-E ligand (RG-102240) | 0.08 |
| 5 μM GS ®-E ligand (RG-102240) | 0.59 |
| 1.6 nM PonA | 1.33 |
| 8 nM PonA | 1.7 |
| 40 nM PonA | 9.42 |
| 200 nM PonA | 6.50 |
| 1 μM PonA | 3.00 |

TABLE 3b

CfEcR-DEF mutants that shows increased ecdysteroid activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| V96S | EC50 (µM) | 1.14 | 0.87 | 2.07 | >33 | >33 | >33 | ~2 |
| V96S | Rel Max FI | 1 | 0.9 | 0.57 | 0 | 0 | 0.02 | 0.92 |
| N119F/V96T | EC50 (µM) | ~8 | 3.63 | ~10 | ~20 | >33 | ~8 | ~0.3 |
| N119F/V96T | Rel Max FI | 1 | 0.13 | 0.19 | 0.1 | 0.02 | 0.46 | 2.02 |

As seen in Tables 3a and 3b, the activity of ecdysteroids was increased significantly when the CfEcR ligand binding domain was mutated at amino acid residues 96 or 119 of SEQ ID NO: 1 and double mutated at amino acid residues 96 and 119 of SEQ ID NO: 1, indicating that these residues are important residues in the ligand binding pocket of CfEcR.

Example 4

This Example describes the identification of additional CfEcR ligand binding domain substitution mutants that are generally non-ecdysteroid diacylhydrazine responsive that exhibit increased activity in response to diacylhydrazine ligands. In an effort to identify substitution mutations in the CfEcR that increase diacylhydrazine ligand activity Applicants mutated amino acid residues predicted to be critical for ecdysteroid binding and created GAL4/mutantCfEcR-DEF cDNA gene expression cassettes as described in Example 1 above using PCR-mediated site-directed mutagenesis kit. The mutated and the WT cDNAs corresponding to the various switch constructs outlined above in Example 1.1 and 1.2 were made and tested in GAL4-driven luciferase reporter assays as described in Example 2.

Specific amino acid residues were identified that, when substituted, yield mutant ecdysone receptors that exhibit increased activity in response to non-ecdysteroid diacylhydrazine ligands. The effect of an amino acid substitution at amino acid residue 48, 52, 54, 109, 110, 125, 132 and 223 of SEQ ID NO: 1 and a double substitution at amino acid residues 52 and 110 of SEQ ID NO: 1 on the activity of the mutated CfEcR-DEF receptor is presented in Tables 4a and 4b as $EC_{50}$ and relative maximum fold induction. $EC_{50}$s were calculated from dose response data using a three-parameter logistic model. Relative Max FI was determined as the maximum fold induction of the tested ligand (an embodiment of the invention) observed at any concentration relative to the maximum fold induction of GS®-E ligand (3,5-dimethylbenzoic acid N-tert-butyl-N'-(2-ethyl-3-methoxy-benzoyl)-hydrazide) observed at any concentration.

TABLE 4a

CfEcR mutants that show increased diacylhydrazine ligand activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| A110E | EC50(µM) | 0.59 | 0.85 | 1.02 | >33 | >33 | >33 | ~10 |
| A110E | Rel Max FI | 1 | 1.03 | 0.78 | 0 | 0.01 | 0 | 1.09 |
| A110N | EC50(µM) | 1.41 | 0.88 | 0.72 | >33 | >33 | >33 | >33 |
| A110N | Rel Max FI | 1 | 0.99 | 0.86 | 0 | 0 | 0 | 0 |
| F109M | EC50(µM) | 0.66 | 0.65 | 0.82 | >33 | ~20 | >33 | ~20 |
| F109M | Rel Max FI | 1 | 0.75 | 0.6 | 0.04 | 0.05 | 0 | 0.16 |
| A110P | EC50(µM) | 0.55 | 0.67 | 0.77 | >33 | >33 | >33 | >33 |
| A110P | Rel Max FI | 1 | 0.89 | 0.64 | 0 | 0 | 0 | 0 |
| F48Y | EC50(µM) | 1.27 | 0.93 | 0.59 | >33 | >33 | >33 | ~10 |
| F48Y | Rel Max FI | 1 | 0.69 | 0.48 | 0 | 0 | 0 | 0.33 |
| F48W | EC50(µM) | ~1 | 1.53 | 0.77 | >33 | >33 | >33 | ~10 |
| F48W | Rel Max FI | 1 | 0.74 | 0.51 | 0 | 0 | 0 | 0.65 |
| F48L | EC50(µM) | 0.46 | 0.3 | 0.56 | >33 | >33 | >33 | ~10 |
| F48L | Rel Max FI | 1 | 0.81 | 0.53 | 0 | 0 | 0 | 0.59 |
| M54T | EC50(µM) | 0.08 | 0.03 | 0.05 | >33 | >33 | >33 | 9.46 |
| M54T | Rel Max FI | 1 | 0.71 | 0.66 | 0 | 0 | 0 | 0.5 |
| T52L | EC50(µM) | ~0.5 | 0.21 | 0.33 | >33 | >33 | >33 | 5.03 |
| T52L | Rel Max FI | 1 | 0.74 | 0.61 | 0 | 0 | 0 | 0.54 |
| T52V/A110P | EC50(µM) | 0.33 | 0.24 | 0.32 | >33 | >33 | >33 | >33 |
| T52V/A110P | Rel Max FI | 1 | 0.66 | 0.94 | 0 | 0 | 0 | 0 |

TABLE 4b

CfEcR mutants that show increased diacylhydrazine ligand activity

| Mutant | | RG-102240 | RG-115840 | RG-115853 | RG-115855 | RG-115859 | RG-115898 |
|---|---|---|---|---|---|---|---|
| F48R | EC50 (μM) | 7.23 | 3.58 | 0.1 | 5.18 | 9.41 | >33 |
| F48R | Rel Max FI | 1 | 2.65 | 5.71 | 1.02 | 1.25 | 0 |
| L132E | EC50 (μM) | 0.41 | 1.67 | 1.54 | 0.45 | 0.08 | 2.15 |
| L132E | Rel Max FI | 1 | 1.56 | 1.12 | 1.15 | 0.51 | 0.34 |
| M125I | EC50 (μM) | 1.36 | 3.02 | 1.53 | 2 | 0.28 | >33 |
| M125I | Rel Max FI | 1 | 0.45 | 0.54 | 0.69 | 0.76 | 0 |
| L223Y | EC50 (μM) | 3.15 | 0.58 | 0.65 | 0.3 | 1.27 | 0.33 |
| L223Y | Rel Max FI | 1 | 1.42 | 0.77 | 1.6 | 0.79 | 0.2 |
| M125G | EC50 (μM) | 14.17 | 2.97 | 0.14 | 0.08 | 5 | 0.08 |
| M125G | Rel Max FI | 1 | 47.96 | 39.41 | 46.54 | 3.14 | 28.81 |
| M125N | EC50 (μM) | 9.88 | 3.3 | 0.5 | 0. > 33 | 8 | 0.94 |
| M125N | Rel Max FI | 1 | 22.56 | 11.64 | 25.3 | 4.11 | 11.57 |

As seen in Tables 4a and 4b, the activity of diacylhydrazines was increased significantly when the CfEcR ligand binding domain was mutated at amino acid residues 48, 52, 54, 109, 110, 125, 132 and 223 of SEQ ID NO: 1 and double mutated at amino acid residues 52 and 110 of SEQ ID NO: 1, indicating that these residues are important residues in the ligand binding pocket of CfEcR.

Example 5

This Example describes the identification of additional CfEcR ligand binding domain substitution mutants that are generally diacylhydrazine and ecdysteroid responsive that exhibit increased activity in response to diacylhydrazine ligand and ecdysteroid. In an effort to identify substitution mutations in the CfEcR that increase diacylhydrazine ligand activity and ecdysteroid ligand activity, Applicants mutated amino acid residues and created GAL4/mutantCfEcR-DEF cDNA gene expression cassettes as described in Example 1 above using PCR-mediated site-directed mutagenesis kit. The mutated and the WT cDNAs corresponding to the various switch constructs outlined above in Example 1.1 and 1.2 were made and tested in GAL4-driven luciferase reporter assays as described in Example 2. The effect of an amino acid substitution at amino acid residue 109, 132, 238 of SEQ ID NO: 1 or substitution at amino acid residues 52, 107 and 127 of SEQ ID NO: 1 or 107, 127 and addition of a glycine at the end of SEQ ID NO: 1 on the activity of the mutated CfEcR-DEF receptor is presented in Table 5.

TABLE 5

CfEcR mutants that show increased diacylhydrazine and ecdysteroid activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| F109W | EC50 (μM) | 0.61 | 0.49 | 1.41 | >33 | >33 | >33 | 4.06 |
| F109W | Rel Max FI | 1 | 0.79 | 0.7 | 0.01 | 0.01 | 0 | 0.08 |
| V107I/Y127E/T52V | EC50 (μM) | 0.06 | 0.02 | <0.01 | >33 | >33 | >33 | ~1 |
| V107I/Y127E/T52V | Rel Max FI | 1 | 0.88 | 0.73 | 0 | 0 | 0.04 | 0.67 |
| V107I/Y127E/G | EC50 (μM) | 0.17 | 0.02 | 0.06 | >33 | >33 | >33 | 1.65 |
| V107I/Y127E/G | Rel Max FI | 1 | 0.85 | 0.81 | 0 | 0 | 0.03 | 0.67 |
| L132M | EC50 (μM) | 0.77 | 0.51 | 0.13 | >33 | >33 | >33 | 5.47 |
| L132M | Rel Max FI | 1 | 0.77 | 0.66 | 0.01 | 0.04 | 0 | 0.57 |
| L132V | EC50 (μM) | 2.32 | 0.66 | 0.29 | >33 | >33 | >33 | 6.56 |
| L132V | Rel Max FI | 1 | 0.77 | 0.74 | 0.01 | 0.04 | 0 | 0.57 |

TABLE 5-continued

CfEcR mutants that show increased diacylhydrazine and ecdysteroid activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| W238P | EC50 (μM) | ~0.4 | 0.65 | 0.29 | >33 | >33 | >33 | ~3.3 |
| W238P | Rel Max FI | 1 | 0.91 | 0.4 | 0.01 | 0.01 | 0 | 0.73 |

As seen in Table 5, both diacylhyrazine and ecdysteroid activities were increased when the CfEcR ligand binding domain was mutated at amino acid residues 48, 51, 52, 54, 96, 120, 125, 128, 132, 234 and 238, indicating that these residues are important residues in the ligand binding pocket of CfEcR.

Example 6

This Example describes the identification of additional CfEcR ligand binding domain substitution mutants that are generally diacylhydrazine and tetrahydroquinoline responsive that exhibit increased activity in response to diacylhydrazine and tetrahydroquinoline ligands. In an effort to identify substitution mutations in the CfEcR that increase diacylhydrazine ligand activity and tetrahydroquinoline ligand activity, Applicants mutated amino acid residues predicted and created GAL4/mutantCfEcR-DEF cDNA gene expression cassettes as described in Example 1 using PCR-mediated site-directed mutagenesis kit. The mutated and the WT cDNAs corresponding to the various switch constructs outlined above in Example 1.1 and 1.2 were made and tested in GAL4-driven luciferase reporter assays as described in Example 2. The effect of triple mutations at amino acid residues 107, 110 and 127 of SEQ ID NO: 1 and double mutations at 107 and 127 of SEQ ID NO: 1 on the activity of the mutated CfEcR-DEF receptor is presented in Table 6.

TABLE 6

CfEcR mutants that show increased diacylhydrazine and tetrahydroquinoline activity

| | | 1 DAH RG-102240 | 2 DAH RG-101691 | 3 DAH RG-102362 | 4 THQ RG-120499 | 5 THQ RG-120500 | 6 ECD 20E | 7 ECD PonA |
|---|---|---|---|---|---|---|---|---|
| Mutant | | | | | | | | |
| V107I/Y127E/A110P | EC50(μM) | 0.30 | 0.34 | 0.10 | ~20 | 3.71 | >33 | >33 |
| V107I/Y127E/A110P | Rel Max FI | 1.00 | 0.96 | 0.63 | 0.08 | 0.16 | 0.00 | 0.01 |
| V128F/A110P | EC50(μM) | ~8 | ~5 | | 0.45 | 0.28 | >33 | >33 |
| V128F/A110P | Rel Max FI | 1.00 | 0.08 | | 0.51 | 0.68 | 0.00 | 0.00 |

As seen in Table 6, both non-ecdysteroid, diacylhyrazine and tetrahydroquinoline activities were increased when the CfEcR ligand binding domain was mutated at amino acid residues 107, 110 and 127 and 107 and 127, indicating that these residues are important residues in the ligand binding pocket of CfEcR.

Example 7

Table 7 describes the effect of the diacylhydrazine GS™-E ligand versus the DMSO control at various concentrations on the maximum fold induction of various CfEcR mutants.

TABLE 7

Effect of GS ™-E ligand v. DMSO control on the maximum fold induction of CfEcR mutants.

| Mutant | GS ™-E ligand max FI (relative to DMSO) | Concentration (mM) at max FI |
|---|---|---|
| A110E | 4926 | 10.00 |
| A110N | 1678 | 10.00 |
| A110W | 5207 | 10.00 |
| F109W | 3063 | 10.00 |
| F109P | 1 | 10.00 |
| F109L | 20 | 33.30 |
| F109M | 1475 | 3.3 |
| F109N | 1506 | 33.3 |
| F48Y | 1355 | 33.3 |
| F48W | 1638 | 33.3 |
| F48L | 2599 | 33.3 |
| I51N | 1 | 33.30 |
| I51L | 2478 | 33.30 |
| L132M | 1517 | 10.00 |
| L132N | 785 | 33.30 |
| L132V | 2128 | 10.00 |
| L234M | 4578 | 33.30 |
| L234I | 2650 | 10 |
| M125P | 1 | 33.3 |
| M125R | 2407 | 33.3 |
| M125C | 9 | 33.3 |
| M54W | 1678 | 10 |
| M54T | 4460 | 10.00 |

TABLE 7-continued

Effect of GS ™-E ligand v. DMSO control on the maximum fold induction of CfEcR mutants.

| Mutant | GS ™-E ligand max FI (relative to DMSO) | Concentration (mM) at max FI |
|---|---|---|
| M92L | 1203 | 33.30 |
| M92E | 141 | 33.30 |
| R95H | 3413 | 33.30 |
| R95M | 1691 | 33.30 |

TABLE 7-continued

Effect of GS ™-E ligand v. DMSO control on the maximum fold induction of CfEcR mutants.

| Mutant | GS ™-E ligand max FI (relative to DMSO) | Concentration (mM) at max FI |
|---|---|---|
| R95W | 1820 | 33.30 |
| T52L | 1128 | 33.3 |
| T52E | 1537 | 33.3 |
| V96L | 4378 | 10 |
| V96W | 615 | 33.3 |
| V96S | 1828 | 33.3 |
| W238P | 4812 | 10 |
| W238E | 1018 | 33.3 |
| W238Y | 11 | 33.3 |
| Y120W | 1889 | 33.3 |
| Y120M | 1708 | 33.3 |
| N119F/V96T | 1738 | 33.3 |
| V107I/Y127E | 3146 | 10 |
| V107I/Y127E/A110P | 2212 | 10 |
| M125E | 1196 | 33.3 |
| M125L | 2250 | 33.3 |
| T52P | 301 | 33.3 |
| V96E | 2963 | 33.30 |
| A110P | 2289 | 3.30 |
| V128F/A110P | 2960 | 33.30 |
| V128F | 550 | 33.30 |

Example 8

This Example describes the identification of additional CfEcR ligand binding domain substitution mutants that exhibit decreased activity in response to diacylhydrazine ligands. In an effort to identify substitution mutations in the CfEcR that decrease diacylhydrazine ligand activity, Applicants mutated amino acid residues predicted to be critical in diacylhydrazine binding and created GAL4/mutantCfEcR-DEF cDNA gene expression cassettes as described in Example 1 using PCR-mediated site-directed mutagenesis kit. The mutated and the WT cDNAs corresponding to the various switch constructs outlined above in Example 1.1 and 1.2 were made and tested in GAL4-driven luciferase reporter assays as described in Example 2. The effect of an amino acid substitution at amino acid residue 48, 51, 52, 54, 92, 95, 96, 109, 120, 125, 219, 223, 234 or 238 of SEQ ID NO: 1 on the activity of the mutated CfEcR-DEF receptor is presented in Tables 8a and 8b.

TABLE 8a

CfEcR mutants that show decreased diacylhydrazine activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| M92L | EC50 (µM) | ~8 | 9.9 | ~20 | >33 | >33 | >33 | >33 |
| M92L | Rel Max FI | 1 | 0.41 | 0.05 | 0 | 0 | 0 | 0 |
| M92E | EC50 (µM) | ~8 | ~20 | >33 | >33 | >33 | >33 | >33 |
| M92E | Rel Max FI | 1 | 0.08 | 0.04 | 0 | 0 | 0 | 0.01 |
| R95W | EC50 (µM) | ~7 | ~10 | ~8 | >33 | >33 | >33 | >33 |
| R95W | Rel Max FI | 1 | 0.37 | 0.25 | 0 | 0 | 0 | 0 |
| T52E | EC50 (µM) | ~7 | ~7 | 7.16 | >33 | >33 | >33 | >33 |
| T52E | Rel Max FI | 1 | 0.57 | 0.34 | 0 | 0 | 0 | 0 |
| W238E | EC50 (µM) | ~6 | ~8 | 3.45 | >33 | >33 | >33 | >33 |
| W238E | Rel Max FI | 1 | 0.71 | 0.45 | 0 | 0 | 0 | 0 |
| Y120M | EC50 (µM) | ~4 | ~10 | ~10 | >33 | >33 | >33 | >33 |
| Y120M | Rel Max FI | 1 | 0.3 | 0.13 | 0 | 0 | 0 | 0.04 |
| I51L | EC50 (µM) | 3.2 | 2.28 | 3.35 | >33 | >33 | >33 | ~8 |
| I51L | Rel Max FI | 1 | 0.88 | 0.53 | 0 | 0 | 0 | 0.66 |
| V96W | EC50 (µM) | ~1 | 3.61 | 3.26 | >33 | >33 | >33 | ~3.3 |
| V96W | Rel Max FI | 1 | 0.75 | 0.38 | 0 | 0.01 | 0 | 0.83 |
| Y120W | EC50 (µM) | 4.21 | 9.76 | 4.96 | >33 | >33 | >33 | ~10 |
| Y120W | Rel Max FI | 1 | 0.89 | 0.67 | 0.02 | 0.01 | 0 | 0.69 |
| W238Y | EC50 (µM) | ~13 | >33 | >33 | >33 | >33 | >33 | >33 |
| W238Y | Rel Max FI | 1 | 0.3 | 0.06 | 0.13 | 0.1 | 0.18 | 0.07 |

TABLE 8a-continued

CfEcR mutants that show decreased diacylhydrazine activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| F109N | EC50 (µM) | 2.7 | 3.95 | 1.85 | >33 | >33 | >33 | >33 |
| F109N | Rel Max FI | 1 | 0.85 | 0.4 | 0 | 0 | 0 | 0 |
| L234M | EC50 (µM) | 1.43 | 1.79 | 2.04 | >33 | >33 | >33 | >33 |
| L234M | Rel Max FI | 1 | 0.77 | 0.43 | 0 | 0 | 0 | 0.02 |
| M125E | EC50 (µM) | ~2 | 0.98 | 0.83 | >33 | >33 | >33 | >33 |
| M125E | Rel Max FI | 1 | 0.53 | 0.4 | 0 | 0 | 0 | 0 |
| V96E | EC50 (µM) | ~2 | 1.62 | 1.86 | >33 | >33 | >33 | >33 |
| V96E | Rel Max FI | 1 | 0.81 | 0.48 | 0 | 0 | 0 | 0.02 |
| F48N | EC50 (µM) | 0.75 | 1.73 | 1.68 | >33 | >33 | >33 | ~20 |
| F48N | Rel Max FI | 1 | 0.88 | 0.66 | 0 | 0 | 0 | 0.17 |
| L234I | EC50 (µM) | 0.77 | 0.94 | 2.46 | >33 | >33 | >33 | ~7 |
| L234I | Rel Max FI | 1 | 0.73 | 0.44 | 0 | 0.01 | 0 | 0.56 |
| M54W | EC50 (µM) | 1.17 | 1.63 | 1.24 | >33 | >33 | >33 | ~10 |
| M54W | Rel Max FI | 1 | 0.75 | 0.44 | 0.01 | 0.01 | 0 | 0.46 |
| V96L | EC50 (µM) | ~1 | 1.68 | 2.67 | >33 | >33 | >33 | 7.49 |
| V96L | Rel Max FI | 1 | 0.62 | 0.58 | 0 | 0 | 0 | 0.49 |

TABLE 8b

CfEcR mutants that show decreased diacylhydrazine activity

| Mutant | | RG-102240 | RG-115840 | RG-115853 | RG-115855 | RG-115859 | RG-115898 |
|---|---|---|---|---|---|---|---|
| I51M | EC50 (µM) | 3.94 | 4.13 | 2.94 | 1.33 | 2 | >33 |
| I51M | Rel Max FI | 1 | 0.27 | 0.46 | 0.84 | 1.07 | 0.02 |
| L234R | EC50 (µM) | 17.1 | 20 | >33 | >33 | 20 | >33 |
| L234R | Rel Max FI | 1 | 2.24 | 0.2 | 0.21 | 3.8 | 0.58 |
| L234W | EC50 (µM) | 11.48 | >33 | >33 | 6 | 5 | >33 |
| L234W | Rel Max FI | 1 | 0.06 | 0.07 | 0.44 | 0.42 | 0.02 |
| M219A | EC50 (µM) | 2.9 | 2.87 | 3.65 | 1.44 | 3.18 | 1 |
| M219A | Rel Max FI | 1 | 0.6 | 0.79 | 0.86 | 0.85 | 0.05 |
| L223K | EC50 (µM) | 3.93 | 1 | 2.5 | 1.23 | 0.38 | 0.28 |
| L223K | Rel Max FI | 1 | 0.93 | 0.54 | 0.87 | 0.9 | 0.18 |
| M125V | EC50 (µM) | 1.64 | 3.79 | 1.72 | 2 | 1 | >33 |
| M125V | Rel Max FI | 1 | 0.47 | 0.5 | 0.74 | 0.87 | 0.01 |
| M219K | EC50 (µM) | 2.9 | >33 | 3.31 | 1.93 | 5 | >33 |
| M219K | Rel Max FI | 1 | 0.01 | 0.22 | 0.34 | 0.66 | 0 |
| M219W | EC50 (µM) | 3.35 | 2.33 | ~20 | 2 | 4 | >33 |
| M219W | Rel Max FI | 1 | 0.39 | 0.12 | 0.34 | 0.46 | 0 |

TABLE 8b-continued

CfEcR mutants that show decreased diacylhydrazine activity

| Mutant | | RG-102240 | RG-115840 | RG-115853 | RG-115855 | RG-115859 | RG-115898 |
|---|---|---|---|---|---|---|---|
| M219Y | EC50 (µM) | 0.82 | 1 | ~20 | 2 | 2 | >33 |
| | Rel Max FI | 1 | 0.68 | 0.05 | 0.32 | 0.51 | 0.01 |
| T52M | EC50 (µM) | 6.74 | 5 | 1.36 | 10 | 3.56 | >33 |
| | Rel Max FI | 1 | 0.15 | 0.32 | 0.66 | 1.08 | 0.01 |
| T52R | EC50 (µM) | 6.69 | >33 | 5 | 3.31 | 6.14 | >33 |
| | Rel Max FI | 1 | 0.02 | 0.06 | 0.1 | 0.41 | 0 |
| W238L | EC50 (µM) | 11.13 | 2 | >33 | 2 | 5 | >33 |
| | Rel Max FI | 1 | 0.41 | 0.02 | 0.09 | 1.08 | 0 |
| W238M | EC50 (µM) | 10.47 | 2 | >33 | 2 | 1.85 | >33 |
| | Rel Max FI | 1 | 0.41 | 0.05 | 0.72 | 16.07 | 0.03 |
| F48K | EC50 (µM) | 11.09 | 3.76 | 4.42 | 2.45 | >33 | >33 |
| | Rel Max FI | 1 | 0.18 | 0.71 | 4.78 | 0.02 | 0.08 |
| T52G | EC50 (µM) | 3.52 | 3.61 | 3.35 | 2 | 6.49 | >33 |
| | Rel Max FI | 1 | 0.23 | 0.28 | 0.31 | 0.44 | 0.01 |
| T52Q | EC50 (µM) | 2.95 | 2 | >33 | 0.56 | 1.11 | 20 |
| | Rel Max FI | 1 | 0.34 | 0.04 | 0.39 | 1.02 | 0.08 |
| L223R | EC50 (µM) | 8.69 | 2 | 2 | 1.2 | 5.19 | >33 |
| | Rel Max FI | 1 | 0.25 | 0.09 | 1.35 | 0.61 | 0.01 |

As seen in Tables 8a and 8b, the activity of diacylhydrazines was decreased significantly when the CfEcR ligand binding domain was mutated at amino acid residues 48, 51, 52, 54, 92, 95, 96, 109, 120, 125, 219, 223, 234 or 238 of SEQ ID NO: 1, indicating that these residues are important residues in the ligand binding pocket of CfEcR.

Example 9

This Example describes the identification of additional CfEcR ligand binding domain substitution mutants that are generally tetrahydroquinoline responsive that exhibit increased activity in response to tetrahydroquinoline ligands. In an effort to identify substitution mutations in the CfEcR that increase tetrahydroquinoline ligand activity, Applicants mutated specific amino acid residues and created GAL4/mutantCfEcR-DEF cDNA gene expression cassettes as described in Example 1 using PCR-mediated site-directed mutagenesis kit. The mutated and the WT cDNAs corresponding to the various switch constructs outlined above in Example 1.1 and 1.2 were made and tested in GAL4-driven luciferase reporter assays as described in Example 2. The effect of an amino acid substitution at amino acid residue 110 or 128 of SEQ ID NO: 1 or the double amino acid substitution at amino acid residues 110 and 128 of SEQ ID NO: 1 on the activity of the mutated CfEcR-DEF receptor is presented in Table 9.

TABLE 9

CfEcR mutants that show increased tetrahydroquinoline activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| A110W | EC50 (µM) | 1.37 | 1.06 | 2.99 | ~10 | ~5 | >33 | >33 |
| A110W | Rel Max FI | 1 | 0.8 | 0.55 | 0.06 | 0.07 | 0 | 0.01 |
| V128F | EC50 (µM) | >33 | ~8.3, 5.4 | >33 | >33 | ~10 | ~10 | >33 |
| V128F | Rel Max FI | 0 | 0.04 | 2.34 | 0.05 | 1 | 0.02 | 0.03 |

TABLE 9-continued

CfEcR mutants that show increased tetrahydroquinoline activity

| Mutant | | DAH RG-102240 | DAH RG-101691 | DAH RG-102362 | THQ RG-120499 | THQ RG-120500 | ECD 20E | ECD PonA |
|---|---|---|---|---|---|---|---|---|
| V128F/A110P | EC50 (μM) | ~8 | ~5 | | 0.45 | 0.28 | >33 | >33 |
| V128F/A110P | Rel Max FI | 1 | 0.08 | | 0.51 | 0.68 | 0 | 0 |

As seen in Table 9, the activity of tetrahydroquinolines was increased significantly when the CfEcR ligand binding domain was mutated at amino acid residues 110 or 128 of SEQ ID NO: 1 or doubled mutated at amino acid residues 110 and 128 of SEQ ID NO: 1, indicating that these residues are important residues in the ligand binding pocket of CfEcR.

Example 10

This Example describes the identification of additional CfEcR ligand binding domain substitution mutants that are differentially responsive to diacylhydrazine ligands. These mutants exhibit a general decrease in diacylhydrazine activity; however they are selectively responsive to a specific diacylhydrazine ligand. In an effort to identify substitution mutations in the CfEcR, Applicants mutated specific amino acid residues and created GAL4/mutantCfEcR-DEF cDNA gene expression cassettes as described in Example 1 using PCR-mediated site-directed mutagenesis kit. The mutated and the WT cDNAs corresponding to the various switch constructs outlined above in Example 1.1 and 1.2 were made and tested in GAL4-driven luciferase reporter assays as described in Example 2. The effect of an amino acid substitution at amino acid residue 52, 95, 109, 125 or 132 of SEQ ID NO: 1 on the activity of the mutated CfEcR DEF receptor is presented in Tables 10a and 10b.

TABLE 10a

| CfEcR mutants that show decreased diacylhydrazine activity and increased activity in response to diacylhydrazine RG-115855 | | | | | | | | | |
|---|---|---|---|---|---|---|---|---|---|
| Mutant | | RG-102240 | RG-101691 | RG-102362 | RG-115855 | RG-120499 | RG 120500 | 20E | PonA |
| F109L | EC50 (μM) | ~2 | 2.34 | ~2.5 | 1.73 | >33 | >33 | >33 | >33 |
| F109L | Rel Max FI | 1 | 0.68 | 0.17 | 1.01 | 0.03 | 0.02 | 0.09 | 0.03 |
| L132M | EC50 (μM) | ~12 | ~20 | >33 | 0.39 | >33 | >33 | >33 | >33 |
| L132M | Rel Max FI | 1 | 0.08 | 0.01 | 0.90 | 0 | 0 | 0.01 | 0.01 |
| R95H | EC50 (μM) | 1.58 | 3.9 | 3.49 | 0.78 | >33 | >33 | >33 | >33 |
| R95H | Rel Max FI | 1 | 0.96 | 0.62 | 0.68 | 0 | 0 | 0 | 0.03 |
| R95M | EC50 (μM) | 2.76 | 3.3 | 4.28 | 3.74 | >33 | >33 | >33 | >33 |
| R95M | Rel Max FI | 1 | 0.57 | 0.27 | 0.33 | 0 | 0.01 | 0 | 0 |
| M125L | EC50 (μM) | ~10 | >33 | >33 | 0.16 | >33 | >33 | >33 | >33 |
| M125L | Rel Max FI | 1 | 0 | 0.01 | 2.15 | 0 | 0 | 0 | 0 |
| T52P | EC50 (μM) | ~10 | >33 | ~6 | 3.87 | >33 | >33 | >33 | >33 |
| T52P | Rel Max FI | 1 | 0.02 | 0.11 | 1.93 | 0.03 | 0.03 | 0.02 | 0.03 |
| M125W | EC50 (μM) | 3.49 | 4.94 | 3.5 | 0.03 | >33 | >33 | >33 | >33 |
| M125W | Rel Max FI | 1 | 0.74 | 0.44 | 1.24 | 0 | 0 | 0 | 0 |
| M125R | EC50 (μM) | 3.7 | ~10 | 10.38 | 0.02 | >33 | >33 | >33 | ~8 |
| M125R | Rel Max FI | 0 | 0.01 | 0 | 1.39 | 0 | | 0.01 | 0 |
| M125C | EC50 (μM) | ~8, >33 | 33 | 33 | 0.58 | 33 | 33 | 33 | 33 |
| M125C | Rel Max FI | 1 | 0.62 | 0.15 | 876.58 | 0.27 | 0.14 | 0.22 | 0.28 |
| M125P | EC50 (μM) | >33 | >33 | >33 | 0.45 | >33 | >33 | >33 | >33 |
| M125P | Rel Max FI | 1 | 5.25 | 0.78 | 380.86 | 0.65 | 1.3 | 1.29 | 0.7 |

TABLE 10b

CfEcR mutants that show decreased RG-102240 diacylhydrazine activity and increased activity in response to other diacylhydrazines

| Mutant | | RG-102240 | RG-115840 | RG-115853 | RG-115855 | RG-115859 | RG-115898 |
|---|---|---|---|---|---|---|---|
| M125S | EC50 (μM) | 12.33 | 1.4 | 0.98 | 0.11 | 7.26 | 0.33 |
| | Rel Max FI | 1 | 22.73 | 15.97 | 25.22 | 6.39 | 16.98 |
| T52W | EC50 (μM) | 18.33 | 4.07 | 2 | 0.96 | 7 | 0.18 |
| | Rel Max FI | 1 | 30.59 | 89.32 | 49.21 | 2.81 | 4.24 |

As seen in Tables 10a and 10b, the activity of diacylhydrazines was differentially affected when the CfEcR ligand binding domain was mutated at amino acid residues 52, 95, 109, 125 or 132 of SEQ ID NO: 1, indicating that these residues are important residues in the ligand binding pocket of CfEcR.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A recombinant gene expression modulation system comprising a recombinant gene expression cassette that is capable of being expressed in a host cell, the gene expression cassette comprising a polynucleotide that encodes a first polypeptide comprising:
   (a) a transactivation domain;
   (b) a DNA-binding domain that recognizes a response element associated with a gene whose expression is to be modulated; and
   (c) a nuclear receptor ligand binding domain that is capable of binding a diacylhydrazine and comprises either an amino acid residue substitution mutation of SEQ ID NO: 1 at
      (i) at least one of amino residues 54, 119, 127, 128 and 132,
      (ii) amino acid residues 96 and 119,
      (iii) amino acid residues 110 and 128,
      (iv) amino acid residues 52 and 110,
      (v) amino acid residues 132 and 125
      (vi) amino acid residues 107, 110 and 127,
      (vii) amino acid residues 52, 107 and 127, or
      (viii) amino acid residues 107, 127 and an insertion at 259, or
   at least one of the mutations F48Y, F48W, F48L, F48N, F48R, F48K, I51M, I51N, 151L, T52M, T52E, T52P, T52R, T52W, T52G, T52Q, M92L, M92E, R95H, R95M, R95W, V96L, V96W, V96S, V96E, V96T, V107I, F109W, F109P, F109L, F109M, F109N, A110E, A110N, A110P, A110W, Y120W, Y120M, M125P, M125R, M125E, M125L, M125C, M125W, M125G, M125I, M125N, M125S, M125V, Y127E, M219K, M219W, M219Y, M219A, L223K, L223R, L223Y, L234M, L234I, L234R, L234W, W238P, W238E, W238Y, W238M and W238L.

2. The recombinant gene expression modulation system according to claim 1, further comprising a second polynucleotide that encodes a second polypeptide, said second polypeptide comprising a second nuclear receptor ligand binding domain which is a vertebrate retinoid X receptor ligand binding domain, an invertebrate retinoid X receptor ligand binding domain, an ultraspiracle protein ligand binding domain, or a chimeric ligand binding domain comprising a first polypeptide fragment and a second polypeptide fragment, wherein said first polypeptide fragment is different from said second polypeptide fragment and each of the said first and said second fragments is a vertebrate retinoid X receptor ligand binding domain, an invertebrate retinoid X receptor ligand binding domain, or an ultraspiracle protein ligand binding domain.

3. A recombinant gene expression modulation system comprising:
   (a) a first recombinant gene expression cassette that is capable of being expressed in a host cell comprising a polynucleotide that encodes a first polypeptide comprising:
      (i) a DNA-binding domain that recognizes a response element associated with a gene whose expression is to be modulated; and
      (ii) a first nuclear receptor ligand binding domain; and
   (b) a second recombinant gene expression cassette that is capable of being expressed in the host cell comprising a polynucleotide that encodes a second polypeptide comprising:
      (i) a transactivation domain; and
      (ii) a second nuclear receptor ligand binding domain,
   wherein one of said first and said second nuclear receptor ligand binding domains is capable of binding a diacyl hydrazine, and comprises either an amino acid residue substitution mutation of SEQ ID NO: 1 at
   (1) at least one of amino residues 54, 119, 127, 128 and 132,
   (2) amino acid residues 96 and 119,
   (3) amino acid residues 110 and 128,
   (4) amino acid residues 52 and 110,
   (5) amino acid residues 132 and 125
   (6) amino acid residues 107, 110 and 127,
   (7) amino acid residues 52, 107 and 127, or
   (8) amino acid residues 107, 127 and an insertion at 259, or
   at least one of the mutations F48Y, F48W, F48L, F48N, F48R, F48K, I51M, I51N, 151L, T52M, T52E, T52P, T52R, T52W, T52G, T52Q, M92L, M92E, R95H, R95M, R95W, V96L, V96W, V96S, V96E, V96T, V107I, F109W, F109P, F109L, F109M, F109N, A110L, A110N, A110P, A110W, Y120W, Y120M, M125P, M125R, M125E, M125L, M125C, M12SW, M125G, M125I, M125N, M125S, M125V, Y127E, M219K, M219W, M219Y, M219A, L223K, L223R, L223Y, L234M, L234I, L234R, L234W, W238P, W238E, W238Y, W238M and W238L.

4. The recombinant gene expression modulation system according to claim 3, wherein said nuclear receptor ligand binding domain that comprises at least one amino acid residue substitution mutation is an ecdysone receptor ligand binding domain, a ubiquitous receptor ligand binding domain, an orphan receptor 1 ligand binding domain, a NER-1 ligand binding domain, a steroid hormone nuclear receptor 1 ligand binding domain, a retinoid X receptor interacting protein-15 ligand binding domain, a liver X receptor β ligand binding domain, a steroid hormone receptor like protein ligand binding domain, a liver X receptor ligand binding domain, a liver X receptor α ligand binding domain, a farnesoid X receptor ligand binding domain, a receptor interacting protein 14 ligand binding domain, or a farnesol receptor ligand binding domain.

5. The recombinant gene expression modulation system according to claim 3, wherein the substitution mutation is M54W, M54T, N119F, L132M, L132N, L132V, L132E, T52V/A110P, V107I/Y127E/T52V, V107I/Y127E/G259 or V107I/Y127E/A110P.

6. The recombinant gene expression modulation system according to claim 3, wherein the DNA-binding domain is an ecdysone receptor DNA-binding domain, a GAL4 DNA-binding domain, or a LexA DNA-binding domain.

7. The recombinant gene expression modulation system according to claim 3, wherein the transactivation domain is an ecdysone receptor transactivation domain, a VP16 transactivation domain, a B42 acidic activator transactivation domain, or a p65 transactivation domain.

8. An isolated polynucleotide, wherein said isolated polynucleotide encodes a nuclear receptor ligand binding domain that is capable of binding a diacylhydrazine, and comprises either an amino acid residue substitution mutation of SEQ ID NO: 1 at
   (a) at least one of amino residues 54, 119, 127, 128 and 132,
   (b) amino acid residues 96 and 119,
   (c) amino acid residues 110 and 128,
   (d) amino acid residues 52 and 110,
   (e) amino acid residues 132 and 125
   (f) amino acid residues 107, 110 and 127,
   (g) amino acid residues 52, 107 and 127, or
   (h) amino acid residues 107, 127 and an insertion at 259, or
   at least one of the mutations F48Y, F48W, F48L, F48N, F48R, F48K, 151M, 151N, I51L, T52M, T52E, T52P, T52R, T52W, T52G, T52G, M92L, M92E, R95H, R95M, R95W, V96L, V96W, V96S, V96E, V96T, V107I, F109W, F109P, F109L, F109M, F109N, A110E, A110N, A110P, A110W, Y120W, Y120M, M125P, M125R, M125E, M125L, M125C, M125W, M125G, M125I, M125N, M125S, M125V, Y127E, V128F, M219K, M219W, M219Y, M219A, L223K, L223R, L223Y, L234M, L234I, L234R, L234W, W238P, W238E, W238Y, W238M and W238L.

9. The isolated polynucleotide according to claim 8, wherein the substitution mutation of SEQ ID NO: 1 is M54W, M54T, N119F, L132M, L132N, L132V, L132E, N119F/V96T, V128F/A110P, T52V/A110P, V107I/Y127E/T52V, V107I/Y127E/G259 or V107I/Y127E/A110P.

10. An expression vector comprising the isolated polynucleotide of claim 8 operatively linked to a transcription regulatory element.

11. An isolated host cell comprising the expression vector of claim 10, wherein the transcription regulatory element is operative in the host cell.

12. An isolated host cell comprising the recombinant gene expression modulation system according to claim 3.

13. The isolated polynucleotide according to claim 8, wherein said isolated polynucleotide further encodes at least one of an ecdysone receptor DNA-binding domain, a GAL4 DNA-binding domain, a LexA DNA-binding domain, an ecdysone receptor transactivation domain, a VP16 transactivation domain, a B42 acidic activator transactivation domain, or a p65 transactivation domain.

14. An expression vector comprising the isolated polynucleotide according to claim 13 operatively linked to a transcription regulatory element.

15. An isolated host cell comprising the expression vector of claim 14, wherein the transcription regulatory element is operative in the host cell.

16. A recombinant gene expression cassette comprising an isolated polynucleotide that encodes
(a) a polypeptide comprising a transactivation domain, a DNA-binding domain, and a nuclear receptor ligand binding domain,
(b) a polypeptide comprising a DNA-binding domain and a nuclear receptor ligand binding domain, or
(c) a polypeptide comprising a transactivation domain and a nuclear receptor ligand binding domain,
wherein said nuclear receptor ligand binding domain is capable of binding a diacylhydrazine, and comprises either an amino acid residue substitution mutation of SEQ ID NO: 1 at
(a) at least one of amino residues 54, 119, 127, 128 and 132,
(b) amino acid residues 96 and 119,
(c) amino acid residues 110 and 128,
(d) amino acid residues 52 and 110,
(e) amino acid residues 132 and 125
(f) amino acid residues 107, 110 and 127,
(g) amino acid residues 52, 107 and 127, or
(h) amino acid residues 107, 127 and an insertion at 259, or
at least one of the mutations F48Y, F48W, F48L, F48N, F48R, F48K, I51M, I51N, I51L, T52M, T52E, T52P, T52R, T52W, T52G, T52O, M92L, M92E, R95H, R95M, R95W, V96L, V96W, V96S, V96E, V96T, V107I, F109W, F109P, F109L, F109M, F109N, A110E, A110N, A110P, A110W, Y120W, Y120M, M125P, M125R, M125E, M125L, M125C, M125W, M125G, M125I, M125N, M125S, M125V, Y127E, V128F, M219K, M219W, M219Y, M219A, L223K, L223R, L223Y, L234M, L234I, L234R, L234W, W238P, W238E, W238Y, W238M and W238L.

17. The recombinant gene cassette according to claim 16, wherein said substitution mutation is M54W, M54T, L132M, L132N, L132V, L132E, N119F, N119F/V96T, V128F/A110P, T52V/A110P, V107I/Y127E/T52V, V107I/Y127E/G259, or V107I/Y127E/A110P.

18. The recombinant gene cassette according to claim 16, wherein said at least one amino acid residue substitution mutation is V107I/Y127E and the insertion mutation is G259.

19. The recombinant gene cassette according to claim 16, wherein said at least one amino acid residue substitution mutation is V107I/Y127E/A110P.

20. The recombinant gene cassette according to claim 16, wherein said at least one amino acid residue substitution mutation is V107I/Y127E/T52V.

21. The recombinant gene expression modulation system according to claim 3, wherein the other of said first and second nuclear receptor ligand binding domains is a vertebrate retinoid X receptor ligand binding domain, an invertebrate retinoid X receptor ligand binding domain, an ultraspiracle protein ligand binding domain, or a chimeric ligand binding domain comprising a first polypeptide fragment and a second polypeptide fragment, wherein said first polypeptide fragment is different from said second polypeptide fragment and each of said first and said second fragments is independently selected from a vertebrate retinoid X receptor ligand binding domain, an invertebrate retinoid X receptor ligand binding domain, or an ultraspiracle protein ligand binding domain.

22. The recombinant gene expression modulation system comprising the recombinant gene cassette according to claim 1, wherein said substitution mutation of SEQ ID NO: 1 is M54W, M54T, V128F, L132M, L132N, L132V, L132E, N119F/V96T, V128F/A110P, T52V/A110P, V107I/Y127E/T52V, V107I/Y127E/G259, or V107I/Y127E/A110P.

23. The recombinant gene expression modulation system according to claim 1, wherein said nuclear receptor ligand binding domain is an ecdysone receptor ligand binding domain, a ubiquitous receptor ligand binding domain, an orphan receptor 1 ligand binding domain, a NER-1 ligand binding domain, a steroid hormone nuclear receptor 1 ligand binding domain, a retinoid X receptor interacting protein-15 ligand binding domain, a liver X receptor β ligand binding domain, a steroid hormone receptor like protein ligand binding domain, a liver X receptor ligand binding domain, a liver X receptor α ligand binding domain, a farnesoid X receptor ligand binding domain, a receptor interacting protein 14 ligand binding domain, or a farnesol receptor ligand binding domain.

24. An isolated host cell comprising the recombinant gene expression modulation system according to claim 1.

25. The recombinant gene expression modulation system of claim 23, wherein said nuclear receptor ligand binding domain is an ecdysone receptor ligand binding domain.

26. The recombinant gene expression modulation system of claim 3, wherein said nuclear receptor ligand binding domain is an ecdysone receptor ligand binding domain.

27. The isolated host cell of claim 1, wherein said cell is a mammalian cell.

28. The isolated host cell of claim 27, wherein said cell is a human cell.

29. The isolated host cell of claim 12, wherein said cell is a mammalian cell.

30. The isolated host cell of claim 29, wherein said cell is a human cell.

31. The isolated host cell of claim 15, wherein said cell is a mammalian cell.

32. The isolated host cell of claim 31, wherein said cell is a human cell.

* * * * *

UNITED STATES PATENT AND TRADEMARK OFFICE
CERTIFICATE OF CORRECTION

PATENT NO. : 7,935,510 B2
APPLICATION NO. : 11/118855
DATED : May 3, 2011
INVENTOR(S) : Palli et al.

It is certified that error appears in the above-identified patent and that said Letters Patent is hereby corrected as shown below:

In the Claims

Column 173
Line 34, claim 1, replace "L2341" with --L234I--.

Column 174
Line 13, claim 3, replace "151L" with --I51L--.

Column 174
Line 16, claim 3, replace "A110L" with --A110E--.

Column 174
Line 18, claim 3, replace "M12SW" with --M125W--.

Column 174
Line 33, claim 4, replace "receptor a ligand" with --receptor α ligand--.

Column 174
Lines 38-39, claim 5, replace "L132E, T52V/A110P," with --L132E, N119F/V96T, V128F/A110P, T52V/A110P,--.

Column 174
Lines 39-40, claim 5, replace "V107I/Y127E/G259 or V107I/Y127E/A110P" with --or V107I/Y127E/A110P, or the substitution mutation V107I/Y127E and the insertion mutation G259--.

Column 174
Line 63, claim 8, replace "151M, 151N," with --I51M, I51N,--.

Signed and Sealed this
Nineteenth Day of November, 2013

Teresa Stanek Rea
*Deputy Director of the United States Patent and Trademark Office*

Column 174
Line 64, claim 8, replace "T52G, T52G," with --T52G, T52Q--.

Column 175
Line 4, claim 8, replace "L2341," with --L234I,--.

Column 175
Line 54, claim 16, replace "I51M, I51N," with --I51M, I51N,--.

Column 175
Line 56, claim 16, replace "T52O," with --T52Q,--.

Column 175
Line 57, claim 16, replace "V107I," with --V107I,--.

Column 176
Lines 1-2, claim 17, replace "V107I/Y127E/G259, or V107I/Y127E/A110P" with --or V107I/Y127E/A110P, or the substitution mutation V107I/Y127E and the insertion mutation G259--.

Column 176
Line 29, claim 22, replace "M54T, V128F," with --M54T, N119F, V128F,--.

Column 176
Line 31, claim 22, replace "V107I/Y127E/G259, or V107I/Y127E/A110P" with --or V107I/Y127E/A110P, or the substitution mutation V107I/Y127E and the insertion mutation G259--.

Column 176
Line 56, claim 27, replace "host cell of claim 1," with --host cell of claim 11,--.

SEQUENCE LISTING

```
<160> NUMBER OF SEQ ID NOS: 176

<210> SEQ ID NO 1
<211> LENGTH: 259
<212> TYPE: PRT
<213> ORGANISM: Choristoneura fumiferana

<400> SEQUENCE: 1

Leu Thr Ala Asn Gln Gln Phe Leu Ile Ala Arg Leu Ile Trp Tyr Gln
1               5                   10                  15

Asp Gly Tyr Glu Gln Pro Ser Asp Glu Asp Leu Lys Arg Ile Thr Gln
            20                  25                  30

Thr Trp Gln Gln Ala Asp Asp Glu Asn Glu Glu Ser Asp Thr Pro Phe
        35                  40                  45

Arg Gln Ile Thr Glu Met Thr Ile Leu Thr Val Gln Leu Ile Val Glu
    50                  55                  60

Phe Ala Lys Gly Leu Pro Gly Phe Ala Lys Ile Ser Gln Pro Asp Gln
65                  70                  75                  80

Ile Thr Leu Leu Lys Ala Cys Ser Ser Glu Val Met Met Leu Arg Val
                85                  90                  95

Ala Arg Arg Tyr Asp Ala Ala Ser Asp Ser Val Leu Phe Ala Asn Asn
            100                 105                 110

Gln Ala Tyr Thr Arg Asp Asn Tyr Arg Lys Ala Gly Met Ala Tyr Val
        115                 120                 125

Ile Glu Asp Leu Leu His Phe Cys Arg Cys Met Tyr Ser Met Ala Leu
    130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
        195                 200                 205
```

Leu Arg Thr Leu Gly Met Gln Asn Ser Asn Met Cys Ile Ser Leu Lys
    210                 215                 220

Leu Lys Asn Arg Lys Leu Pro Pro Phe Leu Glu Glu Ile Trp Asp Val
225                 230                 235                 240

Ala Asp Met Ser His Thr Gln Pro Pro Ile Leu Glu Ser Pro Thr
                245                 250                 255

Asn Leu Gly

<210> SEQ ID NO 2
<211> LENGTH: 1022
<212> TYPE: DNA
<213> ORGANISM: Cytomegalovirus

<400> SEQUENCE: 2

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgcccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg ccccctattg acgtcaatga     420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg ggatttcca agtctccacc ccattgacgt      600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
ag                                                                   1022
```

<210> SEQ ID NO 3
<211> LENGTH: 720
<212> TYPE: DNA
<213> ORGANISM: Homo sapiens

<400> SEQUENCE: 3

```
gcccccgagg agatgcctgt ggacaggatc ctggaggcag agcttgctgt ggaacagaag      60
agtgaccagg gcgttgaggg tcctggggga accgggggta gcggcagcag cccaaatgac     120
cctgtgacta acatctgtca ggcagctgac aaacagctat tcacgcttgt tgagtgggcg     180
aagaggatcc cacactttc ctccttgcct ctggatgatc aggtcatatt gctgcgggca     240
ggctggaatg aactcctcat tgcctccttt tcacaccgat ccattgatgt tcgagatggc     300
atcctccttg ccacaggtct tcacgtgcac cgcaactcag cccattcagc aggagtagga     360
gccatctttg atcgggtgct gacagagcta gtgtccaaaa tgcgtgacat gaggatggac     420
aagacagagc ttggctgcct gagggcaatc attctgttta atccagatgc caagggcctc     480
tccaacccta gtgaggtgga ggtcctgcgg gagaaagtgt atgcatcact ggagacctac     540
```

```
tgcaaacaga agtaccctga gcagcaggga cggtttgcca agctgctgct acgtcttcct    600
gccctccggt ccattggcct aagtgtcta gagcatctgt ttttcttcaa gctcattggt    660
gacaccccca tcgacacctt cctcatggag atgcttgagg ctccccatca actggcctga    720
```

```
<210> SEQ ID NO 4
<211> LENGTH: 198
<212> TYPE: DNA
<213> ORGANISM: Choristoneura fumiferana

<400> SEQUENCE: 4
tgtctggtat gcggggacag agcctccgga taccactaca atgcgctcac gtgtgaaggg     60
tgtaaagggt tcttcagacg gagtgttacc aaaaatgcgg tttatatttg taaattcggt    120
cacgcttgcg aaatggacat gtacatgcga cggaaatgcc aggagtgccg cctgaagaag    180
tgcttagctg taggcatg                                                  198
```

```
<210> SEQ ID NO 5
<211> LENGTH: 66
<212> TYPE: PRT
<213> ORGANISM: Choristoneura fumiferana

<400> SEQUENCE: 5

Cys Leu Val Cys Gly Asp Arg Ala Ser Gly Tyr His Tyr Asn Ala Leu
1               5                   10                  15

Thr Cys Glu Gly Cys Lys Gly Phe Phe Arg Arg Ser Val Thr Lys Asn
            20                  25                  30

Ala Val Tyr Ile Cys Lys Phe Gly His Ala Cys Glu Met Asp Met Tyr
        35                  40                  45

Met Arg Arg Lys Cys Gln Glu Cys Arg Leu Lys Lys Cys Leu Ala Val
    50                  55                  60

Gly Met
65
```

```
<210> SEQ ID NO 6
<211> LENGTH: 441
<212> TYPE: DNA
<213> ORGANISM: Saccharomyces cerevisiae

<400> SEQUENCE: 6
atgaagctac tgtcttctat cgaacaagca tgcgatattt gccgacttaa aaagctcaag     60
tgctccaaag aaaaaccgaa gtgcgccaag tgtctgaaga caactggga gtgtcgctac    120 tctcccaaaa ccaaaaggtc tccgctgact agggcacatc tgacagaagt ggaatcaagg    180
ctagaaagac tggaacagct atttctactg attttcctc gagaagacct tgacatgatt    240
ttgaaaatgg attctttaca ggatataaaa gcattgttaa caggattatt tgtacaagat    300
aatgtgaata aagatgccgt cacagataga ttggcttcag tggagactga tatgcctcta    360
acattgagac agcatagaat aagtgcgaca tcatcatcgg aagagagtag taacaaaggt    420
caaagacagt tgactgtatc g                                              441
```

```
<210> SEQ ID NO 7
<211> LENGTH: 147
<212> TYPE: PRT
<213> ORGANISM: Saccharomyces cerevisiae

<400> SEQUENCE: 7

Met Lys Leu Leu Ser Ser Ile Glu Gln Ala Cys Asp Ile Cys Arg Leu
1               5                   10                  15
```

```
Lys Lys Leu Lys Cys Ser Lys Glu Lys Pro Lys Cys Ala Lys Cys Leu
             20                  25                  30

Lys Asn Asn Trp Glu Cys Arg Tyr Ser Pro Lys Thr Lys Arg Ser Pro
         35                  40                  45

Leu Thr Arg Ala His Leu Thr Glu Val Glu Ser Arg Leu Glu Arg Leu
 50                  55                  60

Glu Gln Leu Phe Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
             100                 105                 110

Ser Val Glu Thr Asp Met Pro Leu Thr Leu Arg Gln His Arg Ile Ser
             115                 120                 125

Ala Thr Ser Ser Ser Glu Glu Ser Ser Asn Lys Gly Gln Arg Gln Leu
 130                 135                 140

Thr Val Ser
145

<210> SEQ ID NO 8
<211> LENGTH: 606
<212> TYPE: DNA
<213> ORGANISM: Escherichia coli

<400> SEQUENCE: 8
atgaaagcgt taacggccag gcaacaagag gtgtttgatc tcatccgtga tcacatcagc      60
cagacaggta tgccgccgac gcgtgcggaa atcgcgcagc gtttgggggtt ccgttcccca    120 aacgcggctg aagaacatct gaaggcgctg gcacgcaaag gcgttattga aattgtttcc    180
ggcgcatcac gcgggattcg tctgttgcag gaagaggaag aagggttgcc gctggtaggt    240
cgtgtggctg ccggtgaacc acttctggcg caacagcata ttgaaggtca ttatcaggtc    300
gatccttcct tattcaagcc gaatgctgat ttcctgctgc gcgtcagcgg gatgtcgatg    360
aaagatatcg gcattatgga tggtgacttg ctggcagtgc ataaaactca ggatgtacgt    420
aacggtcagg tcgttgtcgc acgtattgat gacgaagtta ccgttaagcg cctgaaaaaa    480
cagggcaata aagtcgaact gttgccagaa aatagcgagt ttaaaccaat tgtcgtagat    540
cttcgtcagc agagcttcac cattgaaggg ctggcggttg gggttattcg caacggcgac    600
tggctg                                                               606

<210> SEQ ID NO 9
<211> LENGTH: 202
<212> TYPE: PRT
<213> ORGANISM: Escherichia coli

<400> SEQUENCE: 9

Met Lys Ala Leu Thr Ala Arg Gln Gln Glu Val Phe Asp Leu Ile Arg
 1               5                  10                  15

Asp His Ile Ser Gln Thr Gly Met Pro Pro Thr Arg Ala Glu Ile Ala
             20                  25                  30

Gln Arg Leu Gly Phe Arg Ser Pro Asn Ala Ala Glu Glu His Leu Lys
         35                  40                  45

Ala Leu Ala Arg Lys Gly Val Ile Glu Ile Val Ser Gly Ala Ser Arg
 50                  55                  60

Gly Ile Arg Leu Leu Gln Glu Glu Glu Glu Gly Leu Pro Leu Val Gly
 65                  70                  75                  80
```

```
Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200

<210> SEQ ID NO 10
<211> LENGTH: 420
<212> TYPE: DNA
<213> ORGANISM: Choristoneura fumiferana

<400> SEQUENCE: 10
atgagacgcc gctggtccaa caacgggggc ttccagacgc tgcgaatgct cgaggagagc      60
tcgtccgaag tgacgtcgtc ctcagctctg ggtctgccgg ccgcgatggt tatgtctccg     120
gagtcgctcg cctcgccaga gtacggcggg ctcgagctct ggggatacga cgatgggttg     180
tcatacaaca cggcgcagtc cttgctgggc aatacttgca cgatgcagca gcagcaacag     240
acgcagccgc tgccgtcgat gccgttgcct atgccgccga ccacgccgaa gtctgaaaac     300
gagtctattt cctcaggccg tgaggaactg tcgccagctt caagtataaa tgggtgcagt     360
acagatggcg aggcacgacg tcagaagaag ggccctgcgc cccgtcagca gaggaactg      420

<210> SEQ ID NO 11
<211> LENGTH: 140
<212> TYPE: PRT
<213> ORGANISM: Choristoneura fumiferana

<400> SEQUENCE: 11

Met Arg Arg Arg Trp Ser Asn Asn Gly Gly Phe Gln Thr Leu Arg Met
1               5                   10                  15

Leu Glu Glu Ser Ser Ser Glu Val Thr Ser Ser Ser Ala Leu Gly Leu
            20                  25                  30

Pro Ala Ala Met Val Met Ser Pro Glu Ser Leu Ala Ser Pro Glu Tyr
        35                  40                  45

Gly Gly Leu Glu Leu Trp Gly Tyr Asp Asp Gly Leu Ser Tyr Asn Thr
    50                  55                  60

Ala Gln Ser Leu Leu Gly Asn Thr Cys Thr Met Gln Gln Gln Gln Gln
65                  70                  75                  80

Thr Gln Pro Leu Pro Ser Met Pro Leu Pro Met Pro Pro Thr Thr Pro
                85                  90                  95

Lys Ser Glu Asn Glu Ser Ile Ser Ser Gly Arg Glu Glu Leu Ser Pro
            100                 105                 110

Ala Ser Ser Ile Asn Gly Cys Ser Thr Asp Gly Glu Ala Arg Arg Gln
        115                 120                 125

Lys Lys Gly Pro Ala Pro Arg Gln Gln Glu Glu Leu
```

<210> SEQ ID NO 12
<211> LENGTH: 271
<212> TYPE: DNA
<213> ORGANISM: herpes simplex virus 7

<400> SEQUENCE: 12

```
atgggccta aaagaagcg taaagtcgcc cccccgaccg atgtcagcct ggggacgag      60
ctccacttag acggcgagga cgtggcgatg gcgcatgccg acgcgctaga cgatttcgat    120
ctggacatgt tggggacgg ggattccccg gggccgggat ttaccccca cgactccgcc    180
ccctacggcg ctctggatat ggccgacttc gagtttgagc agatgtttac cgatgccctt    240
ggaattgacg agtacggtgg ggaattcccg g                                    271
```

<210> SEQ ID NO 13
<211> LENGTH: 90
<212> TYPE: PRT
<213> ORGANISM: herpes simplex virus 7

<400> SEQUENCE: 13

```
Met Gly Pro Lys Lys Arg Lys Val Ala Pro Thr Asp Val Ser
1               5                   10                  15

Leu Gly Asp Glu Leu His Leu Asp Gly Glu Asp Val Ala Met Ala His
            20                  25                  30

Ala Asp Ala Leu Asp Asp Phe Asp Leu Asp Met Leu Gly Asp Gly Asp
        35                  40                  45

Ser Pro Gly Pro Gly Phe Thr Pro His Asp Ser Ala Pro Tyr Gly Ala
    50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Pro
                85                  90
```

<210> SEQ ID NO 14
<211> LENGTH: 307
<212> TYPE: DNA
<213> ORGANISM: Saccharomyces cerevisiae

<400> SEQUENCE: 14

```
atgggtgctc ctccaaaaaa gaagagaaag gtagctggta tcaataaaga tatcgaggag     60
tgcaatgcca tcattgagca gtttatcgac tacctgcgca ccggacagga gatgccgatg    120
gaaatggcgg atcaggcgat taacgtggtg ccgggcatga cgccgaaaac cattcttcac    180
gccgggccgc cgatccagcc tgactggctg aaatcgaatg gttttcatga aattgaagcg    240
gatgttaacg ataccagcct cttgctgagt ggagatgcct cctaccctta tgatgtgcca    300
gattatg                                                                307
```

<210> SEQ ID NO 15
<211> LENGTH: 102
<212> TYPE: PRT
<213> ORGANISM: Saccharomyces cerevisiae

<400> SEQUENCE: 15

```
Met Gly Ala Pro Pro Lys Lys Arg Lys Val Ala Gly Ile Asn Lys
1               5                   10                  15

Asp Ile Glu Glu Cys Asn Ala Ile Ile Glu Gln Phe Ile Asp Tyr Leu
            20                  25                  30
```

```
Arg Thr Gly Gln Glu Met Pro Met Glu Met Ala Asp Gln Ala Ile Asn
            35                  40                  45

Val Val Pro Gly Met Thr Pro Lys Thr Ile Leu His Ala Gly Pro Pro
    50                  55                  60

Ile Gln Pro Asp Trp Leu Lys Ser Asn Gly Phe His Glu Ile Glu Ala
65                  70                  75                  80

Asp Val Asn Asp Thr Ser Leu Leu Leu Ser Gly Asp Ala Ser Tyr Pro
                85                  90                  95

Tyr Asp Val Pro Asp Tyr
            100
```

```
<210> SEQ ID NO 16
<211> LENGTH: 807
<212> TYPE: DNA
<213> ORGANISM: Homo sapiens

<400> SEQUENCE: 16
cccatggaat tccagtacct gccagataca gacgatcgtc accggattga ggagaaacgt      60
aaaaggacat atgagacctt caagagcatc atgaagaaga gtcctttcag cggacccacc     120 gaccccggc ctccacctcg acgcattgct gtgccttccc gcagctcagc ttctgtcccc      180
aagccagcac cccagcccta tccctttacg tcatccctga gcaccatcaa ctatgatgag     240 tttccacca tggtgtttcc ttctgggcag atcagccagg cctcggcctt ggccccggcc      300
cctccccaag tcctgcccca ggctccagcc cctgcccctg ctccagccat ggtatcagct     360
ctggcccagg ccccagcccc tgtcccagtc ctagccccag gccctcctca ggctgtggcc     420
ccacctgccc ccaagcccac ccaggctggg gaaggaacgc tgtcagaggc cctgctgcag     480
ctgcagtttg atgatgaaga cctgggggcc ttgcttggca acagcacaga cccagctgtg     540
ttcacagacc tggcatccgt cgacaactcc gagtttcagc agctgctgaa ccagggcata     600
cctgtggccc cccacacaac tgagcccatg ctgatggagt accctgaggc tataactcgc     660
ctagtgacag gggcccagag gcccccccgac ccagctcctg ctccactggg ggccccgggg    720
ctccccaatg gcctcctttc aggagatgaa gacttctcct ccattgcgga catggacttc     780
tcagccctgc tgagtcagat cagctcc                                          807
```

```
<210> SEQ ID NO 17
<211> LENGTH: 269
<212> TYPE: PRT
<213> ORGANISM: Homo sapiens

<400> SEQUENCE: 17

Pro Met Glu Phe Gln Tyr Leu Pro Asp Thr Asp Asp Arg His Arg Ile
1               5                   10                  15

Glu Glu Lys Arg Lys Arg Thr Tyr Glu Thr Phe Lys Ser Ile Met Lys
            20                  25                  30

Lys Ser Pro Phe Ser Gly Pro Thr Asp Pro Arg Pro Pro Arg Arg
        35                  40                  45

Ile Ala Val Pro Ser Arg Ser Ser Ala Ser Val Pro Lys Pro Ala Pro
    50                  55                  60

Gln Pro Tyr Pro Phe Thr Ser Ser Leu Ser Thr Ile Asn Tyr Asp Glu
65                  70                  75                  80

Phe Pro Thr Met Val Phe Pro Ser Gly Gln Ile Ser Gln Ala Ser Ala
                85                  90                  95

Leu Ala Pro Ala Pro Pro Gln Val Leu Pro Gln Ala Pro Ala Pro Ala
            100                 105                 110
```

```
Pro Ala Pro Ala Met Val Ser Ala Leu Ala Gln Ala Pro Ala Pro Val
        115                 120                 125

Pro Val Leu Ala Pro Gly Pro Pro Gln Ala Val Ala Pro Pro Ala Pro
    130                 135                 140

Lys Pro Thr Gln Ala Gly Glu Gly Thr Leu Ser Glu Ala Leu Leu Gln
145                 150                 155                 160

Leu Gln Phe Asp Asp Glu Asp Leu Gly Ala Leu Leu Gly Asn Ser Thr
                165                 170                 175

Asp Pro Ala Val Phe Thr Asp Leu Ala Ser Val Asp Asn Ser Glu Phe
            180                 185                 190

Gln Gln Leu Leu Asn Gln Gly Ile Pro Val Ala Pro His Thr Thr Glu
        195                 200                 205

Pro Met Leu Met Glu Tyr Pro Glu Ala Ile Thr Arg Leu Val Thr Gly
    210                 215                 220

Ala Gln Arg Pro Pro Asp Pro Ala Pro Ala Pro Leu Gly Ala Pro Gly
225                 230                 235                 240

Leu Pro Asn Gly Leu Leu Ser Gly Asp Glu Asp Phe Ser Ser Ile Ala
                245                 250                 255

Asp Met Asp Phe Ser Ala Leu Leu Ser Gln Ile Ser Ser
            260                 265

<210> SEQ ID NO 18
<211> LENGTH: 34
<212> TYPE: DNA
<213> ORGANISM: Artificial Sequence
<220> FEATURE:
<223> OTHER INFORMATION: 1X Ecdysone response element (EcRE)

<400> SEQUENCE: 18
tcgagagaca agggttcaat gcacttgtcc aatg                              34

<210> SEQ ID NO 19
<211> LENGTH: 19
<212> TYPE: DNA
<213> ORGANISM: Artificial Sequence
<220> FEATURE:
<223> OTHER INFORMATION: GAL4 response element

<400> SEQUENCE: 19
ggagtactgt cctccgagc                                               19

<210> SEQ ID NO 20
<211> LENGTH: 36
<212> TYPE: DNA
<213> ORGANISM: Artificial Sequence
<220> FEATURE:
<223> OTHER INFORMATION: 2xLexAop response element

<400> SEQUENCE: 20
ctgctgtata taaaaccagt ggttatatgt acagta                            36

<210> SEQ ID NO 21
<211> LENGTH: 1008
<212> TYPE: DNA
<213> ORGANISM: Choristoneura fumiferana

<400> SEQUENCE: 21
cggcctgagt gcgtagtacc cgagactcag tgcgccatga agcggaaaga gaagaaagca    60
cagaaggaga aggacaaact gcctgtcagc acgacgacgg tggacgacca catgccgccc   120
attatgcagt gtgaacctcc acctcctgaa gcagcaagga ttcacgaagt ggtcccaagg   180
```

| | |
|---|---|
| tttctctccg acaagctgtt ggagacaaac cggcagaaaa acatccccca gttgacagcc | 240 |
| aaccagcagt tccttatcgc caggctcatc tggtaccagg acgggtacga gcagccttct | 300 |
| gatgaagatt tgaagaggat tacgcagacg tggcagcaag cggacgatga aaacgaagag | 360 |
| tcggacactc ccttccgcca gatcacagag atgactatcc tcacggtcca acttatcgtg | 420 |
| gagttcgcga agggattgcc agggttcgcc aagatctcgc agcctgatca aattacgctg | 480 |
| cttaaggctt gctcaagtga ggtaatgatg ctccgagtcg cgcgacgata cgatgcggcc | 540 |
| tcagacagtg ttctgttcgc gaacaaccaa gcgtacactc gcgacaacta ccgcaaggct | 600 |
| ggcatggcct acgtcatcga ggatctactg cacttctgcc ggtgcatgta ctctatggcg | 660 |
| ttggacaaca tccattacgc gctgctcacg gctgtcgtca tcttttctga ccggccaggg | 720 |
| ttggagcagc cgcaactggt ggaagagatc cagcggtact acctgaatac gctccgcatc | 780 |
| tatatcctga accagctgag cgggtcggcg cgttcgtccg tcatatacgg caagatcctc | 840 |
| tcaatcctct ctgagctacg cacgctcggc atgcaaaact ccaacatgtg catctccctc | 900 |
| aagctcaaga acagaaagct gccgcctttc ctcgaggaga tctgggatgt ggcggacatg | 960 |
| tcgcacaccc aaccgccgcc tatcctcgag tcccccacga atctctag | 1008 |

<210> SEQ ID NO 22
<211> LENGTH: 309
<212> TYPE: DNA
<213> ORGANISM: Simian virus 40

<400> SEQUENCE: 22

| | |
|---|---|
| ggtgtggaaa gtccccaggc tccccagcag gcagaagtat gcaaagcatg catctcaatt | 60 |
| agtcagcaac caggtgtgga aagtccccag gctccccagc aggcagaagt atgcaaagca | 120 |
| tgcatctcaa ttagtcagca accatagtcc cgcccctaac tccgcccatc ccgcccctaa | 180 |
| ctccgcccag ttccgcccat tctccgcccc atggctgact aattttttt atttatgcag | 240 |
| aggccgaggc cgcctcggcc tctgagctat tccagaagta gtgaggaggc ttttttggag | 300 |
| gcctaggct | 309 |

<210> SEQ ID NO 23
<211> LENGTH: 635
<212> TYPE: DNA
<213> ORGANISM: Locusta migratoria

<400> SEQUENCE: 23

| | |
|---|---|
| tgcatacaga catgcctgtt gaacgcatac ttgaagctga aaacgagtg gagtgcaaag | 60 |
| cagaaaacca agtggaatat gagctggtgg agtgggctaa acacatcccg cacttcacat | 120 |
| ccctacctct ggaggaccag gttctcctcc tcagagcagg ttggaatgaa ctgctaattg | 180 |
| cagcattttc acatcgatct gtagatgtta aagatggcat agtacttgcc actggtctca | 240 |
| cagtgcatcg aaattctgcc catcaagctg gagtcggcac aatatttgac agagttttga | 300 |
| cagaactggt agcaaagatg agagaaatga aaatggataa aactgaactt ggctgcttgc | 360 |
| gatctgttat tcttttcaat ccagaggtga ggggtttgaa atccgcccag gaagttgaac | 420 |
| ttctacgtga aaaagtatat gccgctttgg aagaatatac tagaacaaca catcccgatg | 480 |
| aaccaggaag atttgcaaaa cttttgcttc gtctgccttc tttacgttcc ataggcctta | 540 |
| agtgtttgga gcatttgttt ttctttcgcc ttattggaga tgttccaatt gatacgttcc | 600 |
| tgatggagat gcttgaatca ccttctgatt cataa | 635 |

<210> SEQ ID NO 24

```
<211> LENGTH: 6
<212> TYPE: DNA
<213> ORGANISM: Artificial sequence
<220> FEATURE:
<223> OTHER INFORMATION: synthetic promoter

<400> SEQUENCE: 24 tatata                                                                        6

<210> SEQ ID NO 25
<211> LENGTH: 1653
<212> TYPE: DNA
<213> ORGANISM: Photinus pyralis

<400> SEQUENCE: 25
atggaagacg ccaaaaacat aaagaaaggc ccggcgccat tctatcctct agaggatgga       60
accgctggag agcaactgca taaggctatg aagagatacg ccctggttcc tggaacaatt      120
gcttttacag atgcacatat cgaggtgaac atcacgtacg cggaatactt cgaaatgtcc      180
gttcggttgg cagaagctat gaaacgatat gggctgaata caaatcacag aatcgtcgta      240
tgcagtgaaa actctcttca attctttatg ccggtgttgg cgcgttatt tatcggagtt       300 gcagttgcgc ccgcgaacga catttataat gaacgtgaat tgctcaacag tatgaacatt      360
tcgcagccta ccgtagtgtt tgtttccaaa aaggggttgc aaaaaatttt gaacgtgcaa      420
aaaaaattac caataatcca gaaaattatt atcatggatt ctaaaacgga ttaccaggga      480
tttcagtcga tgtacacgtt cgtcacatct catctacctc ccggttttaa tgaatacgat      540
tttgtaccag agtcctttga tcgtgacaaa acaattgcac tgataatgaa ttcctctgga      600
tctactgggt tacctaaggg tgtggcccct ccgcatagaa ctgcctgcgt cagattctcg      660
catgccagag atcctatttt tggcaatcaa atcattccgg atactgcgat tttaagtgtt      720
gttccattcc atcacggttt tggaatgttt actacactcg gatatttgat atgtggattt      780
cgagtcgtct taatgtatag atttgaagaa gagctgtttt tacgatccct tcaggattac      840
aaaattcaaa gtgcgttgct agtaccaacc ctatttttcat tcttcgccaa aagcactctg    900
attgacaaat acgatttatc taatttacac gaaattgctt ctgggggcgc acctctttcg      960
aaagaagtcg ggaagcggt tgcaaaacgc ttccatcttc cagggatacg acaaggatat     1020
gggctcactg agactacatc agctattctg attacacccg aggggatga taaaccgggc     1080 gcggtcggta agttgttcc attttttgaa gcgaaggttg tggatctgga taccgggaaa      1140
acgctgggcg ttaatcagag aggcgaatta tgtgtcagag acctatgat tatgtccggt      1200 tatgtaaaca atccggaagc gaccaacgcc ttgattgaca aggatggatg gctacattct     1260
ggagacatag cttactggga cgaagacgaa cacttcttca tagttgaccg cttgaagtct     1320
ttaattaaat acaaaggata tcaggtggcc cccgctgaat tggaatcgat attgttacaa     1380
caccccaaca tcttcgacgc gggcgtggca ggtcttcccg acgatgacgc cggtgaactt     1440
cccgccgccg ttgttgtttt ggagcacgga aagacgatga cggaaaaaga gatcgtggat     1500
tacgtcgcca gtcaagtaac aaccgcgaaa aagttgcgcg gaggagttgt gtttgtggac    1560
gaagtaccga aaggtcttac cggaaaactc gacgcaagaa aatcagaga gatcctcata     1620 aaggccaaga agggcggaaa gtccaaattg taa                                 1653

<210> SEQ ID NO 26
<211> LENGTH: 541
<212> TYPE: PRT
<213> ORGANISM: Choristoneura fumiferana
```

<400> SEQUENCE: 26

```
Met Arg Arg Arg Trp Ser Asn Asn Gly Gly Phe Gln Thr Leu Arg Met
1               5                   10                  15

Leu Glu Glu Ser Ser Ser Glu Val Thr Ser Ser Ala Leu Gly Leu
            20                  25                  30

Pro Ala Ala Met Val Met Ser Pro Glu Ser Leu Ala Ser Pro Glu Tyr
            35                  40                  45

Gly Gly Leu Glu Leu Trp Gly Tyr Asp Asp Gly Leu Ser Tyr Asn Thr
        50                  55                  60

Ala Gln Ser Leu Leu Gly Asn Thr Cys Thr Met Gln Gln Gln Gln
65                  70                  75                  80

Thr Gln Pro Leu Pro Ser Met Pro Leu Pro Met Pro Pro Thr Thr Pro
                85                  90                  95

Lys Ser Glu Asn Glu Ser Ile Ser Ser Gly Arg Glu Glu Leu Ser Pro
            100                 105                 110

Ala Ser Ser Ile Asn Gly Cys Ser Thr Asp Gly Glu Ala Arg Arg Gln
            115                 120                 125

Lys Lys Gly Pro Ala Pro Arg Gln Gln Glu Glu Leu Cys Leu Val Cys
130                 135                 140

Gly Asp Arg Ala Ser Gly Tyr His Tyr Asn Ala Leu Thr Cys Glu Gly
145                 150                 155                 160

Cys Lys Gly Phe Phe Arg Arg Ser Val Thr Lys Asn Ala Val Tyr Ile
                165                 170                 175

Cys Lys Phe Gly His Ala Cys Glu Met Asp Met Tyr Met Arg Arg Lys
            180                 185                 190

Cys Gln Glu Cys Arg Leu Lys Lys Cys Leu Ala Val Gly Met Arg Pro
            195                 200                 205

Glu Cys Val Val Pro Glu Thr Gln Cys Ala Met Lys Arg Lys Glu Lys
210                 215                 220

Lys Ala Gln Lys Glu Lys Asp Lys Leu Pro Val Ser Thr Thr Thr Val
225                 230                 235                 240

Asp Asp His Met Pro Pro Ile Met Gln Cys Glu Pro Pro Pro Pro Glu
                245                 250                 255

Ala Ala Arg Ile His Glu Val Val Pro Arg Phe Leu Ser Asp Lys Leu
            260                 265                 270

Leu Glu Thr Asn Arg Gln Lys Asn Ile Pro Gln Leu Thr Ala Asn Gln
            275                 280                 285

Gln Phe Leu Ile Ala Arg Leu Ile Trp Tyr Gln Asp Gly Tyr Glu Gln
        290                 295                 300

Pro Ser Asp Glu Asp Leu Lys Arg Ile Thr Gln Thr Trp Gln Gln Ala
305                 310                 315                 320

Asp Asp Glu Asn Glu Glu Ser Asp Thr Pro Phe Arg Gln Ile Thr Glu
                325                 330                 335

Met Thr Ile Leu Thr Val Gln Leu Ile Val Glu Phe Ala Lys Gly Leu
            340                 345                 350

Pro Gly Phe Ala Lys Ile Ser Gln Pro Asp Gln Ile Thr Leu Leu Lys
            355                 360                 365

Ala Cys Ser Ser Glu Val Met Met Leu Arg Val Ala Arg Arg Tyr Asp
        370                 375                 380

Ala Ala Ser Asp Ser Val Leu Phe Ala Asn Asn Gln Ala Tyr Thr Arg
385                 390                 395                 400

Asp Asn Tyr Arg Lys Ala Gly Met Ala Tyr Val Ile Glu Asp Leu Leu
                405                 410                 415
```

-continued

```
His Phe Cys Arg Cys Met Tyr Ser Met Ala Leu Asp Asn Ile His Tyr
            420                 425                 430

Ala Leu Leu Thr Ala Val Val Ile Phe Ser Asp Arg Pro Gly Leu Glu
            435                 440                 445

Gln Pro Gln Leu Val Glu Glu Ile Gln Arg Tyr Tyr Leu Asn Thr Leu
450                 455                 460

Arg Ile Tyr Ile Leu Asn Gln Leu Ser Gly Ser Ala Arg Ser Ser Val
465                 470                 475                 480

Ile Tyr Gly Lys Ile Leu Ser Ile Leu Ser Glu Leu Arg Thr Leu Gly
                485                 490                 495

Met Gln Asn Ser Asn Met Cys Ile Ser Leu Lys Leu Lys Asn Arg Lys
            500                 505                 510

Leu Pro Pro Phe Leu Glu Glu Ile Trp Asp Val Ala Asp Met Ser His
            515                 520                 525

Thr Gln Pro Pro Pro Ile Leu Glu Ser Pro Thr Asn Leu
            530                 535                 540
```

<210> SEQ ID NO 27
<211> LENGTH: 29
<212> TYPE: DNA
<213> ORGANISM: Artificial
<220> FEATURE:
<223> OTHER INFORMATION: primer

<400> SEQUENCE: 27
gtcggacact ccctaccgcc agatcacag                29

<210> SEQ ID NO 28
<211> LENGTH: 29
<212> TYPE: DNA
<213> ORGANISM: Artificial
<220> FEATURE:
<223> OTHER INFORMATION: primer

<400> SEQUENCE: 28
ctgtgatctg gcggtaggga gtgtccgac                29

<210> SEQ ID NO 29
<211> LENGTH: 31
<212> TYPE: DNA
<213> ORGANISM: Artificial
<220> FEATURE:
<223> OTHER INFORMATION: primer

<400> SEQUENCE: 29
gtcggacact ccctggcgcc agatcacaga g              31

<210> SEQ ID NO 30
<211> LENGTH: 31
<212> TYPE: DNA
<213> ORGANISM: Artificial
<220> FEATURE:
<223> OTHER INFORMATION: primer

<400> SEQUENCE: 30
ctctgtgatc tggcgccagg gagtgtccga c              31

<210> SEQ ID NO 31
<211> LENGTH: 29
<212> TYPE: DNA
<213> ORGANISM: Artificial
<220> FEATURE:
<223> OTHER INFORMATION: primer

```
<400> SEQUENCE: 31
gtcggacact cccttgcgcc agatcacag                                  29

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
ctgtgatctg gcgcaaggga gtgtccgac                                  29

<210> SEQ ID NO 33
<211> LENGTH: 33
<212> TYPE: DNA
<213> ORGANISM: Artificial
<220> FEATURE:
<223> OTHER INFORMATION: primer

<400> SEQUENCE: 33
gaggctgaca ctcccaaccg ccagatcaca gag                             33

<210> SEQ ID NO 34
<211> LENGTH: 33
<212> TYPE: DNA
<213> ORGANISM: Artificial
<220> FEATURE:
<223> OTHER INFORMATION: primer

<400> SEQUENCE: 34
ctctgtgatc tggcggttgg gagtgtcagc ctc                             33

<210> SEQ ID NO 35
<211> LENGTH: 29
<212> TYPE: DNA
<213> ORGANISM: Artificial
<220> FEATURE:
<223> OTHER INFORMATION: primer

<400> SEQUENCE: 35
gtcggacact ccccgccgcc agatcacag                                  29

<210> SEQ ID NO 36
<211> LENGTH: 29
<212> TYPE: DNA
<213> ORGANISM: Artificial
<220> FEATURE:
<223> OTHER INFORMATION: primer

<400> SEQUENCE: 36
ctgtgatctg gcggcgggga gtgtccgac                                  29

<210> SEQ ID NO 37
<211> LENGTH: 29
<212> TYPE: DNA
<213> ORGANISM: Artificial
<220> FEATURE:
<223> OTHER INFORMATION: primer

<400> SEQUENCE: 37
gtcggacact cccaagcgcc agatcacag                                  29

<210> SEQ ID NO 38
<211> LENGTH: 29
<212> TYPE: DNA
```

```
<213> ORGANISM: Artificial
<220> FEATURE:
<223> OTHER INFORMATION: primer

<400> SEQUENCE: 38
ctgtgatctg gcgcttggga gtgtccgac                                    29

<210> SEQ ID NO 39
<211> LENGTH: 32
<212> TYPE: DNA
<213> ORGANISM: Artificial
<220> FEATURE:
<223> OTHER INFORMATION: primer

<400> SEQUENCE: 39
ctcccttccg ccagaacaca gagatgacta tc                                32

<210> SEQ ID NO 40
<211> LENGTH: 32
<212> TYPE: DNA
<213> ORGANISM: Artificial
<220> FEATURE:
<223> OTHER INFORMATION: primer

<400> SEQUENCE: 40
gatagtcatc tctgtgttct ggcggaaggg ag                                32

<210> SEQ ID NO 41
<211> LENGTH: 28
<212> TYPE: DNA
<213> ORGANISM: Artificial
<220> FEATURE:
<223> OTHER INFORMATION: primer

<400> SEQUENCE: 41
ctcccttccg ccagctcaca gagatgac                                     28

<210> SEQ ID NO 42
<211> LENGTH: 28
<212> TYPE: DNA
<213> ORGANISM: Artificial
<220> FEATURE:
<223> OTHER INFORMATION: primer

<400> SEQUENCE: 42
gtcatctctg tgagctggcg gaagggag                                     28

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
cactcccttc cgccagatga cagagatgac                                   30

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
gtcatctctg tcatctggcg gaagggagtg                                   30
```

```
<210> SEQ ID NO 45
<211> LENGTH: 35
<212> TYPE: DNA
<213> ORGANISM: Artificial
<220> FEATURE:
<223> OTHER INFORMATION: primer

<400> SEQUENCE: 45
cccttccgcc agatcatgga gatgactatc ctcac                                35

<210> SEQ ID NO 46
<211> LENGTH: 35
<212> TYPE: DNA
<213> ORGANISM: Artificial
<220> FEATURE:
<223> OTHER INFORMATION: primer

<400> SEQUENCE: 46
gtgaggatag tcatctccat gatctggcgg aaggg                                35

<210> SEQ ID NO 47
<211> LENGTH: 33
<212> TYPE: DNA
<213> ORGANISM: Artificial
<220> FEATURE:
<223> OTHER INFORMATION: primer

<400> SEQUENCE: 47
cttccgccag atcagagaga tgactatcct cac                                  33

<210> SEQ ID NO 48
<211> LENGTH: 33
<212> TYPE: DNA
<213> ORGANISM: Artificial
<220> FEATURE:
<223> OTHER INFORMATION: primer

<400> SEQUENCE: 48
gtgaggatag tcatctctct gatctggcgg aag                                  33

<210> SEQ ID NO 49
<211> LENGTH: 37
<212> TYPE: DNA
<213> ORGANISM: Artificial
<220> FEATURE:
<223> OTHER INFORMATION: primer

<400> SEQUENCE: 49
ctcccttccg ccagatctgg gagatgacta tcctcac                              37

<210> SEQ ID NO 50
<211> LENGTH: 37
<212> TYPE: DNA
<213> ORGANISM: Artificial
<220> FEATURE:
<223> OTHER INFORMATION: primer

<400> SEQUENCE: 50
gtgaggatag tcatctccca gatctggcgg aagggag                              37

<210> SEQ ID NO 51
<211> LENGTH: 35
<212> TYPE: DNA
<213> ORGANISM: Artificial
<220> FEATURE:
<223> OTHER INFORMATION: primer
```

```
<400> SEQUENCE: 51
cccttccgcc agatcctaga gatgactatc ctcac                              35

<210> SEQ ID NO 52
<211> LENGTH: 35
<212> TYPE: DNA
<213> ORGANISM: Artificial
<220> FEATURE:
<223> OTHER INFORMATION: primer

<400> SEQUENCE: 52
gtgaggatag tcatctctag gatctggcgg aaggg                              35

<210> SEQ ID NO 53
<211> LENGTH: 37
<212> TYPE: DNA
<213> ORGANISM: Artificial
<220> FEATURE:
<223> OTHER INFORMATION: primer

<400> SEQUENCE: 53
ctcccttccg ccagatcgag gagatgacta tcctcac                            37

<210> SEQ ID NO 54
<211> LENGTH: 37
<212> TYPE: DNA
<213> ORGANISM: Artificial
<220> FEATURE:
<223> OTHER INFORMATION: primer

<400> SEQUENCE: 54
gtgaggatag tcatctcctc gatctggcgg aagggag                            37

<210> SEQ ID NO 55
<211> LENGTH: 31
<212> TYPE: DNA
<213> ORGANISM: Artificial
<220> FEATURE:
<223> OTHER INFORMATION: primer

<400> SEQUENCE: 55
cttccgccag atcccagaga tgactatcct c                                  31

<210> SEQ ID NO 56
<211> LENGTH: 31
<212> TYPE: DNA
<213> ORGANISM: Artificial
<220> FEATURE:
<223> OTHER INFORMATION: primer

<400> SEQUENCE: 56
gaggatagtc atctctggga tctggcggaa g                                  31

<210> SEQ ID NO 57
<211> LENGTH: 33
<212> TYPE: DNA
<213> ORGANISM: Artificial
<220> FEATURE:
<223> OTHER INFORMATION: primer

<400> SEQUENCE: 57
cttccgccag atcggagaga tgactatcct cac                                33

<210> SEQ ID NO 58
<211> LENGTH: 33
<212> TYPE: DNA
```

```
<213> ORGANISM: Artificial
<220> FEATURE:
<223> OTHER INFORMATION: primer

<400> SEQUENCE: 58
gtgaggatag tcatctctcc gatctggcgg aag                              33

<210> SEQ ID NO 59
<211> LENGTH: 33
<212> TYPE: DNA
<213> ORGANISM: Artificial
<220> FEATURE:
<223> OTHER INFORMATION: primer

<400> SEQUENCE: 59
cttccgccag atccaagaga tgactatcct cac                              33

<210> SEQ ID NO 60
<211> LENGTH: 33
<212> TYPE: DNA
<213> ORGANISM: Artificial
<220> FEATURE:
<223> OTHER INFORMATION: primer

<400> SEQUENCE: 60
gtgaggatag tcatctcttg gatctggcgg aag                              33

<210> SEQ ID NO 61
<211> LENGTH: 35
<212> TYPE: DNA
<213> ORGANISM: Artificial
<220> FEATURE:
<223> OTHER INFORMATION: primer

<400> SEQUENCE: 61
cccttccgcc agatcgtaga gatgactatc ctcac                            35

<210> SEQ ID NO 62
<211> LENGTH: 35
<212> TYPE: DNA
<213> ORGANISM: Artificial
<220> FEATURE:
<223> OTHER INFORMATION: primer

<400> SEQUENCE: 62
gtgaggatag tcatctctac gatctggcgg aaggg                            35

<210> SEQ ID NO 63
<211> LENGTH: 33
<212> TYPE: DNA
<213> ORGANISM: Artificial
<220> FEATURE:
<223> OTHER INFORMATION: primer

<400> SEQUENCE: 63
cgccagatca cagagtggac tatcctcacg gtc                              33

<210> SEQ ID NO 64
<211> LENGTH: 33
<212> TYPE: DNA
<213> ORGANISM: Artificial
<220> FEATURE:
<223> OTHER INFORMATION: primer

<400> SEQUENCE: 64
gaccgtgagg atagtccact ctgtgatctg gcg                              33
```

<210> SEQ ID NO 65
<211> LENGTH: 31
<212> TYPE: DNA
<213> ORGANISM: Artificial
<220> FEATURE:
<223> OTHER INFORMATION: primer

<400> SEQUENCE: 65
ccagatcaca gagacgacta tcctcacggt c                                      31

<210> SEQ ID NO 66
<211> LENGTH: 31
<212> TYPE: DNA
<213> ORGANISM: Artificial
<220> FEATURE:
<223> OTHER INFORMATION: primer

<400> SEQUENCE: 66
gaccgtgagg atagtcgtct ctgtgatctg g                                      31

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
gctcaagtga ggtactgatg ctccgagtcg                                        30

<210> SEQ ID NO 68
<211> LENGTH: 30
<212> TYPE: DNA
<213> ORGANISM: Artificial
<220> FEATURE:
<223> OTHER INFORMATION: primer

<400> SEQUENCE: 68
cgactcggag catcagtacc tcacttgagc                                        30

<210> SEQ ID NO 69
<211> LENGTH: 32
<212> TYPE: DNA
<213> ORGANISM: Artificial
<220> FEATURE:
<223> OTHER INFORMATION: primer

<400> SEQUENCE: 69
gctcaagtga ggtagagatg ctccgagtcg cg                                     32

<210> SEQ ID NO 70
<211> LENGTH: 32
<212> TYPE: DNA
<213> ORGANISM: Artificial
<220> FEATURE:
<223> OTHER INFORMATION: primer

<400> SEQUENCE: 70
cgcgactcgg agcatctcta cctcacttga gc                                     32

<210> SEQ ID NO 71
<211> LENGTH: 33
<212> TYPE: DNA
<213> ORGANISM: Artificial
<220> FEATURE:
<223> OTHER INFORMATION: primer

```
<400> SEQUENCE: 71
gaggtaatga tgctccacgt cgcgcgacga tac                          33

<210> SEQ ID NO 72
<211> LENGTH: 33
<212> TYPE: DNA
<213> ORGANISM: Artificial
<220> FEATURE:
<223> OTHER INFORMATION: primer

<400> SEQUENCE: 72
gtatcgtcgc gcgacgtgga gcatcattac ctc                          33

<210> SEQ ID NO 73
<211> LENGTH: 39
<212> TYPE: DNA
<213> ORGANISM: Artificial
<220> FEATURE:
<223> OTHER INFORMATION: primer

<400> SEQUENCE: 73
gtgaggtaat gatgctcatg gtcgcgcgac gatacgatg                    39

<210> SEQ ID NO 74
<211> LENGTH: 39
<212> TYPE: DNA
<213> ORGANISM: Artificial
<220> FEATURE:
<223> OTHER INFORMATION: primer

<400> SEQUENCE: 74
catcgtatcg tcgcgcgacc atgagcatca ttacctcac                    39

<210> SEQ ID NO 75
<211> LENGTH: 36
<212> TYPE: DNA
<213> ORGANISM: Artificial
<220> FEATURE:
<223> OTHER INFORMATION: primer

<400> SEQUENCE: 75
gtgaggtaat gatgctctgg gtcgcgcgac gatacg                       36

<210> SEQ ID NO 76
<211> LENGTH: 36
<212> TYPE: DNA
<213> ORGANISM: Artificial
<220> FEATURE:
<223> OTHER INFORMATION: primer

<400> SEQUENCE: 76
cgtatcgtcg cgcgacccag agcatcatta cctcac                       36

<210> SEQ ID NO 77
<211> LENGTH: 30
<212> TYPE: DNA
<213> ORGANISM: Artificial
<220> FEATURE:
<223> OTHER INFORMATION: primer

<400> SEQUENCE: 77
gtaatgatgc tccgactcgc gcgacgatac                              30

<210> SEQ ID NO 78
<211> LENGTH: 30
<212> TYPE: DNA
```

-continued

<213> ORGANISM: Artificial
<220> FEATURE:
<223> OTHER INFORMATION: primer

<400> SEQUENCE: 78
gtatcgtcgc gcgagtcgga gcatcattac                                         30

<210> SEQ ID NO 79
<211> LENGTH: 37
<212> TYPE: DNA
<213> ORGANISM: Artificial
<220> FEATURE:
<223> OTHER INFORMATION: primer

<400> SEQUENCE: 79
gaggtaatga tgctccgatg ggcgcgacga tacgatg                                 37

<210> SEQ ID NO 80
<211> LENGTH: 37
<212> TYPE: DNA
<213> ORGANISM: Artificial
<220> FEATURE:
<223> OTHER INFORMATION: primer

<400> SEQUENCE: 80
catcgtatcg tcgcgcccat cggagcatca ttacctc                                 37

<210> SEQ ID NO 81
<211> LENGTH: 32
<212> TYPE: DNA
<213> ORGANISM: Artificial
<220> FEATURE:
<223> OTHER INFORMATION: primer

<400> SEQUENCE: 81
ggtaatgatg ctccgatccg cgcgacgata cg                                      32

<210> SEQ ID NO 82
<211> LENGTH: 32
<212> TYPE: DNA
<213> ORGANISM: Artificial
<220> FEATURE:
<223> OTHER INFORMATION: primer

<400> SEQUENCE: 82
cgtatcgtcg cgcggatcgg agcatcatta cc                                      32

<210> SEQ ID NO 83
<211> LENGTH: 32
<212> TYPE: DNA
<213> ORGANISM: Artificial
<220> FEATURE:
<223> OTHER INFORMATION: primer

<400> SEQUENCE: 83
ggtaatgatg ctccgagagg cgcgacgata cg                                      32

<210> SEQ ID NO 84
<211> LENGTH: 32
<212> TYPE: DNA
<213> ORGANISM: Artificial
<220> FEATURE:
<223> OTHER INFORMATION: primer

<400> SEQUENCE: 84
cgtatcgtcg cgcctctcgg agcatcatta cc                                      32

```
<210> SEQ ID NO 85
<211> LENGTH: 32
<212> TYPE: DNA
<213> ORGANISM: Artificial
<220> FEATURE:
<223> OTHER INFORMATION: primer

<400> SEQUENCE: 85
ggtaatgatg ctccgaaccg cgcgacgata cg                                32

<210> SEQ ID NO 86
<211> LENGTH: 32
<212> TYPE: DNA
<213> ORGANISM: Artificial
<220> FEATURE:
<223> OTHER INFORMATION: primer

<400> SEQUENCE: 86
cgtatcgtcg cgcggttcgg agcatcatta cc                                32

<210> SEQ ID NO 87
<211> LENGTH: 30
<212> TYPE: DNA
<213> ORGANISM: Artificial
<220> FEATURE:
<223> OTHER INFORMATION: primer

<400> SEQUENCE: 87
gcggcctcag acagtattct gttcgcgaac                                   30

<210> SEQ ID NO 88
<211> LENGTH: 30
<212> TYPE: DNA
<213> ORGANISM: Artificial
<220> FEATURE:
<223> OTHER INFORMATION: primer

<400> SEQUENCE: 88
gttcgcgaac agaatactgt ctgaggccgc                                   30

<210> SEQ ID NO 89
<211> LENGTH: 34
<212> TYPE: DNA
<213> ORGANISM: Artificial
<220> FEATURE:
<223> OTHER INFORMATION: primer

<400> SEQUENCE: 89
ctcagacagt gttctgtggg cgaacaacca agcg                              34

<210> SEQ ID NO 90
<211> LENGTH: 34
<212> TYPE: DNA
<213> ORGANISM: Artificial
<220> FEATURE:
<223> OTHER INFORMATION: primer

<400> SEQUENCE: 90
cgcttggttg ttcgcccaca gaacactgtc tgag                              34

<210> SEQ ID NO 91
<211> LENGTH: 33
<212> TYPE: DNA
<213> ORGANISM: Artificial
<220> FEATURE:
<223> OTHER INFORMATION: primer
```

```
<400> SEQUENCE: 91
ctcagacagt gttctgcccg cgaacaacca agc                                33

<210> SEQ ID NO 92
<211> LENGTH: 33
<212> TYPE: DNA
<213> ORGANISM: Artificial
<220> FEATURE:
<223> OTHER INFORMATION: primer

<400> SEQUENCE: 92
gcttggttgt tcgcgggcag aacactgtct gag                                33

<210> SEQ ID NO 93
<211> LENGTH: 32
<212> TYPE: DNA
<213> ORGANISM: Artificial
<220> FEATURE:
<223> OTHER INFORMATION: primer

<400> SEQUENCE: 93
cagacagtgt tctgttggcg aacaaccaag cg                                 32

<210> SEQ ID NO 94
<211> LENGTH: 32
<212> TYPE: DNA
<213> ORGANISM: Artificial
<220> FEATURE:
<223> OTHER INFORMATION: primer

<400> SEQUENCE: 94
cgcttggttg ttcgccaaca gaacactgtc tg                                 32

<210> SEQ ID NO 95
<211> LENGTH: 35
<212> TYPE: DNA
<213> ORGANISM: Artificial
<220> FEATURE:
<223> OTHER INFORMATION: primer

<400> SEQUENCE: 95
cctcagacag tgttctgatg gcgaacaacc aagcg                              35

<210> SEQ ID NO 96
<211> LENGTH: 35
<212> TYPE: DNA
<213> ORGANISM: Artificial
<220> FEATURE:
<223> OTHER INFORMATION: primer

<400> SEQUENCE: 96
cgcttggttg ttcgccatca gaacactgtc tgagg                              35

<210> SEQ ID NO 97
<211> LENGTH: 35
<212> TYPE: DNA
<213> ORGANISM: Artificial
<220> FEATURE:
<223> OTHER INFORMATION: primer

<400> SEQUENCE: 97
cctcagacag tgttctgaac gcgaacaacc aagcg                              35

<210> SEQ ID NO 98
<211> LENGTH: 35
<212> TYPE: DNA
```

```
<213> ORGANISM: Artificial
<220> FEATURE:
<223> OTHER INFORMATION: primer

<400> SEQUENCE: 98
cgcttggttg ttcgcgttca gaacactgtc tgagg                              35

<210> SEQ ID NO 99
<211> LENGTH: 32
<212> TYPE: DNA
<213> ORGANISM: Artificial
<220> FEATURE:
<223> OTHER INFORMATION: primer

<400> SEQUENCE: 99
cagacagtgt tctgttcccg aacaaccaag cg                                 32

<210> SEQ ID NO 100
<211> LENGTH: 32
<212> TYPE: DNA
<213> ORGANISM: Artificial
<220> FEATURE:
<223> OTHER INFORMATION: primer

<400> SEQUENCE: 100
cgcttggttg ttcgggaaca gaacactgtc tg                                 32

<210> SEQ ID NO 101
<211> LENGTH: 35
<212> TYPE: DNA
<213> ORGANISM: Artificial
<220> FEATURE:
<223> OTHER INFORMATION: primer

<400> SEQUENCE: 101
gacagtgttc tgttcgagaa caaccaagcg tacac                              35

<210> SEQ ID NO 102
<211> LENGTH: 35
<212> TYPE: DNA
<213> ORGANISM: Artificial
<220> FEATURE:
<223> OTHER INFORMATION: primer

<400> SEQUENCE: 102
gtgtacgctt ggttgttctc gaacagaaca ctgtc                              35

<210> SEQ ID NO 103
<211> LENGTH: 42
<212> TYPE: DNA
<213> ORGANISM: Artificial
<220> FEATURE:
<223> OTHER INFORMATION: primer

<400> SEQUENCE: 103
cagacagtgt tctgttcaac aacaaccaag cgtacactcg cg                      42

<210> SEQ ID NO 104
<211> LENGTH: 42
<212> TYPE: DNA
<213> ORGANISM: Artificial
<220> FEATURE:
<223> OTHER INFORMATION: primer

<400> SEQUENCE: 104
cgcgagtgta cgcttggttg ttgttgaaca gaacactgtc tg                      42
```

```
<210> SEQ ID NO 105
<211> LENGTH: 39
<212> TYPE: DNA
<213> ORGANISM: Artificial
<220> FEATURE:
<223> OTHER INFORMATION: primer

<400> SEQUENCE: 105
cagacagtgt tctgttctgg aacaaccaag cgtacactc                              39

<210> SEQ ID NO 106
<211> LENGTH: 39
<212> TYPE: DNA
<213> ORGANISM: Artificial
<220> FEATURE:
<223> OTHER INFORMATION: primer

<400> SEQUENCE: 106
gagtgtacgc ttggttgttc cagaacagaa cactgtctg                              39

<210> SEQ ID NO 107
<211> LENGTH: 37
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n is a, c, g, or t

<400> SEQUENCE: 107
gcgtacactc gcgacnnnta ccgcaaggct ggcatgg                                37

<210> SEQ ID NO 108
<211> LENGTH: 37
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (20)..(22)
<223> OTHER INFORMATION: n is a, c, g, or t

<400> SEQUENCE: 108
ccatgccagc cttgcggtan nngtcgcgag tgtacgc                                37

<210> SEQ ID NO 109
<211> LENGTH: 31
<212> TYPE: DNA
<213> ORGANISM: Artificial
<220> FEATURE:
<223> OTHER INFORMATION: primer

<400> SEQUENCE: 109
cactcgcgac aactggcgca aggctggcat g                                      31

<210> SEQ ID NO 110
<211> LENGTH: 31
<212> TYPE: DNA
<213> ORGANISM: Artificial
<220> FEATURE:
<223> OTHER INFORMATION: primer

<400> SEQUENCE: 110
catgccagcc ttgcgccagt tgtcgcgagt g                                      31
```

<210> SEQ ID NO 111
<211> LENGTH: 34
<212> TYPE: DNA
<213> ORGANISM: Artificial
<220> FEATURE:
<223> OTHER INFORMATION: primer

<400> SEQUENCE: 111
cactcgcgac aacatgcgca aggctggcat ggcc                              34

<210> SEQ ID NO 112
<211> LENGTH: 34
<212> TYPE: DNA
<213> ORGANISM: Artificial
<220> FEATURE:
<223> OTHER INFORMATION: primer

<400> SEQUENCE: 112
ggccatgcca gccttgcgca tgttgtcgcg agtg                              34

<210> SEQ ID NO 113
<211> LENGTH: 28
<212> TYPE: DNA
<213> ORGANISM: Artificial
<220> FEATURE:
<223> OTHER INFORMATION: primer

<400> SEQUENCE: 113
caaggctggc ccggcctacg tcatcgag                                    28

<210> SEQ ID NO 114
<211> LENGTH: 28
<212> TYPE: DNA
<213> ORGANISM: Artificial
<220> FEATURE:
<223> OTHER INFORMATION: primer

<400> SEQUENCE: 114
ctcgatgacg taggccgggc cagccttg                                    28

<210> SEQ ID NO 115
<211> LENGTH: 26
<212> TYPE: DNA
<213> ORGANISM: Artificial
<220> FEATURE:
<223> OTHER INFORMATION: primer

<400> SEQUENCE: 115
caaggctggc agggcctacg tcatcg                                      26

<210> SEQ ID NO 116
<211> LENGTH: 26
<212> TYPE: DNA
<213> ORGANISM: Artificial
<220> FEATURE:
<223> OTHER INFORMATION: primer

<400> SEQUENCE: 116
cgatgacgta ggccctgcca gccttg                                      26

<210> SEQ ID NO 117
<211> LENGTH: 29
<212> TYPE: DNA
<213> ORGANISM: Artificial
<220> FEATURE:
<223> OTHER INFORMATION: primer

<400> SEQUENCE: 117
gcaaggctgg cgaggcctac gtcatcgag                                                29

<210> SEQ ID NO 118
<211> LENGTH: 29
<212> TYPE: DNA
<213> ORGANISM: Artificial
<220> FEATURE:
<223> OTHER INFORMATION: primer

<400> SEQUENCE: 118
ctcgatgacg taggcctcgc cagccttgc                                                29

<210> SEQ ID NO 119
<211> LENGTH: 26
<212> TYPE: DNA
<213> ORGANISM: Artificial
<220> FEATURE:
<223> OTHER INFORMATION: primer

<400> SEQUENCE: 119
caaggctggc ctggcctacg tcatcg                                                   26

<210> SEQ ID NO 120
<211> LENGTH: 26
<212> TYPE: DNA
<213> ORGANISM: Artificial
<220> FEATURE:
<223> OTHER INFORMATION: primer

<400> SEQUENCE: 120
cgatgacgta ggccaggcca gccttg                                                   26

<210> SEQ ID NO 121
<211> LENGTH: 32
<212> TYPE: DNA
<213> ORGANISM: Artificial
<220> FEATURE:
<223> OTHER INFORMATION: primer

<400> SEQUENCE: 121
ccgcaaggct ggctgcgcct acgtcatcga gg                                            32

<210> SEQ ID NO 122
<211> LENGTH: 32
<212> TYPE: DNA
<213> ORGANISM: Artificial
<220> FEATURE:
<223> OTHER INFORMATION: primer

<400> SEQUENCE: 122
cctcgatgac gtaggcgcag ccagccttgc gg                                            32

<210> SEQ ID NO 123
<211> LENGTH: 29
<212> TYPE: DNA
<213> ORGANISM: Artificial
<220> FEATURE:
<223> OTHER INFORMATION: primer

<400> SEQUENCE: 123
ccgcaaggct ggcggggcct acgtcatcg                                                29

<210> SEQ ID NO 124
<211> LENGTH: 29
<212> TYPE: DNA

```
<213> ORGANISM: Artificial
<220> FEATURE:
<223> OTHER INFORMATION: primer

<400> SEQUENCE: 124
cgatgacgta ggccccgcca gccttgcgg                              29

<210> SEQ ID NO 125
<211> LENGTH: 29
<212> TYPE: DNA
<213> ORGANISM: Artificial
<220> FEATURE:
<223> OTHER INFORMATION: primer

<400> SEQUENCE: 125
ccgcaaggct ggcatagcct acgtcatcg                              29

<210> SEQ ID NO 126
<211> LENGTH: 29
<212> TYPE: DNA
<213> ORGANISM: Artificial
<220> FEATURE:
<223> OTHER INFORMATION: primer

<400> SEQUENCE: 126
cgatgacgta ggctatgcca gccttgcgg                              29

<210> SEQ ID NO 127
<211> LENGTH: 27
<212> TYPE: DNA
<213> ORGANISM: Artificial
<220> FEATURE:
<223> OTHER INFORMATION: primer

<400> SEQUENCE: 127
gcaaggctgg cgtggcctac gtcatcg                                27

<210> SEQ ID NO 128
<211> LENGTH: 27
<212> TYPE: DNA
<213> ORGANISM: Artificial
<220> FEATURE:
<223> OTHER INFORMATION: primer

<400> SEQUENCE: 128
cgatgacgta ggccacgcca gccttgc                                27

<210> SEQ ID NO 129
<211> LENGTH: 29
<212> TYPE: DNA
<213> ORGANISM: Artificial
<220> FEATURE:
<223> OTHER INFORMATION: primer

<400> SEQUENCE: 129
gcaaggctgg ctgggcctac gtcatcgag                              29

<210> SEQ ID NO 130
<211> LENGTH: 29
<212> TYPE: DNA
<213> ORGANISM: Artificial
<220> FEATURE:
<223> OTHER INFORMATION: primer

<400> SEQUENCE: 130
ctcgatgacg taggcccagc cagccttgc                              29
```

```
<210> SEQ ID NO 131
<211> LENGTH: 29
<212> TYPE: DNA
<213> ORGANISM: Artificial
<220> FEATURE:
<223> OTHER INFORMATION: primer

<400> SEQUENCE: 131
caaggctggc atggccgagg tcatcgagg                                           29

<210> SEQ ID NO 132
<211> LENGTH: 29
<212> TYPE: DNA
<213> ORGANISM: Artificial
<220> FEATURE:
<223> OTHER INFORMATION: primer

<400> SEQUENCE: 132
cctcgatgac ctcggccatg ccagccttg                                           29

<210> SEQ ID NO 133
<211> LENGTH: 40
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (17)..(19)
<223> OTHER INFORMATION: n is a, c, g, or t

<400> SEQUENCE: 133
ggctggcatg gcctacnnna tcgaggatct actgcacttc                               40

<210> SEQ ID NO 134
<211> LENGTH: 40
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (22)..(24)
<223> OTHER INFORMATION: n is a, c, g, or t

<400> SEQUENCE: 134
gaagtgcagt agatcctcga tnnngtaggc catgccagcc                               40

<210> SEQ ID NO 135
<211> LENGTH: 36
<212> TYPE: DNA
<213> ORGANISM: Artificial
<220> FEATURE:
<223> OTHER INFORMATION: primer

<400> SEQUENCE: 135
gcctacgtca tcgaggatat gctgcacttc tgccgg                                   36

<210> SEQ ID NO 136
<211> LENGTH: 36
<212> TYPE: DNA
<213> ORGANISM: Artificial
<220> FEATURE:
<223> OTHER INFORMATION: primer

<400> SEQUENCE: 136
ccggcagaag tgcagcatat cctcgatgac gtaggc                                   36
```

```
<210> SEQ ID NO 137
<211> LENGTH: 36
<212> TYPE: DNA
<213> ORGANISM: Artificial
<220> FEATURE:
<223> OTHER INFORMATION: primer

<400> SEQUENCE: 137
gcctacgtca tcgaggataa cctgcacttc tgccgg                                 36

<210> SEQ ID NO 138
<211> LENGTH: 36
<212> TYPE: DNA
<213> ORGANISM: Artificial
<220> FEATURE:
<223> OTHER INFORMATION: primer

<400> SEQUENCE: 138
ccggcagaag tgcaggttat cctcgatgac gtaggc                                 36

<210> SEQ ID NO 139
<211> LENGTH: 30
<212> TYPE: DNA
<213> ORGANISM: Artificial
<220> FEATURE:
<223> OTHER INFORMATION: primer

<400> SEQUENCE: 139
cgtcatcgag gatgtactgc acttctgccg                                        30

<210> SEQ ID NO 140
<211> LENGTH: 30
<212> TYPE: DNA
<213> ORGANISM: Artificial
<220> FEATURE:
<223> OTHER INFORMATION: primer

<400> SEQUENCE: 140
cggcagaagt gcagtacatc ctcgatgacg                                        30

<210> SEQ ID NO 141
<211> LENGTH: 34
<212> TYPE: DNA
<213> ORGANISM: Artificial
<220> FEATURE:
<223> OTHER INFORMATION: primer

<400> SEQUENCE: 141
gcctacgtca tcgaggatga actgcacttc tgcc                                   34

<210> SEQ ID NO 142
<211> LENGTH: 34
<212> TYPE: DNA
<213> ORGANISM: Artificial
<220> FEATURE:
<223> OTHER INFORMATION: primer

<400> SEQUENCE: 142
ggcagaagtg cagttcatcc tcgatgacgt aggc                                   34

<210> SEQ ID NO 143
<211> LENGTH: 35
<212> TYPE: DNA
<213> ORGANISM: Artificial
<220> FEATURE:
<223> OTHER INFORMATION: primer
```

<400> SEQUENCE: 143
gcatgcaaaa ctccaacaag tgcatctccc tcaag                          35

<210> SEQ ID NO 144
<211> LENGTH: 35
<212> TYPE: DNA
<213> ORGANISM: Artificial
<220> FEATURE:
<223> OTHER INFORMATION: primer

<400> SEQUENCE: 144
cttgagggag atgcacttgt tggagttttg catgc                          35

<210> SEQ ID NO 145
<211> LENGTH: 37
<212> TYPE: DNA
<213> ORGANISM: Artificial
<220> FEATURE:
<223> OTHER INFORMATION: primer

<400> SEQUENCE: 145
gcatgcaaaa ctccaactgg tgcatctccc tcaagct                        37

<210> SEQ ID NO 146
<211> LENGTH: 37
<212> TYPE: DNA
<213> ORGANISM: Artificial
<220> FEATURE:
<223> OTHER INFORMATION: primer

<400> SEQUENCE: 146
agcttgaggg agatgcacca gttggagttt tgcatgc                        37

<210> SEQ ID NO 147
<211> LENGTH: 45
<212> TYPE: DNA
<213> ORGANISM: Artificial
<220> FEATURE:
<223> OTHER INFORMATION: primer

<400> SEQUENCE: 147
ctcggcatgc aaaactccaa ctattgcatc tccctcaagc tcaag                45

<210> SEQ ID NO 148
<211> LENGTH: 45
<212> TYPE: DNA
<213> ORGANISM: Artificial
<220> FEATURE:
<223> OTHER INFORMATION: primer

<400> SEQUENCE: 148
cttgagcttg agggagatgc aatagttgga gttttgcatg ccgag                45

<210> SEQ ID NO 149
<211> LENGTH: 34
<212> TYPE: DNA
<213> ORGANISM: Artificial
<220> FEATURE:
<223> OTHER INFORMATION: primer

<400> SEQUENCE: 149
catgcaaaac tccaacgcgt gcatctccct caag                           34

<210> SEQ ID NO 150
<211> LENGTH: 34
<212> TYPE: DNA

```
<213> ORGANISM: Artificial
<220> FEATURE:
<223> OTHER INFORMATION: primer

<400> SEQUENCE: 150
cttgagggag atgcacgcgt tggagttttg catg                                34

<210> SEQ ID NO 151
<211> LENGTH: 36
<212> TYPE: DNA
<213> ORGANISM: Artificial
<220> FEATURE:
<223> OTHER INFORMATION: primer

<400> SEQUENCE: 151
ctccaacatg tgcatctcca agaagctcaa gaacag                              36

<210> SEQ ID NO 152
<211> LENGTH: 36
<212> TYPE: DNA
<213> ORGANISM: Artificial
<220> FEATURE:
<223> OTHER INFORMATION: primer

<400> SEQUENCE: 152
ctgttcttga gcttcttgga gatgcacatg ttggag                              36

<210> SEQ ID NO 153
<211> LENGTH: 36
<212> TYPE: DNA
<213> ORGANISM: Artificial
<220> FEATURE:
<223> OTHER INFORMATION: primer

<400> SEQUENCE: 153
ctccaacatg tgcatctccc gcaagctcaa gaacag                              36

<210> SEQ ID NO 154
<211> LENGTH: 36
<212> TYPE: DNA
<213> ORGANISM: Artificial
<220> FEATURE:
<223> OTHER INFORMATION: primer

<400> SEQUENCE: 154
ctgttcttga gcttgcggga gatgcacatg ttggag                              36

<210> SEQ ID NO 155
<211> LENGTH: 36
<212> TYPE: DNA
<213> ORGANISM: Artificial
<220> FEATURE:
<223> OTHER INFORMATION: primer

<400> SEQUENCE: 155
ctccaacatg tgcatctcct acaagctcaa gaacag                              36

<210> SEQ ID NO 156
<211> LENGTH: 36
<212> TYPE: DNA
<213> ORGANISM: Artificial
<220> FEATURE:
<223> OTHER INFORMATION: primer

<400> SEQUENCE: 156
ctgttcttga gcttgtagga gatgcacatg ttggag                              36
```

```
<210> SEQ ID NO 157
<211> LENGTH: 32
<212> TYPE: DNA
<213> ORGANISM: Artificial
<220> FEATURE:
<223> OTHER INFORMATION: primer

<400> SEQUENCE: 157
gctgccgcct tcatggagg agatctggga tg                              32

<210> SEQ ID NO 158
<211> LENGTH: 32
<212> TYPE: DNA
<213> ORGANISM: Artificial
<220> FEATURE:
<223> OTHER INFORMATION: primer

<400> SEQUENCE: 158
catcccagat ctcctccatg aaaggcggca gc                              32

<210> SEQ ID NO 159
<211> LENGTH: 34
<212> TYPE: DNA
<213> ORGANISM: Artificial
<220> FEATURE:
<223> OTHER INFORMATION: primer

<400> SEQUENCE: 159
gctgccgcct tcattgagg agatctggga tgtg                             34

<210> SEQ ID NO 160
<211> LENGTH: 34
<212> TYPE: DNA
<213> ORGANISM: Artificial
<220> FEATURE:
<223> OTHER INFORMATION: primer

<400> SEQUENCE: 160
cacatcccag atctcctcaa tgaaaggcgg cagc                            34

<210> SEQ ID NO 161
<211> LENGTH: 31
<212> TYPE: DNA
<213> ORGANISM: Artificial
<220> FEATURE:
<223> OTHER INFORMATION: primer

<400> SEQUENCE: 161
ctgccgcctt tccgagagga gatctgggat g                               31

<210> SEQ ID NO 162
<211> LENGTH: 31
<212> TYPE: DNA
<213> ORGANISM: Artificial
<220> FEATURE:
<223> OTHER INFORMATION: primer

<400> SEQUENCE: 162
catcccagat ctcctctcgg aaaggcggca g                               31

<210> SEQ ID NO 163
<211> LENGTH: 34
<212> TYPE: DNA
<213> ORGANISM: Artificial
<220> FEATURE:
<223> OTHER INFORMATION: primer
```

```
<400> SEQUENCE: 163
gctgccgcct ttctgggagg agatctggga tgtg                              34

<210> SEQ ID NO 164
<211> LENGTH: 34
<212> TYPE: DNA
<213> ORGANISM: Artificial
<220> FEATURE:
<223> OTHER INFORMATION: primer

<400> SEQUENCE: 164
cacatcccag atctcctccc agaaaggcgg cagc                              34

<210> SEQ ID NO 165
<211> LENGTH: 31
<212> TYPE: DNA
<213> ORGANISM: Artificial
<220> FEATURE:
<223> OTHER INFORMATION: primer

<400> SEQUENCE: 165
ctcgaggaga tcccggatgt ggcaggacat g                                 31

<210> SEQ ID NO 166
<211> LENGTH: 31
<212> TYPE: DNA
<213> ORGANISM: Artificial
<220> FEATURE:
<223> OTHER INFORMATION: primer

<400> SEQUENCE: 166
catgtcctgc cacatccggg atctcctcga g                                 31

<210> SEQ ID NO 167
<211> LENGTH: 32
<212> TYPE: DNA
<213> ORGANISM: Artificial
<220> FEATURE:
<223> OTHER INFORMATION: primer

<400> SEQUENCE: 167
cctcgaggag atcgaggatg tggcaggaca tg                                32

<210> SEQ ID NO 168
<211> LENGTH: 32
<212> TYPE: DNA
<213> ORGANISM: Artificial
<220> FEATURE:
<223> OTHER INFORMATION: primer

<400> SEQUENCE: 168
catgtcctgc cacatcctcg atctcctcga gg                                32

<210> SEQ ID NO 169
<211> LENGTH: 31
<212> TYPE: DNA
<213> ORGANISM: Artificial
<220> FEATURE:
<223> OTHER INFORMATION: primer

<400> SEQUENCE: 169
ctcgaggaga tcttggatgt ggcaggacat g                                 31

<210> SEQ ID NO 170
<211> LENGTH: 31
<212> TYPE: DNA
```

-continued

```
<213> ORGANISM: Artificial
<220> FEATURE:
<223> OTHER INFORMATION: primer

<400> SEQUENCE: 170
catgtcctgc cacatccaag atctcctcga g                                    31

<210> SEQ ID NO 171
<211> LENGTH: 34
<212> TYPE: DNA
<213> ORGANISM: Artificial
<220> FEATURE:
<223> OTHER INFORMATION: primer

<400> SEQUENCE: 171
cctcgaggag atcatggatg tggcaggaca tgtc                                 34

<210> SEQ ID NO 172
<211> LENGTH: 34
<212> TYPE: DNA
<213> ORGANISM: Artificial
<220> FEATURE:
<223> OTHER INFORMATION: primer

<400> SEQUENCE: 172
gacatgtcct gccacatcca tgatctcctc gagg                                 34

<210> SEQ ID NO 173
<211> LENGTH: 34
<212> TYPE: DNA
<213> ORGANISM: Artificial
<220> FEATURE:
<223> OTHER INFORMATION: primer

<400> SEQUENCE: 173
cctcgaggag atctacgatg tggcaggaca tgtc                                 34

<210> SEQ ID NO 174
<211> LENGTH: 34
<212> TYPE: DNA
<213> ORGANISM: Artificial
<220> FEATURE:
<223> OTHER INFORMATION: primer

<400> SEQUENCE: 174
gacatgtcct gccacatcgt agatctcctc gagg                                 34

<210> SEQ ID NO 175
<211> LENGTH: 37
<212> TYPE: DNA
<213> ORGANISM: Artificial
<220> FEATURE:
<223> OTHER INFORMATION: primer

<400> SEQUENCE: 175
ggaattcccg gggatccggc ctgagtgcgt agtaccc                              37

<210> SEQ ID NO 176
<211> LENGTH: 46
<212> TYPE: DNA
<213> ORGANISM: Artificial
<220> FEATURE:
<223> OTHER INFORMATION: primer

<400> SEQUENCE: 176
ctctctgcgg ccgcctatcc gagattcgtg ggggactcga ggatag                    46
```